(12) United States Patent
Kataria et al.

(10) Patent No.: US 7,487,182 B2
(45) Date of Patent: Feb. 3, 2009

(54) SYSTEMS AND METHODS FOR MANAGING THE DEVELOPMENT AND MANUFACTURING OF A DRUG

(75) Inventors: Anjali R. Kataria, San Carlos, CA (US); Joseph Prang, Los Gatos, CA (US); Vinay Ambekar, Saratoga, CA (US)

(73) Assignee: Conformia Software, Inc., Sunnyvale, CA (US)

( * ) Notice: Subject to any disclaimer, the term of this patent is extended or adjusted under 35 U.S.C. 154(b) by 312 days.

(21) Appl. No.: 11/430,680

(22) Filed: May 8, 2006

(65) Prior Publication Data

US 2007/0192715 A1 Aug. 16, 2007

Related U.S. Application Data

(63) Continuation-in-part of application No. 11/022,316, filed on Dec. 23, 2004, now Pat. No. 7,275,070, which is a continuation-in-part of application No. 10/914,538, filed on Aug. 9, 2004, which is a continuation of application No. 10/052,412, filed on Jan. 23, 2002, now abandoned.

(60) Provisional application No. 60/263,177, filed on Jan. 23, 2001.

(51) Int. Cl.
 G06F 7/00 (2006.01)
 G06F 17/00 (2006.01)
(52) U.S. Cl. .................. 707/104.1; 707/101; 707/102; 707/103 R
(58) Field of Classification Search ........................ None
 See application file for complete search history.

(56) References Cited

U.S. PATENT DOCUMENTS

| 5,664,112 | A |   | 9/1997  | Sturgeon et al. |
|-----------|---|---|---------|-----------------|
| 5,712,990 | A |   | 1/1998  | Henderson       |
| 5,831,859 | A |   | 11/1998 | Medeiros et al. |
| 5,847,957 | A |   | 12/1998 | Cohen et al.    |
| 6,014,729 | A | * | 1/2000  | Lannan et al. ............... 711/150 |
| 6,067,549 | A |   | 5/2000  | Smalley et al.  |

(Continued)

FOREIGN PATENT DOCUMENTS

EP 0 612 039 A3 2/1994

(Continued)

OTHER PUBLICATIONS

PJB Publications Ltd, "A Tour of Pharmaprojects." 2003, Pharmaprojects Version 5.*

(Continued)

*Primary Examiner*—Christian P. Chace
*Assistant Examiner*—Michael J Hicks
(74) *Attorney, Agent, or Firm*—Jones Day

(57) ABSTRACT

Graphical user interfaces, computer readable media, and computer systems for monitoring a chemical process. An administration module sets a plurality of user preferences associated with the chemical process. A people management module defines a user role in the chemical process. An organization module defines an organizational structure of an organization that runs the chemical process. An equipment module defines equipment used in the chemical process. A material module controls a chemical used in the chemical process. A process module defines a chemical reaction in the chemical process.

21 Claims, 35 Drawing Sheets

U.S. PATENT DOCUMENTS

| | | | |
|---|---|---|---|
| 6,243,615 B1 | 6/2001 | Neway et al. | |
| 6,256,640 B1 | 7/2001 | Smalley et al. | |
| 6,324,522 B2 | 11/2001 | Peterson et al. | |
| 6,397,115 B1 | 5/2002 | Basden | |
| 6,567,788 B1 | 5/2003 | Johnson, Jr. | |
| 6,741,998 B2 | 5/2004 | Ruth et al. | |
| 6,853,920 B2 | 2/2005 | Hsiung et al. | |
| 6,865,509 B1 | 3/2005 | Hsiung et al. | |
| 6,873,914 B2 | 3/2005 | Winfield et al. | |
| 6,904,370 B1* | 6/2005 | Levinson et al. | 702/19 |
| 6,917,845 B2 | 7/2005 | Hsiung et al. | |
| 6,947,866 B2 | 9/2005 | Staab | |
| 6,985,779 B2 | 1/2006 | Hsiung et al. | |
| 6,988,109 B2 | 1/2006 | Stanley et al. | |
| 7,031,778 B2 | 4/2006 | Hsiung et al. | |
| 7,123,978 B2 | 10/2006 | Hartman et al. | |
| 7,131,069 B1 | 10/2006 | Rush et al. | |
| 7,146,231 B2 | 12/2006 | Schleiss et al. | |
| 7,174,230 B2 | 2/2007 | Arackaparambil et al. | |
| 7,206,646 B2 | 4/2007 | Nixon et al. | |
| 2001/0049595 A1* | 12/2001 | Plumer et al. | 703/22 |
| 2001/0049673 A1 | 12/2001 | Dulong et al. | |
| 2002/0083364 A1* | 6/2002 | Christensen et al. | 714/13 |
| 2002/0165806 A1 | 11/2002 | Kataria et al. | |
| 2002/0188465 A1 | 12/2002 | Gogolak et al. | |
| 2003/0050868 A1* | 3/2003 | Hoffman et al. | 705/28 |
| 2003/0093295 A1 | 5/2003 | Lilly et al. | |
| 2004/0210473 A1 | 10/2004 | Goddard | |
| 2005/0038565 A1* | 2/2005 | Power et al. | 700/266 |
| 2005/0251278 A1* | 11/2005 | Popp | 700/110 |

FOREIGN PATENT DOCUMENTS

| | | |
|---|---|---|
| EP | 0 965 897 A1 | 12/1999 |
| GB | 2 347 234 A | 2/2000 |
| WO | WO 03/075206 A2 | 9/2003 |
| WO | WO 2004/072868 A1 | 8/2004 |

OTHER PUBLICATIONS

U.S. Appl. No. 11/633,048, filed Nov. 30, 2006, Kataria et al.

PJB Publications Ltd. "A Tour of Pharmaprojects", Pharmaprojects Web/CD-Rom Version 5: 1-40.

* cited by examiner

Metamodel Setup > Manage Category > Add Category

New Category

Status: Schema Not Created

Material Folder > Material

*Name:
*Label:
*DB Name:
Description:

Is System: ☐
Is Folder: ☐

Allow Attachments: ☐
Allow Notes: ☐
Allow Multi-record Additions: ☐
Has Record Permission: ☐
Is Basefull: ☐
Has Effectivity: ☐
Has Workflow: ☐

OK  Cancel

Metamodel Setup > Manage Attributes > Add Attribute

1. Define Attribute > 2. New Attribute Details > 3. Confirm Attribute Details

Define Attribute
*Attribute Name:
*Attribute Label:
*Attribute DB Name:
*Data Type: - Select -
Description:

Value Required:
Primary Key:
Unique:
Hidden:
Privilege Required:
Auditable:
Localizable:
Externally Derived:
Required in View:
Indexed:
Editable:
Hyperlinked:

People:User:Manage

Compare Records

| | | |
|---|---|---|
| User Id | ⊙ User01 | ⊙ roopak |
| User Name | User01 | roopak |
| Title | | |
| Effective Start Date | 2005-10-13 09:43:27.0 | 2005-10-13 12:13:09.0 |
| Effective End Date | | |
| Education | | |
| Department Id | LPRD | QC |
| Department | Lilly Product Research & Development | Quality Control |
| Site Id | | |
| Primary Site | Lilly Global Site | UNIVAR - Bruxelles |
| Email | nisha.mol@ianidea.com | roopak.k@mail.com |
| Phone | | |
| Is Primary | Yes | Yes |
| Is Locked | No | No |
| Is SuperUser | No | No |
| | Remove | Remove |

SYSTEMS AND METHODS FOR MANAGING THE DEVELOPMENT AND MANUFACTURING OF A DRUG

CROSS-REFERENCE TO RELATED APPLICATIONS

This application is a continuation-in-part of U.S. patent application Ser. No. 11/022,316, filed Dec. 23, 2004, now U.S. Pat. No. 7,275,070 which is a continuation-in-part of U.S. patent application Ser. No. 10/914,538, filed Aug. 9, 2004, which is a continuation of U.S. patent application Ser. No. 10/052,412, filed Jan. 23, 2002, now abandoned that claims the benefit of U.S. Provisional Application No. 60/263,177, filed Jan. 23, 2001, the entire contents of which are each hereby incorporated by reference herein in their entirety.

FIELD OF THE INVENTION

This invention relates to management of regulated industries. In particular, the present invention facilitates regulatory, tax compliance, inventory, e-warehouse, and product history information management of heavily regulated process industries.

BACKGROUND OF THE INVENTION

Heavily regulated and process oriented industries such as: oil & gas, food (e.g., agriculture products, processed food, meat/poultry etc.), beverages (e.g., consumable liquids such as spirits, wine, beer, juice, etc.), chemicals, consumer products (e.g., cosmetics and skin care), and pharmaceutical drugs {e.g., chemical and bioprocess development, also known as drug substance and pharmaceutical development, also known as drug product, as well as generics), share a number of common characteristics. These kinds of heavily regulated process industries are extensively regulated by local, state, federal and international agencies (e.g., Food and Drug Administration (FDA), Trade and Tax Bureau (TTB part of Treasury)) to ensure that safe and efficacious products are consumed by the public and that each of the products presented by companies in these aforementioned industries are not fraudulent or harmful (e.g., that the product integrity is maintained for the life of the product). The product integrity is proven by comparing product records at one point in time against product history records of another point in time during the development, manufacturing and commercial sale of these products. Key elements of product history information include specifications, attributes, processes, equipment, material, people involved, standards followed or established, as well as physical conditions under which products were produced. This is challenging for these kinds of heavily regulated process industries because, by nature, they tend to produce products that are dynamically changing or very complex. Thus, the information associated with these product history records becomes more difficult to manage over the lifecycle of development. For example, these industries may require highly variable raw materials such as proteins secreted from mammalian cells or grape juice extracted from agriculture vine-grapes. These raw materials are then transformed into intermediate materials and then finally into final products delivered in a safe and efficacious form ingestible by humans. Companies might also be required to preserve this product history, for example, for submission to regulatory agencies to gain approval to commercially manufacture these products. Furthermore, as companies develop new products, they may begin with the "end in mind", turning to these past product histories as "prior knowledge" and relying on their justifications and rationale to regulatory authorities on this multi-variate-dimensional "model" to prove quality is built into the process, or that they followed a "Quality by Design (QbD) approach".

Another major requirement for "heavily regulated industries" is the ability of a company to demonstrate that it's production processes from development through commercial manufacturing are fully traceable, meaning that a third party (such as an Agency, e.g., FDA) could come in and demand to see product history from one point in time to another. A single source of truth exists for each product history. For instance, a company must be able to prove that "what it is producing is indeed being produced, in the manner it claims to be being produced in." These onsite inspections, audits, and information requests often focus on a particular process for a particular set of materials from one point in time to another. Failure to provide immutable proof of product history traceability has subjected companies to hefty fines as well as shutdowns.

In addition for failure to provide proof of the process over time, these industries are usually subject to large fines-or delays in production/shutdowns for non-compliance of any part of the submission application, audits, labels, waste, emissions, safety, etc. Payment of appropriate taxes is an ongoing challenge as the payments are determined by the "amount produced" and "type" of product produced, all of which require extensive record keeping along many dimensions over time.

These industries are also "heavily process oriented" meaning that products are produced in a manner that consists of extensive combinations of steps such as complex blends, formulations and recipes. Another drawback is that in some of these industries (e.g., the pharmaceutical and beverage industries) extensive record keeping is required to create the product history "paper trail." Typically, the kind of record keeping required by these industries is a complete history of the product's lifecycle, often spanning from the raw materials to the final product and inclusive of all intermediate products across the supply chain. The type of information required in the record keeping of product history typically spans the following dimensions: personnel and their training requirements, process, materials, equipment, standards, and facility/environment information which collectively form the comprehensive information for the specified record.

These industries may also have complex order tracking for work personnel, equipment materials, processes (e.g., campaign planning and execution, work order generation, etc.). For instance, tracking the state of materials from raw material to intermediates, to final products etc. or tracking the equipment history (calibration, cleaning, usage, etc.) requires a number of different kinds/pieces of information making it a complex process. Not only does the information in these areas have to be recorded and tracked, but it must be compared to standards set both internally within a company and externally by regulating authorities. Furthermore, it must be compared to itself at differing points in time (e.g., Commercial Manufacturing takes place in Year 9 and the equipment set up, calibration, cleaning, usage must be recorded, tracked and compared against the equipment history in Year 8, which was submitted to the FDA and is what the company's license to commercially manufacture is based upon.).

These types of regulated process industries are further challenged in that a number of different indirect/input goods are produced along the path of creating the final product and all of these indirect/input/intermediate goods have be managed in a similar manner of recording information/tracking/ comparing to different points in time as described above. Visibility is essential to achieving this comprehensive record keeping and management of information in these regulated process industries, yet at present these industries have low visibility at all levels of process input and product history across the supply chain.

Currently there are no broad web-based solutions that fully meet these kinds of complex quality and product integrity needs such as comprehensive product history record keeping in process management of heavily regulated industries. In fact, many of the record keeping functions and filing processes for federal and state regulations still occur through outdated manual time-consuming means.

SUMMARY OF THE INVENTION

The present invention describes a system and a method for enabling information management across the supply chain from raw material to final product for regulated process industries. The system and method enables a company to manage extensive record keeping for heavily regulated products where the key components are often dynamically changing and are very complex to manage. The embodiments facilitate regulatory and tax database with automated compliance and tax reporting. For example, regulatory management and automated compliance are achieved by the system enabling a company to automatically demonstrate compliance with federal regulatory agency submission requirements(e.g., Pharmaceutical Development History,, Quality by Design (QbD), Chemistry Manufacturing and Controls (CMC) and Pharmaceutical Development (Drug Product) submission requirements for license to manufacture drugs in the U.S.); traceability of any dimension of drug development, and retrieval of key information necessary to meet audits, inspections, and product integrity inquisitions. Because the system and method is integrated with smart inventory and e-warehouse management solutions, the essential product history information from "candidate selection to commercial manufacturing" is automatically captured for comparisons, correlations, and verifications enabling the company to demonstrate compliance to the federal agency. For example, the full lifecycle management of raw materials, expendables and intermediates can be demonstrated. This information associated with raw materials and intermediates at each stage is cleverly and smartly leveraged into the record keeping needs of the company to demonstrate full product history of the lifecycle. The embodiments are applicable to heavily regulated industries such as, for example, beverages, food, oil, pharmaceutical drugs, and chemicals.

The present invention allows regulatory compliance integration with complete, real time web-based supply chain infrastructure to manage all essential product history from raw material stage to final product. The system has enough customization for each industry allowing the domain, regulatory and tax specificities to be appropriately addressed. Complete Product history includes key information along the essential dimensions of product development and manufacturing: people, process, materials, equipment, environment/facility and standards (regulatory and internal). The present invention allows for management of regulatory (standards) with automated compliance, tax reporting and in-process inventory management of development and production of pharmaceuticals.

The present invention provides industry-specific solutions to regulatory and tax compliance issues, including integrated industry-specific supply chain applications to assist in compliance. The present invention is designed to operate alongside existing information systems (such as ERP, MES, LIMS EDMS, etc.) to provide complimentary applications.

The system enables users to manage regulatory filings (such as the IND, NDA, BLA and ANDA), comparability protocols, post approval change processes, design space justification and rationale for process understanding (PAT), tax compliance, and inventory (raw material, excipients, additives, intermediates, final products both quarantined and released). This aspect reduces supply chain inefficiencies with a real-time, web-based, enterprise-wide supply chain infrastructure. A substantial reduction of the current cumbersome paper trail is achieved by the system and affords users a more accurate and timely compliance, thus avoiding violations and substantial fines/penalties.

The system may provide supply chain solutions to increase visibility throughout a regulated industry's operations. This aspect enables greater information management through secure access to real time information; and advanced planning. This aspect provides users worry-free management while reducing costs, inventory levels, and decreasing working capital needs. The system can be wireless ready, enabling the user to more efficiently and effectively manage critical data.

The system may provide clear comprehensive product history information, enabling the company to demonstrate product integrity and to show product traceability from one point in time to another along multiple dimensions of: people, process, materials, equipment, standards and environment/facility.

Through an extremely scalable platform, the system can enable real time web-based regulatory and tax compliance based supply chain infrastructure while also providing regulatory and tax compliance, inventory management, content management and supplier catalog management modules. Procurement, shipping management, demand and forecasting tools and regulatory e-filings complement the supply chain solutions.

The system can interface with many third party enterprise resource, planning applications and existing legacy systems. The system can be java-based, using open API systems, and can be highly scalable, flexible, robust, modular and portable (PDA and wireless capable). The system can use thin client architecture requiring only a web browser and implemented without requiring desktop installation. The system can support Secure Sockets Layer (SSL) to protect the transmission of content between the browser and the server. In addition, user identification and password protections may be embedded, as well as controls based upon user roles.

The system of the present invention through the use of a core platform and modules can provide extensive management of record keeping across multiple dimensions over time. For instance, material management functionality for the pharmaceutical manufacturing industry is provided by the system and method. Specifically, the chain of custody for drug substances can be recorded such as the starting materials, reagents, solvents, intermediates, bulk and final API. The system manages all related information for each material type (COA's, Specs, etc.). Material traceability from loading dock to "tablet" is provided by knowing with certainty the who, what, where, when and how of all materials. Furthermore, it is possible to create and locate materials. Requests, orders, inventory, dispense, dispose and transfer of materials are known. The chain of documentation is also recorded through the use of status, signoff, alerts, authentication, e-signatures, and hazard profiles. Similar functionality exists for all dimensions of pharmaceutical development over time (as mentioned above and further explained below).

The quality of the product can be managed by the system. The material qualification ID and use tests are recorded, as well as raw material specifications. Materials can be sorted and tracked on any characteristic of the material by the system (ex. evaluation date, purity).

The system can also manage the equipment used in the manufacturing process. Reservation for equipment use, as well as equipment characteristics, usage and availability can be viewed with the system. Furthermore, equipment usage, loaning borrowing, and decommission can be tracked. The maintenance and cleaning of equipment can also be tracked with the system.

Those skilled in the art will appreciate these and other advantages and benefits of various embodiments of the invention upon reading the following detailed description of a preferred embodiment with reference to the below-listed drawings.

BRIEF DESCRIPTION OF DRAWINGS

FIG. 7 illustrate how a material management module can be accessed by a material tab in accordance with an embodiment of the present invention.

FIG. 8 illustrates a user interface in accordance with an embodiment of the present invention.

FIGS. 15 and 16 illustrate how a user can add new attributes to a material category in accordance with an embodiment of the present invention.

FIG. 21 illustrates a compare records screen in accordance with an embodiment of the present invention.

DETAILED DESCRIPTION

Figure 1:
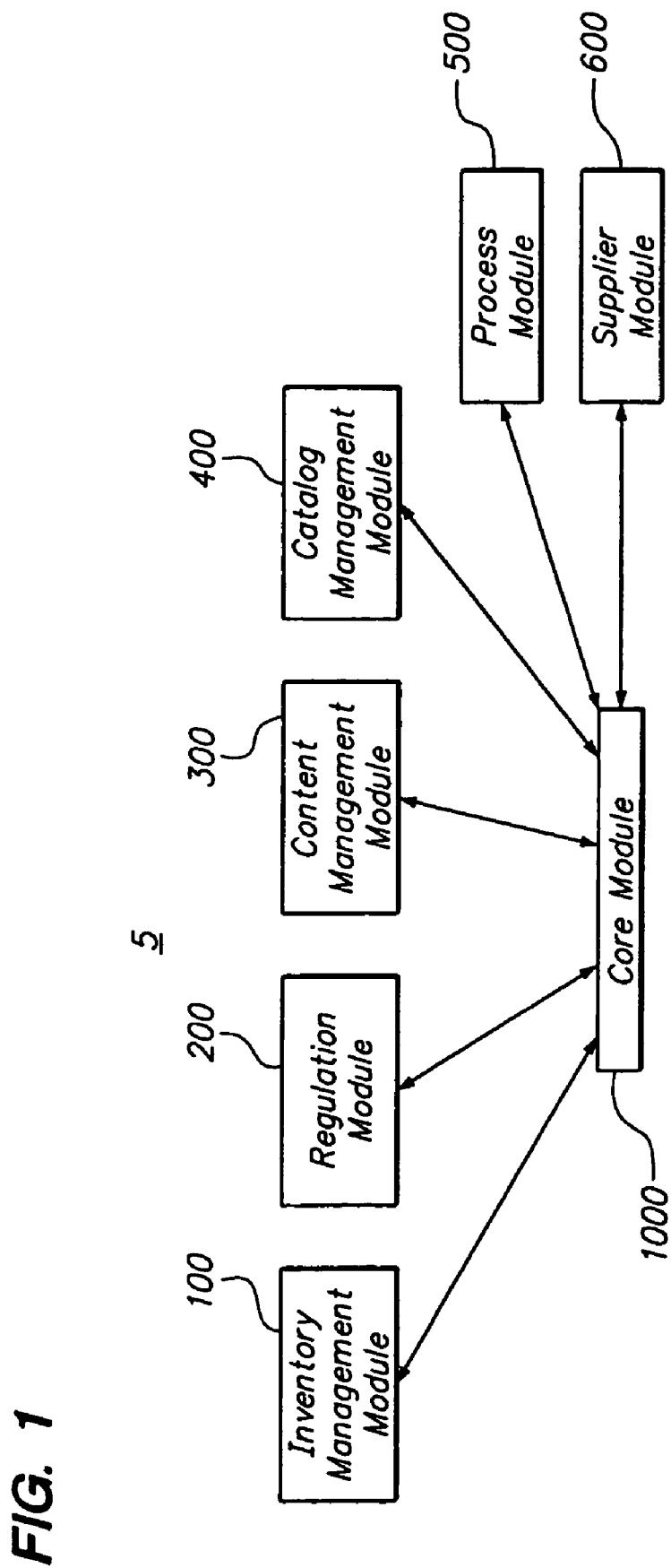
FIG. 1 is a block diagram of a system according to a first embodiment.

FIG. 1 is a block diagram of a product conformance management system 5 having an inventory management module 100, a regulation module 200, a content management module 300, a catalog management module 400, a process module 500, a supplier module 600, and a core module 1000. It will be recognized by those of ordinary skill in the art that the number and types of modules available may change on the type of industry. For example, for the pharmaceutical industry, there may also be a material management module, an equipment management module, a standards module, a method execution module, and a traceability module. In this regard, a solution for a specific industry may contain many suites which are a collection of modules. Each of the modules is independently deployable on the platform. By having the multiple modules, the solution can be easily deployed and expanded at customer sites in a phased manner.

Inventory management module 100 includes domain knowledge of the pharmaceutical industry to specifically address the needs of that industry. Specifically, the inventory management module records the movement of raw and starting materials as they move through the production process. In addition, inventory management module 100 provides visibility into a company's inventory of material (raw, intermediate, bulk and final product) at any location at the subsidiary or corporate level, as well as tracks the inventory through the production process. Inventory management module 100 implements inventory threshold levels for reorder points and compliance requirements and triggers a notification via the system, email, pager or WAP. Inventory management module 100 also provides the ability for both the manufacturer and their supplier to view internal inventory levels. Inventory management module 100 provides for receipt, issue and return of goods, movement of goods, and verification of goods locations. Accordingly, the inventory management module can track goods through the development process into and through the production cycle.

Regulation module 200 addresses the need for compliance with complex and varied federal and state regulations for pharmaceutical production. Regulation module 200 provides current regulatory and tax compliance information affecting the pharmaceutical industry. This regulatory and tax database will also include automated compliance and tax reporting. Regulation module 200 will be linked with the Federal Drug Administration (FDA), state agencies, and other on-line sources of legal information to create this database. The key components of regulation module 200 are centered around the submission process of investigational and new drug applications for chemical, biological and generic entities. Module 200 combined with the platform (core module 1000) enables an electronic product history record (ePHR) to be created for both development and manufacturing. At present, this product history record can be specific in the pharmaceutical industry to the development environment (called an electronic development record (eDR)) or to commercial manufacturing (called an electronic Product History Record (ePHR)).

The ePHR and eDR are both created automatically from the extensive record keeping functions in the system which have key pieces of information relating to the various dimensions of development over time. The dimensions of development include: people, process, materials, equipment, standards, environment/facility. The ePHR and eDR provide context around the chemical or biological structure enabling downstream and upstream development and manufacturing colleagues to capture knowledge and compare product histories between different compounds, stages, conditions, etc. Once a new chemical or biological structure is identified ("candidate selection") system 5 captures key information along the various dimensions automatically creating the eDR and ePHR.

The ePHR and eDR enable companies to meet pre-approval inspections and post approval inspections conducted by federal agencies more effectively; to gain approvals for drug applications more readily; and to produce products at a higher level of quality, with greater visibility, and in a more efficient manner. Furthermore, the eDR and ePHR enable companies to demonstrate appropriate and necessary information to transfer to downstream functional areas, offsite CMO's/third party partners (TPOs) as well as to enable remote auditing of the product history record at any point in its lifecycle. The system also provides faster and more efficient means for submitting post approval changes. The ePHR and eDR also provide faster and better resolution of "out of specification incidence" (OOS) in both Development and Manufacturing of Pharmaceutical Drugs. Ultimately, over time, companies can expect a greater level of "process understanding" and to demonstrate "quality by Design" (QbD) as the ePHR and eDR enable complex information to be aggregated in one place with context and dimensions of development preserved over time and over the life of the product. Any authorized user has the ability to search, retrieve, analyze and correlate any component of the ePHR and/or eDR to facilitate greater process understanding.

Content management module 300 is a relational database of industry-specific, company-specific, activity specific or supplier-specific information such as documents, inventory alerts, specification sheets, certificates of analysis (COA), methods, standards (both company specific or internal as well as external/agency specific).

Suppliers that sell products typically have some sort of catalog, whether it be online or in hardcopy. Catalog management module 400 provides the manufacturer with a consolidated view of similar products across a number of suppliers and provides the company with a list of ingredients, cost associated with each product, procurement related information to each product and quarantine/release information.

Process module 500 captures data from various stages of the pharmaceutical production. The captured data can include activity records or lab analyses records. It spans the lifecycle of process development from authoring a template to creating full recipes with unit operations and discrete unit actions grouped together in process cells. The records allow traceability for audit and regulatory compliance of all stages of material (from raw material to intermediates to bulk product to final product) integrated and used seamlessly within the process module (e.g. attached to the recipe). Similarly, equipment specifications needed for each process step at any level in the process system are also integrated seamlessly. Process module 500 also enables extensive record keeping through campaign planning and execution, managing demand and forecasting for development environments, and tying all process steps, people involved, equipment used, materials used/ stage, standards followed, lab condition and facility location information for the pharmaceutical development environment which has unique characteristics which must be addressed (e.g. highly iterative, integrated planning and execution, high degrees of flexibility and variability). The culmination of this process information enables the physical and chemical attributes of the new "heavily regulated" compound being developed to be managed more efficiently. By linking the chemical or biological structure to the process steps in the aforementioned manner, system 5 is able to more effectively manage the regulated process industry (such as pharmaceuticals). Moreover, the same methods applied to chemical entities are also applicable to biopharmaceutical entities and generic products.

Supplier module 600 provides the company/user the ability to manage suppliers and the associated catalog of products purchased by the company as well as the costs associated with the transaction. For example procurement of raw materials, excipients, or starting materials in the pharmaceutical industry occurs at multiple stages over time. Material procurement needs change, as the product being developed progresses from candidate selection to commercial manufacturing (e.i., purity levels of required starting materials at candidate selection time period are much higher than starting materials used in commercial manufacturing time periods). Hence, the information associated with each and every starting material must be captured along the way or "in process" and this information is typically provided by the supplier in the form of a "certificate of analysis". Because these kinds of information/ record keeping must be comparable from one time period to another, companies must record and track this information. Currently tracking is done by manual or hand processes and is very cumbersome. Supplier module 600 along with core module 1000 enables the company to have an automated system for tracking and recording this type of information.

Core module 1000 (also referred to as the "Product Conformance Management (PCM) Platform) is the base module for system 5. Core module 1000 implements the functionalities of system 5 and is a common platform that can be configured by the customer for various business and regulatory processes in the company. Core module 1000 manages the library of all information regarding material, equipment, process, people, standards and environment related to a customer's regulated process. Core module 1000 dynamically defines all attributes according to the customer's requirements. Core module 1000 provides valid values (either ranges or enumerations) and defines data types and value generation algorithms (if any). Core module 1000 can also define units of measure and support conversion between different units.

Furthermore, core module 1000 manages the states of all information objects, workflow for approval and "state" changes (e.g., management of the dynamic and highly variable changes). Sites and locations, as well as organizational hierarchy is managed by the core module 1000. Core module 1000 manages users, user groups and user functions and provides the infrastructure for setting up alerts and delivering notifications to the users subscribed to the alerts. Core module 1000 moves data between software systems in a validated mode and ensures compliance with government regulations (e.g., 21 C.F.R. Part 11). Furthermore, versioning support is provided in core module 1000. Core module 1000 also creates an audit trail of changes to the data captured in the system, attachments to any information object in the system and any number of notes attached to any information object in the system.

In order to maintain the security of system 5, core module 1000 provides access through a login which is a combination of user identification and a password. After three unsuccessful attempts, the user account should be disabled and an administrator notified. Only an administrator should have the ability to unlock the account. Additionally, details about the user name, title, email address, telephone number, effective dates of usage of the system and the physical location of the user are maintained by core module 1000. The login service also identifies any of the applications of system 5 that are authorized for the user to access and the role in which the access is permitted.

Core module 1000 also provides external authentication support by which users can be authenticated by an external system. The externals service is called with the user's identification and password. Core module 1000 can handle successful and unsuccessful attempts similar to the authentication process within system 5. When external authentication is used, all account and password management should be handled by the external service.

System 5 can model various roles for access. These roles would not have to map to functional roles of the individual within the enterprise. The roles defined in the system are primarily used to control the access to various features of the system. Roles can be associated with an application or made available to all or a combination of applications. Roles may be location specific or enterprise wide. A user has the ability to have more than one role in the system. The role identifies the functionality of the system the role can access (e.g., menu items, screens, etc.). Furthermore, the role identifies actions the role can execute on the functionality it can access (e.g., read, write, update, delete, list, etc.). The role identifies the specific fields/attributes that are accessible.

In order to authenticate the input of records into system 5, core module 1000 supports the use of a generic method of collecting user signatures electronically. This service will be invoked by the applications when ever the requirement for an electronic signature arises. The user will be prompted for the user's ID and password which will be verified for accuracy. A reusable user interface component is available for all applications to ensure easy and consistent implementation of electronic signatures. This reusable component accepts the user's ID as a parameter and pre-fills that information when the user interface is presented to the user. This is an aid when a continuous set of signatures is needed to be accepted. Each signature is stored against the activity or information being certified/signed off by the user.

Alerts are very important to system 5. Alerts will be used for a large number of activities and pro-active notifications. Therefore, the alerts are highly scalable and generic. Customers can associate alerts to objects identified by an application at any time without having to shutdown the system.

Each application identifies objects that are expected to have alerts associated with them (e.g., work orders, material receipt, equipment schedule, etc.) and the various attributes of the object whose change of value would result in an alert. It is possible to define the type of comparison that is performed against the attribute to generate the alert. All common types of comparison—equality, inequality, greater than, lesser than, range or list, can be supported.

Types of actions which trigger alerts are user actions which change an object (create, modify, delete) and time based triggers (check overdue activities). Optionally, it is possible to attach a custom code to be executed when the alert condition is reached. This will help embed computational logic, if required for generating notifications.

In a deployed system, an administrator is able to publish the alerts that are available to the users of system 5. This is done by identifying the roles and/or users who are allowed to subscribe to a given alert. Publication is achieved through the generic system wide publish/subscribe mechanism.

When a user attempts to subscribe to alerts, only those published to the user and the user's role should be listed. Users can then choose the actual alert that they want to subscribe to and provide the information required to complete the subscription. Through a user interface, the end user is able to define the exact conditions when they want to be notified. The end user has the ability to select the object and its attributes and assign the values which would trigger the notification. Depending on the user's object level permissions, the user can specify notification criteria only for attributes the user has read access.

The user has the ability to select the method of delivery of the notification. Notifications are delivered to the user's personal alert list in system 5. Additionally, the user can choose to have the alert delivered by email. It will also be recognized that alert notifications can be delivered to pagers and cell phones.

Ensuring that the user is properly alerted is a key responsibility of system 5 and hence core module 1000. An alerts pane on each of the pages of system 5 is generated by core module 1000. The pane identifies the alert and some key attributes of the notification. When the user is active in any application of the system 5, the alerts pane is constantly updated with the latest notifications that have not been acknowledged by the user.

All notifications to the user are viewable through an interface dedicated to alert notifications. The user is able to view all of the relevant details of the notification through this interface and also manage the notifications. The user is able to acknowledge having seen the notification so that it is no longer shown in the alerts pane and/or delete the notification.

Applications of system 5 need to co-exist with multiple commercial enterprise applications and niche products, as well as with many custom in-house solutions. For successful deployments of the applications and to achieve being a repository of electronic product development, core module 1000 should be capable of easily exchanging data with other systems. To achieve this, core module 1000 provides an integration framework that is used to configure or build the integrations. The framework complies with the following requirements:

Middleware Independence. No assumptions should be made based on vendor specific middleware products. Deployment engineers should be able to configure the framework to communicate with any external system or middleware (e.g., TIBCO, WebMethods, SeeBeyond, Vitria, etc.) which may be specified by the customer. Only industry standards like web services and JMS should be supported.

XML Data Format. Data moving between the systems should be encoded in XML to conform to industry trends. Existing industry standard specifications like BatchML from World Batch Forum can be supported.

Integration Event Based Triggers. The framework can move data in real time, based on data modification triggers as well as through periodic batch mode updates. The integration framework can hook into the generic system wide alert notification framework to achieve this.

Back-end (application level) Integration Support. Based on event triggers, the framework should be able to post the data to a web service, URL (http port), JMS server, or through simple export to sequentially labeled files. The integration framework should be able to accept incoming data through a web service or a JMS server.

Bi-directional Data Exchange. System 5 can publish data out from the system as well as ability to insert and modify data within the system.

Identification of System of Record. System 5 has the ability to define a list of applications and identify one of the systems as the owner of record (master) for each data item.

Organizational Mapping. Generally the name of the organizational unit will be required to provide the context of the data being exchanged. The name given to a particular organization unit may differ between different external systems and between those of system 5. Core module 1000 provides a means of mapping these names. This mapping should not be assumed to be a simple 1<->1 mapping.

Attribute Mapping. One data item may be identified by two different names in two different systems. The framework should provide a generic name mapping functionality (for example where integrations are deployed without middleware). Mappings should be configurable on-site both during and after deployment. It should be possible to associate multiple groups of mappings with a particular external system, using mapping set identifier(s).

UOM Mapping. For parametric data it is common that the unit of measure used in the source system for a particular data item is different than the unit of measure that the target system is expecting. The integration framework should include a mechanism to handle this. The mapping should be configurable on-site both during and after deployment. It should be possible to associate multiple groups of mappings with a particular external system using mapping set identifier(s).

Backward Compatibility. The framework defines a published open API. Minor revision version changes to the API should not require changes to integrations built using the API. Where there is a version incompatibility, the version mismatch should be detected and reported.

Performance and Scalability. Transactions need to be processed in direct proportion to the number of transactions processed by system 5. Theoretically, an edit of any object in the system could trigger a data movement through the integration framework. The end-to-end delay and throughput overhead imposed on transactions by the integration framework should not be a major factor in the overall end-to-end delay or throughput experienced by the actual user.

Logging. Data exchange events are logged with errors for debug by the framework. Optionally, debug logs are available to help track data movement. All logs are at user specified locations and should be self-maintaining When a log reaches a preset size it should be closed and renamed as an archive with logging continuing to an new file.

Administration Support. The framework provides a user interface for the administrator to identify all active configured integrations (e.g., objects for which messages are being published or received) and monitor their health. The administrator can configure new integrations, enable and disable specific integrations, and inspect (e.g., debug, event, error) logs from this interface.

System Configurability. Data to be exchanged, data mapping and direction of the exchange are configurable at the time of deployment based on the needs of the customer. Configuration can be limited to certain entries in configuration files and some graphical user interface driven data entry.

A goal of system 5 is to enable information sharing. Though a database based system makes this easy to achieve, there are many instances where different pieces of information have to be specifically delivered to a user or an external interface. To achieve this, system 5 provides a generic mechanism to publish and subscribe information. The mechanism has the ability to register various objects in the application that may be a candidate for publication. The objects may be alerts, score cards, reports, data packages, etc. The rules for publishing are based on the type of object being published. The system can support three types of publication: system defined (pre-configured in the system and cannot be removed), administrator defined (managed only by the administrator), and end user defined (managed by the end user).

At the time of publication, it should be possible to identify the users, user groups and roles that are authorized to subscribe to the publication. All users in the system can look up the various alerts that have been published to them and decide which ones they want to subscribe to. It may be possible for the user to provide additional information to identify objects of their interest while subscribing to a publication. For example, while subscribing to an alert, the user can provide the condition under which a notification should be generated.

Workflow is an important and critical service provided by system 5. In any business, processes, roles and functions change constantly. It is possible to associate states and routing information to any object in the system and use the work flow mechanism to ensure that the object gets routed accordingly. System 5 is able to support a default workflow for an object as well as an operating mode specific workflow.

The application programmer can register objects types in the application that would go through a workflow. The application can trigger a workflow based on its internal logic. The workflow service determines the current state of the object and propagates it through the workflow based on the state. The state sequence is defined and controlled by the user in the transaction layer of system 5.

Workflow enables routing serially from one user to the next or parallel to multiple users from one user. Furthermore, workflow enables synchronization after parallel routing or routing to a user or user role. Optional recipients of the object whose actions will not alter the state of the object are also routed. Workflow also enables routing to backup approvers if no response is received from the primary approver within a user defined time limit. End users should be able to see the workflow an object goes through and also the current position of the object in the workflow.

Whenever an application submits an object for routing, the workflow manager determines the current state and generates an alert for the next user/users in the chain. The user can get to the actual object directly from a hyperlink on the alert notification, by locating the object from its corresponding 'Locate' page or from the list of pending activities in user's home page or workspace.

Once the user gets the object, the user is presented the list of actions that the user can take on the object. These actions will be determined by the state transition sequence defined for the object. Many industries are highly document driven. Quite often certain pieces of information of interest to users are available only in a document. It is also difficult to predict which objects in the system will have attachments. This requires a generic framework through which a user can attach a document to any object in the system that the user has permission to create. Users should be able to identify the file on the local system which is to be uploaded to a controlled shared area on the server. All users with permission to view the primary object would also be allowed to view the attachment. There should be no limit on the number of attachments that an object may have. The local system can have the viewer capable of displaying the attachment.

An application programmer should be able to register object types for life cycle management. This registration should ensure that all objects of that type are committed to an audit trail. In future releases of the platform, it should be possible to reconstruct the object through the user interface. It should be possible to determine at one place in the system all the object types that are being collected in an audit trail.

Each and every object in system 5 has a date and time stamp. The time stamp is accurate to the nearest second. Irrespective of the physical location of the user, the stamps should be in a single time zone for all objects in the system. There should not be any ambiguity about the sequence of events.

The data model layer of core module 1000 provides extreme flexibility to the developers of applications for system 5 and to end users who need to define key objects in the system. The data model layer provides the framework for building various dimensions of the system that need extensibility even after deployment. System 5 provides the ability to define new object sets and build a classification hierarchy under them. Application programmers may use the generic access functionality to manipulate the objects or define their own specific objects to implement specialized business logic. Reusable user interface components are available to invoke the functionality provided in this layer within applications.

It is possible to add a new object category at any place in the hierarchy. Adding a new category would require the user to identify its location in the hierarchy and give it a unique identification. A category's name should be unique within its hierarchy.

Once a category has been added to the hierarchy, it is possible to define the properties of the category. This would require the user to provide the name for the property, the data type and size, identify whether the value in the property should be unique, define default values for the property, and define valid enumerated values or value ranges. Typically, a category should inherit the properties of its ancestors.

Though having information about objects in each dimension in the system is helpful, being able to create relationships between dimensions is a critical requirement. System 5 is the repository for electronic development records and tracking relationships between the various dimensions is a major focus. Application programmers can register relationships between objects and the properties of the relationship. This concept can be extended to ensure that additional relationships can be created as a part of the deployment task.

The behavior of core module 1000 and the applications built on it is dependent on the operating modes configured on the system. The operating mode is a key factor determining the workflow associated with any object, the states an object passes through, and rules for verification of the data. Core module 1000 defines any number of operating modes for the system 5. Applications will use the operating mode to determine their behavior.

Default and valid values for attributes may be defined in the data model layer for the various dimensions. However, these values are subject to change based on operating modes. Additionally, the verification of data pertaining to the transactions themselves should be dependent on the operating mode. This requires the platform to provide a service for defining the verification criteria dependent of the operating mode. If such criteria is not provided at this layer, the system should default to the criteria provided in the data model layer.

For any object that needs to go through a workflow, it is possible to define state transition sequences. State sequences may vary by operating mode and/or location and it is possible to alter the state sequence. When such changes occur, the state sequence should be versioned so that it is possible to determine the exact state sequence an object passed through.

It is hard to predict all the reports required and computations that need to be done on large data sets like electronic development records. Core module 1000 has 'Locate' functions in system 5 to provide various easy methods of getting to this complex data. Since Excel is the tool of choice for many industries, users have the ability to export the data returned from these searches to Excel.

Each application within system 5 should be able to define its reports and associate them with a role. These reports are available to all the users assigned to the role. The reports may typically be defined using an external report writer and may be served by the corresponding report generator. Need for new reports rise regularly at most companies. So, it should be possible to continuously add new reports to the system and associate them with the roles defined in the system. This should ensure that the user's choice of reports is automatically updated when the user logs into the system.

Users should be able to provide search criteria for the report being requested. This will ensure that the user gets a report only for the subset they are interested in. Applications of system 5 can pre-define data packages of interest to the application. These packages may be a collection of pre-defined reports and can include score cards, checklists and search criteria within the system. Once the package is defined, it should be possible to publish it and subscribe to it using the generic publish/subscribe service of the platform.

Core module 1000 provides a generic framework for defining dashboards. These dashboards should provide aggregate visibility based on a type of object in the system. Primary objects in the dashboard would be objects such as fixed equipment at a location, currently active tickets at a location, currently active projects at a location, material staging requests at a location, various steps of a particular campaign, etc.

The user should be able to drill down into the details of any of the individual objects from the dashboard. The dashboard displays links to other related objects so that the user can also look up related information. Usability and information aggregation should be such that the dashboard should be one of the most common points of access for any application.

Applications of system 5 will be used in large corporations which have world wide operations. This automatically translates into requirements to support the variations that a user comes across due to local standards. Core module 1000 and applications of system 5 should be internationalized and should be able to support user definable date format (dd/mm/yyyy, mm/dd/yyyy and dd-mon-yyyy), user definable time format and time zone, user definable 1000s separator and radix point, and user definable units of measure. Because the system is highly configurable, all configuration information which will be part of the 'perceived' static part of the user interface should also be localizable.

Figure 4:
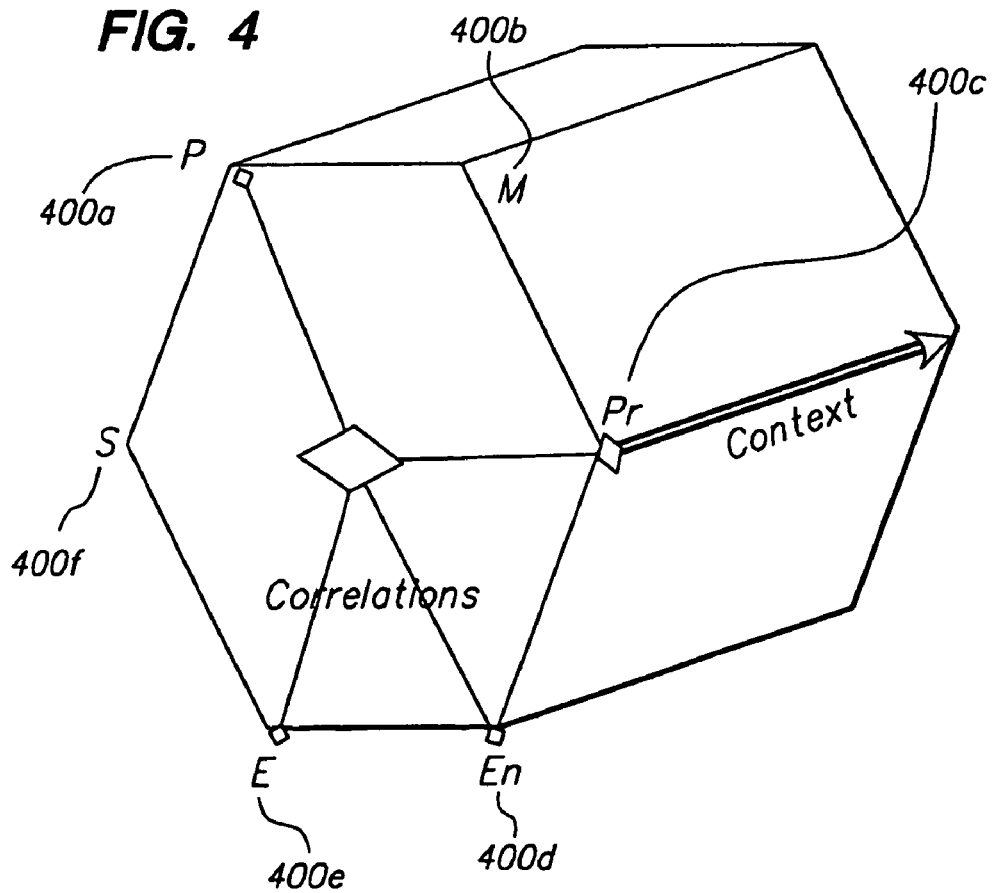
FIG. 4 illustrates the dimensions of data to be collected and analyzed.

The information collected by core module 1000 and related applications and modules is stored and sorted in a data model layer that enables correlations between information to be sorted. Specifically, the data is stored among multiple dimensions that represent all key development activities. Referring to FIG. 4, dimensions 400 are people 400a, materials 400b, process 400c, environment/facilities 400d, equipment 400e and standards 400f. It will be recognized by those of ordinary skill in the art, that the dimensions may consist of different labels if desired. Each dimension classifies the type, attribute and status of the information that is recorded with system 5. For example, equipment dimension 400e and material dimension 400b classifies the type, as well as defines the attributes and hierarchy of the equipment and material. Furthermore, both the equipment dimension 400e and the material dimension 400b sets default limits and valid values for the equipment and material. People dimension 400a classifies the roles and groups of people as well as defines the roles hierarchy and privilege access. People dimension 400a also sets default limits and valid values. Process dimension 400c classifies the type of processes and defines their hierarchy. Furthermore, process dimension 400c sets workflow and business rules and creates workflow templates. Environment dimension 400d classifies the type of environment, as well as define the attributes and hierarchy thereof. This also refers to the actual facility the processes are occurring in. Default limits and values are set in environment dimension 400d, as well as environmental reference standards. Standards dimension 400f can classify the type of standards and create structure data standards. Furthermore, the standards dimension can categorize reference documents and pre-defined processes.

Correlations can be made between the different dimensions in order to sift through the data. For example, uses of correlations include searches for related information, comparisons, verifications, review status, context, etc. The correlations can be used over time and events in order to determine the "context" of the information. For example, referring to FIG. 4, the people, process, environment and equipment dimensions 400 are correlated in order to give context to the information. The information can be located at any time for a given event (i.e., condition). The context, correlation and dimension data structure allows the electronic development record (eDR) of the material to be easily searched. In this respect, the electronic development record provides alerts and notifications, in-process operational management, knowledge management and development history archival.

Over time, the eDR enables companies to correlate process understanding to particular steps in the process, materials, and structure of chemical and biological entities.

Figure 5:
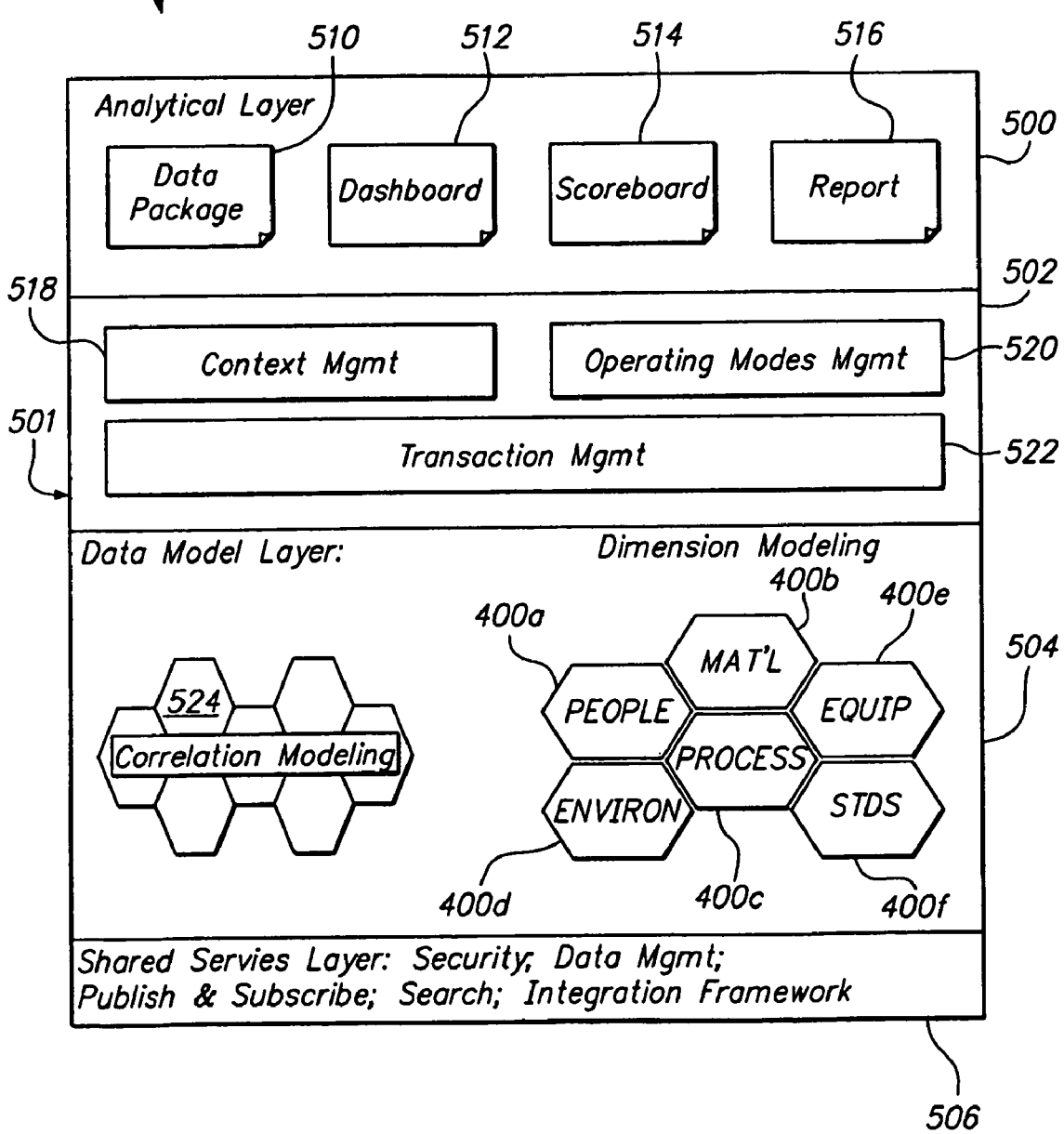
FIG. 5 illustrates a platform overview for the core module of the system.

Referring to FIG. 5, a platform overview 501 of core module 1000 is shown. Platform overview 501 illustrates four layers of architecture for core module 1000. Specifically, core module 1000 has an analytical layer 500, a transaction layer 502, a data modeling layer 504 and a shared services layer 506. Core module 1000 establishes an enterprise wide platform that provides services, functions, and data models to create a base for product records. The architecture leverages J2EE technology for open-standard, multi-tiered enterprise architecture. Furthermore, the architecture provides published interfaces for development of applications and ensures interoperability through open interfaces, web services and XML.

Analytical layer 500 includes data package 510, dashboard 512, scorecard 514, and reports 516. Analytical layer 500 provides pre-defined reports and data packages, as well a pre-configured scorecards. Furthermore, analytical layer 500 ensures dashboard visibility and role-based reports and indicators.

Transaction layer 502 has context management 518, operating modes management 520 and transaction management 522. Transaction layer 502 provides pre-defined business processes and form templates and implements best practices. Furthermore, transaction layer 502 provides a single user interface, lot traceability throughout production and in-progress visibility.

Data model layer 504 includes correlation modeling 524 and dimension modeling 400. Data model layer 504 only needs to be configured once and includes master libraries. Data model layer 504 is scalable and extendable and provides a central repository of related content. In this regard, the data model layer 504 is rapidly deployed and promotes reuse. Shared services layer 506 provides security, data management, publish and subscribe services, search services and framework integration.

Figure 2:
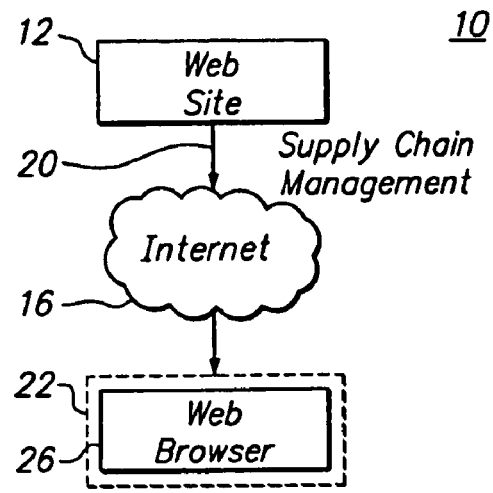
FIG. 2 is a diagram illustrating operation of an embodiment of a supply-side chain management application.

FIG. 2 is a diagram conceptually illustrating operation of an embodiment consistent with the present invention to provide infrastructure that will enable supply chain solutions for regulated industries. Supply chain solution 10 is used with a website 12, which represents one or more applications through which users can engage in worry-free management of their inventory, production, etc. A user with system 22 may interact with website 12 online (or otherwise) using a web browser 26 communicating through a network connection such as the Internet 16 or other type of network in order to obtain information about the status of their production for example.

Figure 3:
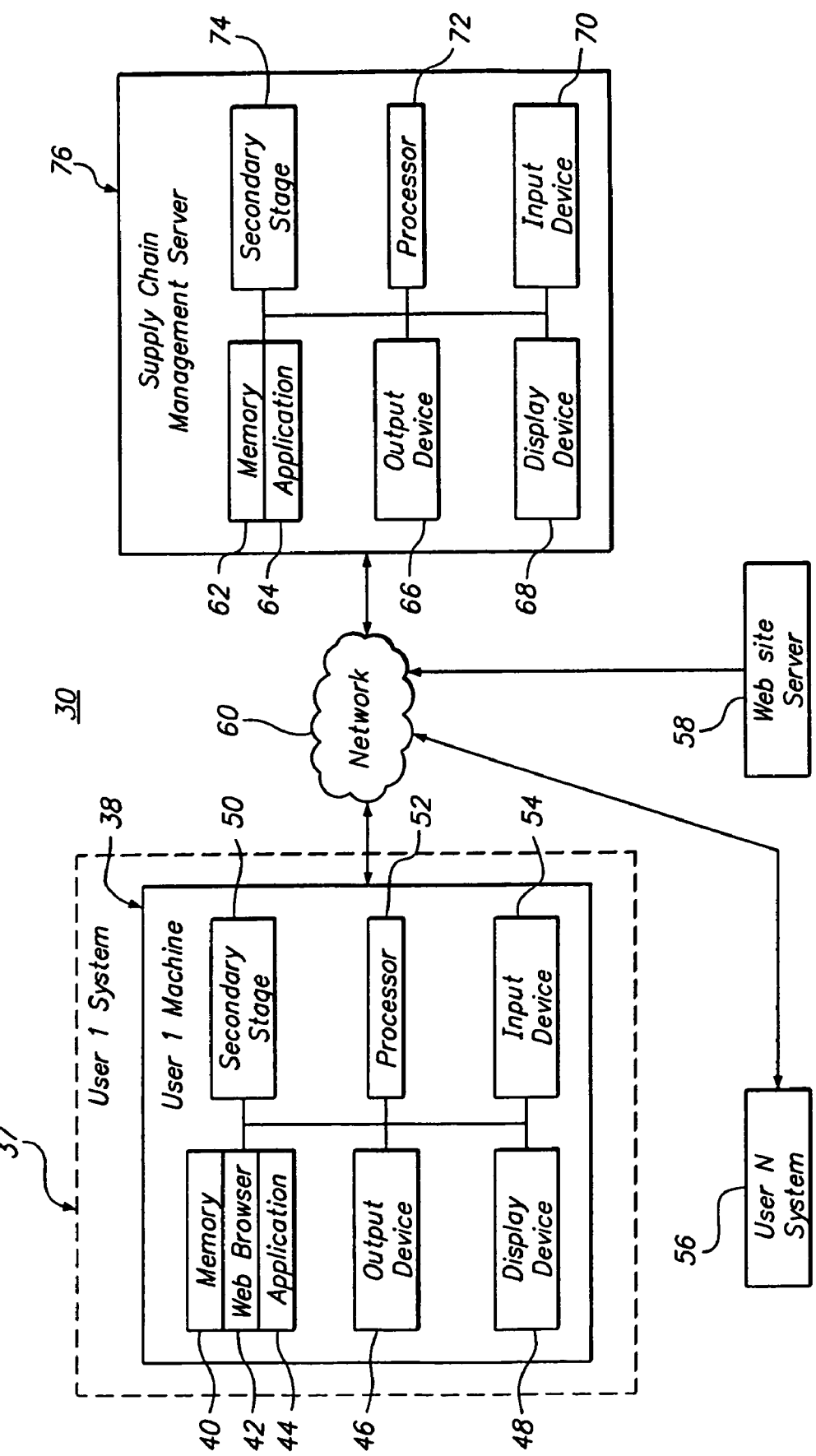
FIG. 3 is a block diagram illustrating hardware components for implementing a web based supply-side chain management application.

FIG. 3 is a block diagram illustrating exemplary hardware components for implementing system 10 for enabling supply chain solutions for regulated industries. System 30 includes a user system 37 having a user machine 38 connected with a network 60 such as the Internet, providing a network connection for participating in IP ordering. Other user systems, such as user system 56 may also be connected with network 60 for obtaining production status. User system 56, and other user systems, may include the same components as user system 37.

Users at user systems 37 and 56 interact with a server 76 to obtain production status information. Server 76 provides and maintains the web site 12 for providing a network connection to the application(s) through which users can obtain and share information. System 30 may also include the ability to access one or more web site servers 58 in order to obtain content from the World Wide Web, if desired. Only two user systems are shown for illustrative purposes, however, system 30 may include many user machines and may be scalable to add or delete user machines to or from the network.

User machine 38 illustrates typical components of a user machine. User machine 38 typically includes a memory 40, a secondary storage device 50, a processor 52, an input device 54, a display device 48, and an output device 46. Memory 40 may include random access memory (RAM) or similar types of memory, and it may store one or more applications 44, and a web browser 42, for execution by processor 52. Secondary storage device 50 may include a hard disk drive, floppy disk drive, CD-ROM drive, or other types of non-volatile data storage. Processor 52 may execute applications or programs stored in memory 40 or secondary storage 50, or received from the Internet or other network 60.

Input device 54 may include any device for entering information into machine 38, such as a keyboard, mouse, cursor-control device, touch-screen, microphone, digital camera, video recorder or camcorder. Display device 48 may include any type of device for presenting visual information such as, for example, a computer monitor or flat-screen display. Output device 46 may include any type of device for presenting a hard copy of information, such as a printer, and other types of output devices include speakers or any device for providing information in audio form.

Web browser 42 is used to access the application(s) through the web site 12 and display various web pages through which the user can collaborate information, and examples of those web pages are described below. Examples of web browsers include the Netscape Navigator program and the Microsoft Internet Explorer program. Any web browser, co-browser, or other application capable of retrieving content from a network and displaying pages or screens may be used.

Examples of user machines for interacting with the web site 12 include personal computers, laptop computers, notebook computers, palm top computers, network computers, or any processor-controlled device capable of executing a web browser or other type of application for interacting with the system.

Server 76 typically includes a memory 62, a secondary storage device 74, a processor 72, an input device 70, a display device 68, and an output device 66. Memory 62 may include RAM or similar types of memory, and it may store one or more applications 64 for execution by processor 72. Secondary storage device 74 may include a hard disk drive, floppy disk drive, CD-ROM drive, or other types of non-volatile data storage. Processor 72 executes the application(s), which is stored in memory 62 or secondary storage 74, or received from the Internet or other network 60. Input device 70 may include any device for entering information into server 76, such as a keyboard, mouse, cursor-control device, touch-screen, microphone, digital camera, video recorder or camcorder. Display device 68 may include any type of device for presenting visual information such as, for example, a computer monitor or flat-screen display. Output device 66 may include any type of device for presenting a hard copy of information, such as a printer, and other types of output devices include speakers or any device for providing information in audio form.

Also, processor 72 may execute one or more software applications 64 in order to provide the functions described in this specification, and the processing may be implemented in software, such as software modules, for execution by computers or other machines. The processing may provide and support web pages described in this specification and otherwise for display on display devices associated with the users' computers. The term "screen" refers to any visual element or combinations of visual elements for displaying information or forms; examples include, but are not limited to, user interfaces on a display device or information displayed in web pages or in windows on a display device. The screens may be formatted, for example, as web pages in Hypertext Markup Language (HTML), Extensible Markup Language (XML) or in any other suitable form for presentation on a display device depending upon applications used by users to interact with the system.

The screens include various sections, as explained below, to provide information or to receive information or commands. The term "section with respect to screens refers to a particular portion of a screen, possibly including the entire screen. Sections are selected, for example, to enter information or commands or to retrieve information or access other screens. The selection may occur, for example, by using a cursor-control device to "click on" or "double click on" the section. Alternatively, sections may be selected by entering a series of keystrokes or in other ways such as through voice commands or use of a touch screen. In addition, although the screens described below illustrate a particular arrangement and number of sections in each screen, other arrangements are possible and different numbers of sections in the screens may be used to accomplish the same or similar functions of displaying information and receiving information or commands. Also, the same section may be used for performing a number of functions, such as both displaying information and receiving a command.

Although only one server is shown, system 30 may use multiple servers as 15 necessary or desired to support the users and may also use back-up or redundant servers to prevent network downtime in the event of a failure of a particular server. In addition, although machine 37 and server 76 are depicted with various components, one skilled in the art will appreciate that these machines and the server can contain additional or different components. In addition, although aspects of an implementation consistent with the present invention are described as being stored in memory, one skilled in the art will appreciate that these aspects can also be stored on or read from other types of computer program products or computer-readable media, such as secondary storage devices, including hard disks, floppy disks, or CD-ROM; a carrier wave from the Internet or other network; or other forms of RAM or ROM. The computer-readable media may include instructions for controlling a computer system, such as machine 37 and server 76, to perform a particular method.

Non-limiting examples of drugs include, but are not limited to those that satisfy the Lipinski's Rule of Five: (i) not more than five hydrogen bond donors (e.g., OH and NH groups), (ii) not more than ten hydrogen bond acceptors (e.g. N and 0), (iii) a molecular weight under 500 Daltons, and (iv) a LogP under 5. The "Rule of Five" is so called because three of the four criteria involve the number five. See, Lipinski, 1997, Adv. Drug Del. Rev. 23, 3, which is hereby incorporated herein by reference in its entirety. In some embodiments, criteria in addition to Lipinski's Rule of Five are imposed. For example, in some embodiments, the drug has five or fewer aromatic rings, four or fewer aromatic rings, three or fewer aromatic rings, or two or fewer aromatic rings. In some embodiments, a drug is any organic compound having a molecular weight of less than 2000 Daltons. In some embodiments, the drug is any compound listed in *Approved Drug Products with Therapeutic Equivalence Evaluations*, 25th *Edition*, U.S. Department of Health and Human Services, Food and Drug Administration, Center for Drug Evaluation and Research, 2005, which is hereby incorporated by reference in its entirety.

The systems and methods of the present invention can be used to analyze drugs that are solubilized, mixed with, or interspersed in a carrier. As used herein, the term "carrier" refers to a diluent, adjuvant, excipient, or vehicle. Carriers can be liquids, such as water and oils, including those of petroleum, animal, vegetable or synthetic origin, such as peanut oil, soybean oil, mineral oil, sesame oil and the like. The vehicles (e.g., pharmaceutical vehicles) can be saline, gum acacia, gelatin, starch paste, talc, keratin, colloidal silica, urea, and the like. In addition, auxiliary, stabilizing, thickening, lubricating and coloring agents can be used. When administered to a patient, the carriers are preferably sterile. Water can be the carrier when composition is administered intravenously. Saline solutions and aqueous dextrose and glycerol solutions can also be employed as liquid vehicles, particularly for injectable solutions. Suitable vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. Compositions, if desired, can also contain minor amounts of wetting or emulsifying agents, or pH buffering agents.

Exemplary Implementation

Figure 13A:
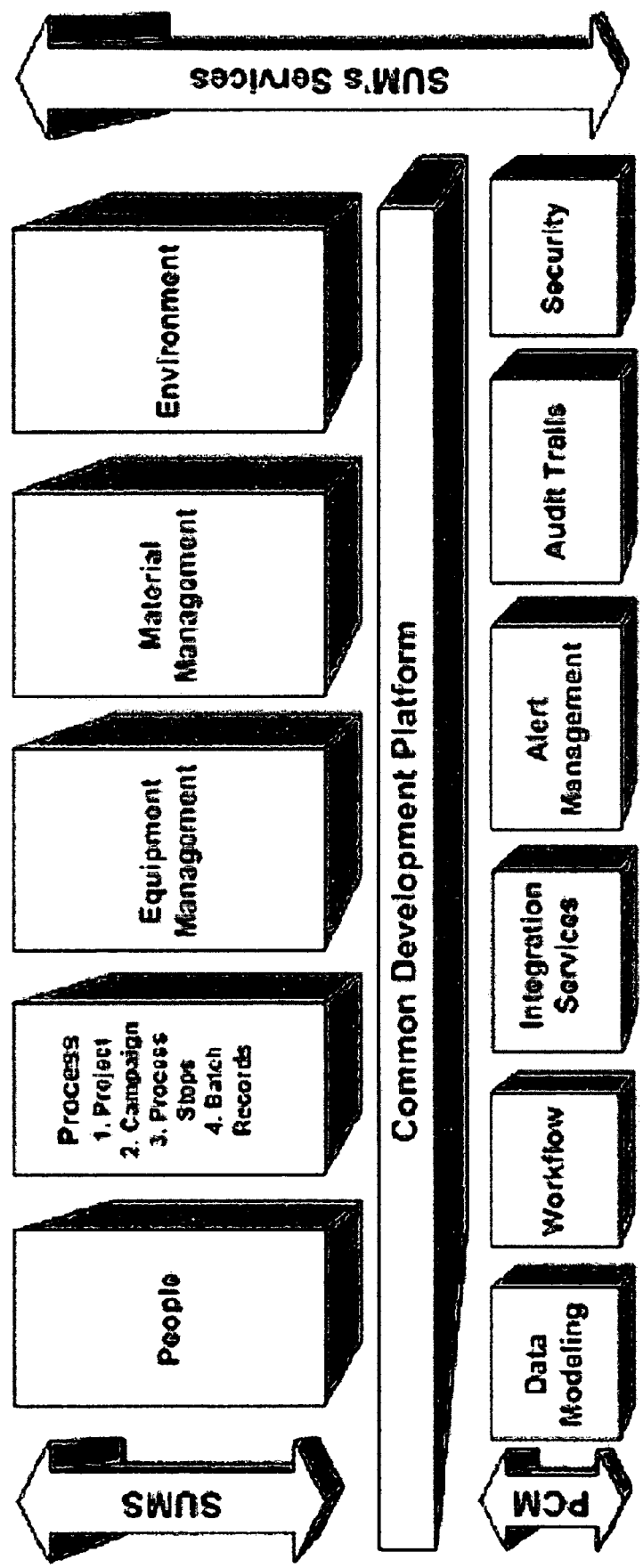
FIG. 13A illustrates an exemplary embodiment of an application that include SUMS and PCM in accordance with the present invention.
Figure 13B:
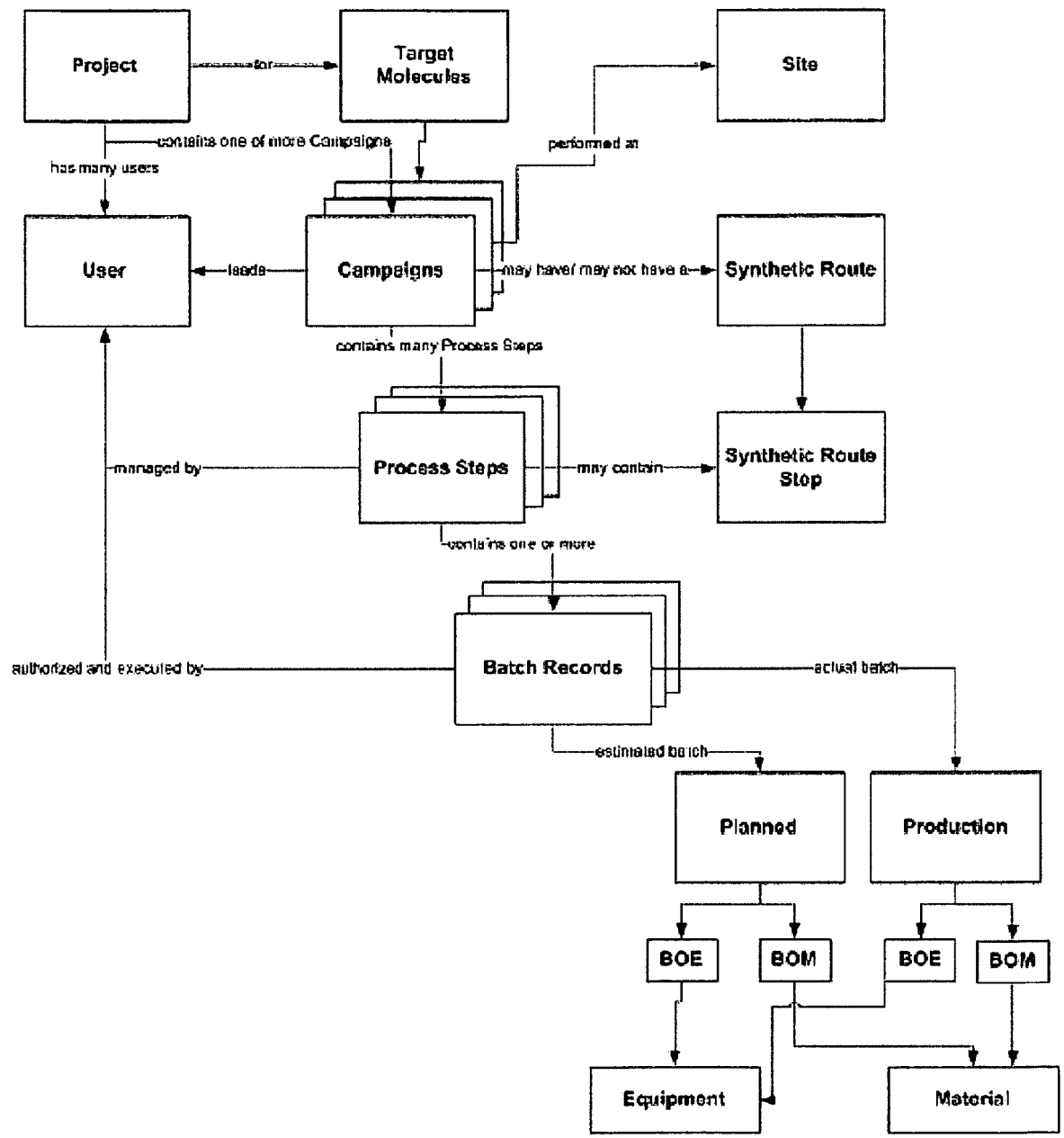
FIG. 13B provides a more detailed view of SUMS in accordance with one embodiment of the present invention.

An exemplary embodiment of an application in accordance with the present invention is disclosed in FIG. 13A. The purpose of the system depicted in FIG. 13 is to assist user in creating regulating a chemical process. This is done by creating a project. Than, one or more campaigns are created for each project. Then engineers create numerous process steps for each campaign. The engineer creates a master batch record composed of material, equipment, process steps, and assays. The engineer then creates a planned batch record composed of material, equipment, process steps, and assays. The program then generates a production batch record composed of material, equipment, process steps, and assays. A pilot plant technician then uses the production batch record to create the intermediate or API. FIG. 13B provides a more detailed view of SUMS.

To accomplish the aforementioned steps, the program comprises two major components a scale-up management system (SUMS) and a product conformance management (PCM) system. SUMS is composed of the following five components: people, material management, equipment management, process (project, campaign, process steps, and batch records), and environment. FIG. 13B provides a more detailed view of SUMS in accordance with one embodiment of the present invention. The material management component is concerned with functionality such as adding and modifying new materials, and searching for and viewing the materials. The material management component of FIG. 13 is a version of the inventory management module 100 of FIG. 1, with substantial improvements. Similarly, the equipment management component deals with adding and modifying equipment, and searching for and viewing it. In addition, its functionality includes activating and deactivating equipment and its scheduling of maintenance and calibration.

Process is composed of four components: project, campaign, process steps and batch records. The process module of FIG. 13 is a version of process module 500 of FIG. 1, with substantial improvements. With project, a user can create a new projects and modify them, add personnel, view details, and create target molecules. Within a project a user can create new campaigns and can search and view their details. In addition, within each campaign a user can create new process steps that are procedures for creating the batch lots that lead to scaled-up material being produced. Lastly, batch records are produced that list all the materials, equipment, and process steps that go into making a batch lot. The final component of SUMS, environment, primarily deals with the compliance requirements of all the regulatory agencies. As such, the environment module of FIG. 13 is a version of the regulation module 200 of FIG. 1, with substantial improvements.

The real power of the program comes from how all the above-identified components work together to provide the user with a working knowledge that enables scale-up and production of Intermediate/API batches in a uniform, consistent way, time and time again. SUMS is the main component a typical user will be employing for all the functions listed above. The other major component, PCM, is what the Administrator will be using which we now turn to. PCM is a version of core module 1000 of FIG. 1. SUMS is the specific application component that a user uses for designing your scale-up development process. PCM is the platform that provides services to SUMS, the infrastructure that makes it all work. FIG. 13 depicts the major components of both SUMS and PCM:

As mentioned, PCM is the underlying platform that supports SUMS's and it has six major service components: data modeling, workflow, integration services, alert management, audit trails, and security. The data modeling functionality is primarily expressed in its meta modeling capability whereby the administrator can create new categories (also known as business objects as well as tables) for a user. For example, he administrator adds a new blender type to the blender business object along with new blender characteristics. A user may want to automate a manual process into a workflow. The user would go to the administrator with his/her manual workflow and the administrator, using the PCM workflow tool, would build that workflow. As another example, a user needs documents to be approved by five people, so the user asks the administrator to automate this process by implementing a workflow that will automatically forward all the approval forms to all five people. Now a user need only submit the document once and it will get automatically emailed to all five members in the workflow chain for their approval or rejection. Integration Services is a generic term for PCM's Web Services (PCMWS) that allows a programmer to create new services within and external to SUMS. PCMWS is a group of SUMS's interfaces that the programmer can use to provide new services to your company. Using the alert management tool, the administrator can provide alerts for the user. For example, the administrator gives a user the permission to use an alert for a group. Now, whenever the user wants to send out an alert to all members of that group, the user only needs to address that one group, not each individual member. PCM provides audit trails on key functions thus meeting regulatory requirements. For example, whenever anyone goes in to make changes an attribute, say the boiling point attribute on a piece of equipment, that change will be logged in and kept in an audit trail file. Finally, PCM provides security at the authentication and authorization levels as well as other user permission levels.

SUMS's User Interface

Figure 18:
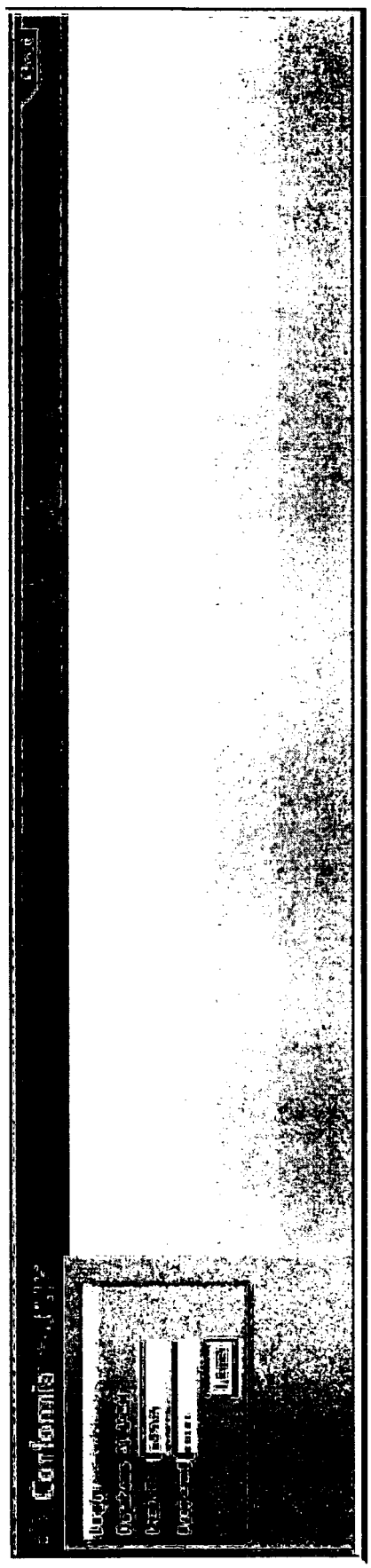
FIG. 18 illustrates a login screen in accordance with an embodiment of the present invention.
Figure 19:
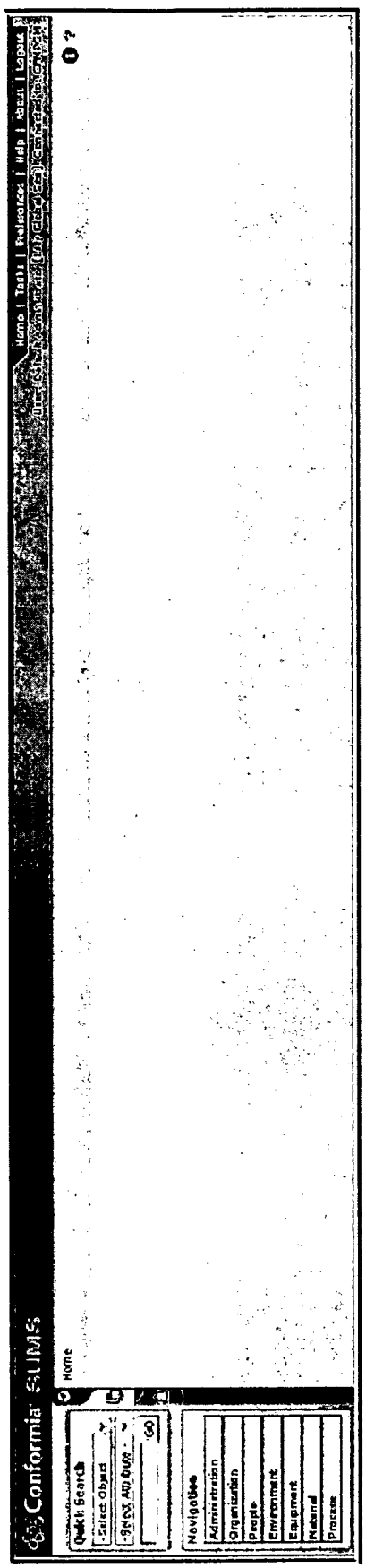
FIG. 19 illustrates a home page in accordance with an embodiment of the present invention.

The present invention provides a login page, a home page, standardized icons, search functionality, bread crumbs and process steps, a result table container, a table container with sub-tabs, a review page, and an action confirmation manager. The login page is provided in FIG. 18. To login, a user provides a user ID and password and clicks login. Referring to FIG. 19, after logging in, the home page is provided. The home page is divided into two panes. The left pane displays the quick search and the navigation bar. On the right hand side pane, the following tables or channels are provided: open tasks, projects, and campaigns. These channels can be shown/hidden according to user preferences. Apart from these, the user can find menu and alerts manager icons on the intersection of the two panes. Under quick search, a drop down allows the user to select a user name or user ID to search on and then proceed with the search by clicking "go". Under navigation, the user can view the SUMS's functional modules in the navigation bar: administration, organization, people, environment, equipment, material, and process. In some embodiments, a user can view only those functional modules for which permission has been granted. For example, in some installations, an equipment manager can see the equipment tab, but not the material tab. Clicking on any one of these takes you to the respective category. The main functionality of each of these bars is listed below:

| MODULE | CORE FUNCTIONALITY |
| --- | --- |
| Administration | System Administration is done here: creating alerts, workflows, meta models (adding attributes to categories). |
| Organization | Setting up company structure, departments, location, sites. |
| Environment | Setting up new conditions such as maximum and minimum temperatures, pressures, humidity. etc. |
| People | Adding new contacts, roles, users, and user groups. |
| Reporting | Creating and linking to reports. |
| Equipment | Adding and managing equipment. |
| Material | Adding and managing materials. |
| Process | Creating and Managing: Projects, Campaigns, Process Steps, Batch Records. |

Figure 20:
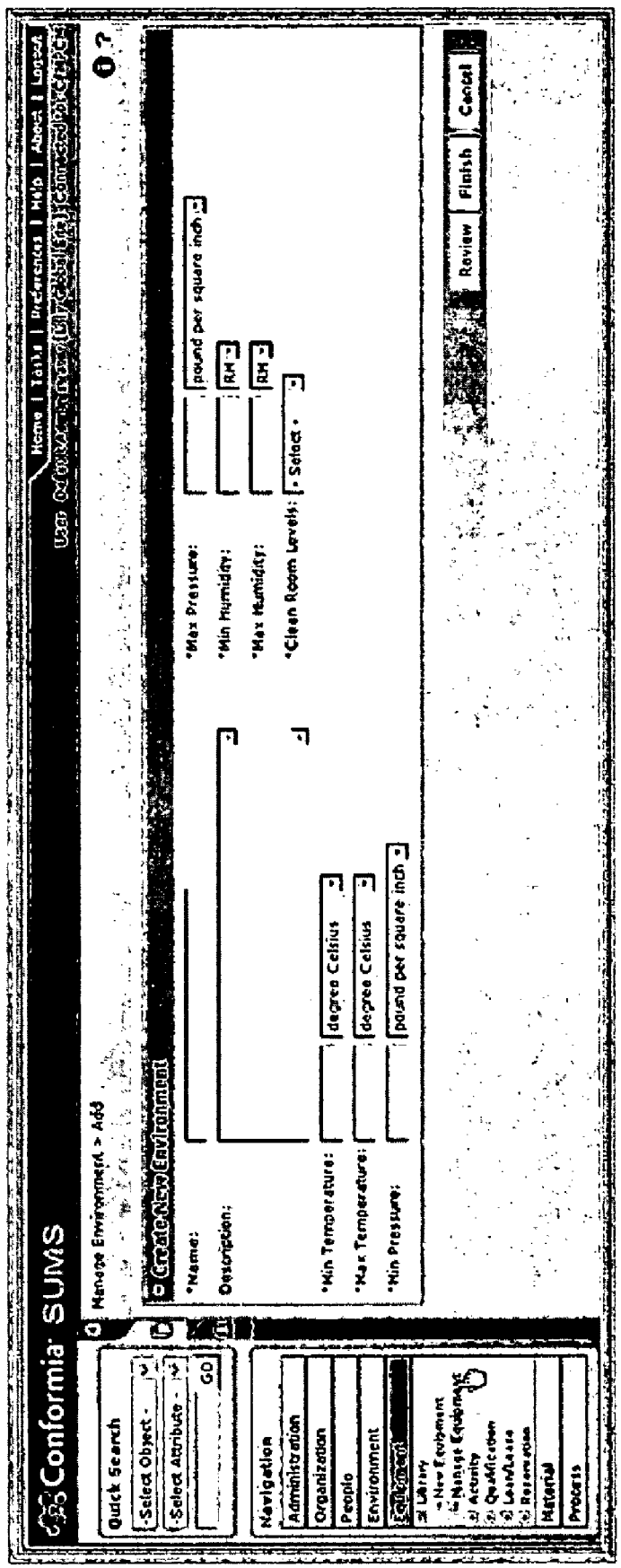
FIG. 20 illustrates a new equipment page in accordance with an embodiment of the present invention.

For example, as discussed, by clicking on the navigation bar: equipment bar, under Equipment, a user will now see library and manage equipment. Referring to FIG. 20, by clicking on new equipment, a user can add new equipment. A screen is provided that will allow a user to organize the equipment already entered into the system or add new equipment.

Figure 22:
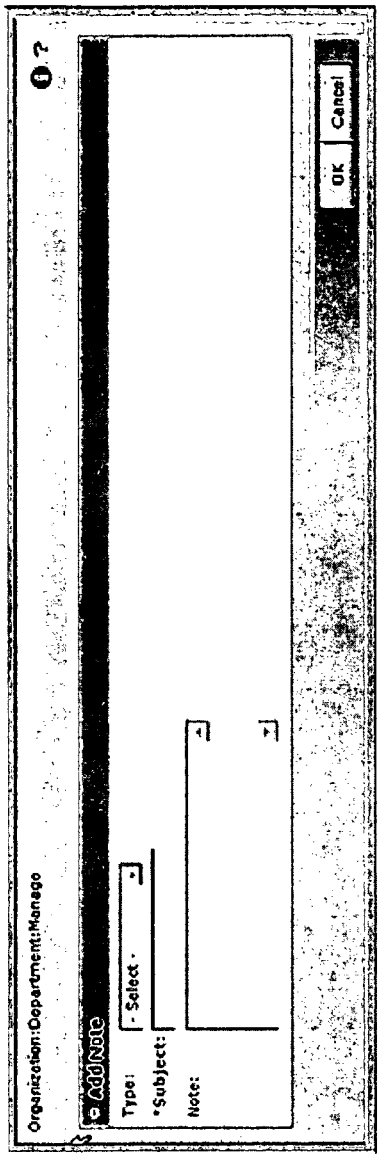
FIG. 22 illustrate an add notes pane in accordance with an embodiment of the present invention.
Figure 23:
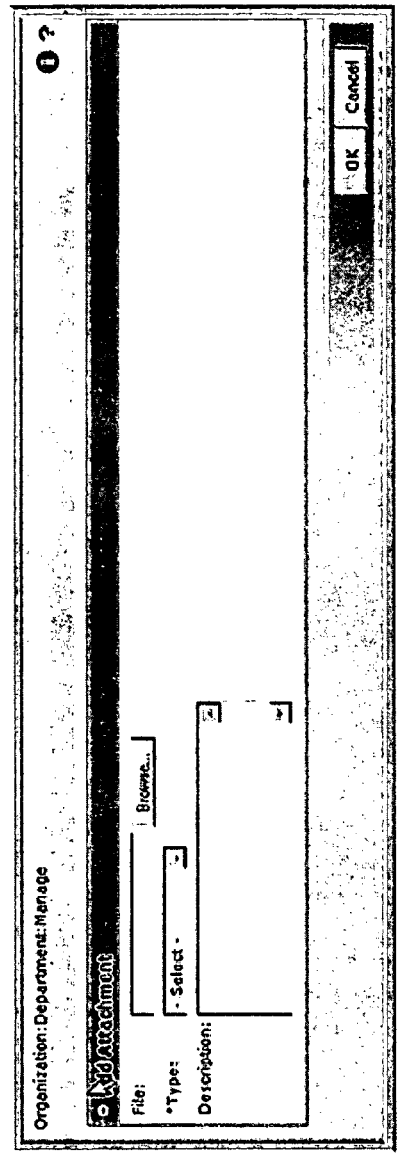
FIG. 23 illustrates an the add attachment panel in accordance with an embodiment of the present invention.

Some embodiments of the present invention include, but are not limited to the following icons: expand and lookup icons, alert icons, comparison icons, notes icons, and attachment icons. These icons are used across SUMS for various purposes. The menu icon takes a user to the standard navigation bars: administration, organization, people, etc. Clicking on the alert icon displays all the user's alerts. The Compare icon allows a user to compare records in the search results page. On clicking this icon, the compare records page displays the screen depicted in FIG. 21. The compare records page comprises three columns: the first column displays the attribute names, the second column displays the attributes of the record selected, and the third column displays the attributes the user wants to compare. The add notes icon, allows a user to add notes to a record on the search results page. On clicking this icon, the add notes page displays the pane illustrated in FIG. 22. The add attachment icon is used to attach a file of any type to a record on the search results page. On clicking this icon, the add attachment page displays the panel illustrated in FIG. 23.

Search and results page. SUMS provides an effective search mechanism. The user may design custom search views which will provide a wide range of search criterion to choose from. Regular expressions can also be specified as search expressions. These expressions are compliant with the IEEE POSIX regular expression standard. The table below shows the meta-characters that can be used and a short explanation of their meanings:

| Meta character | Description |
| --- | --- |
| * | Matches zero or more occurrences of the character immediately preceding. |
| + | Matches one or more occurrences of the character immediately preceding. |
| ? | Matches zero or one occurrence of the character immediately preceding. |
| \ | Use \ to treat the following character as an ordinary character. |

When performing a search, a user can view the search results in the results frame at the bottom section of the page. The user may also save the search parameters by clicking "save search". A user may recall theses searches at a later point of time, by clicking "load search" and selecting the required search parameter. Also, if user wants to further narrow down the scope of search, then on the results screen, the filter icon can be clicked the fields with appropriate values can be and entered and selected. The user can also choose the number of records to be displayed on the results screen by selecting the required number from the drop down menu of "results per page."

With the appropriate rights, a user can create create/modify/remove/duplicate views for a company, project . . . etc. or any category. Every view has searchable attributes and result attributes associated with it. Search screens could be rendered based on the searchable attributes and results screen could display values only for result attributes. However, specifying search criteria can perform search using all the result attributes as well. A user can select a record in the results page and then click on any of action button to perform actions like add, edit, duplicate etc. A user can sort each column of data on the results page in alphabetical or ascending/descending order by clicking on the column header.

After proceeding through a number of steps, in most cases the user will be presented with final review page. It's a way to look over and confirm all the steps before entering the data into SUMS. If a mistake has been made or changes to some data previously entered is desired, the user will usually be given the option to cancel or to click on a previous button.

Material Management Module

Figure 6:
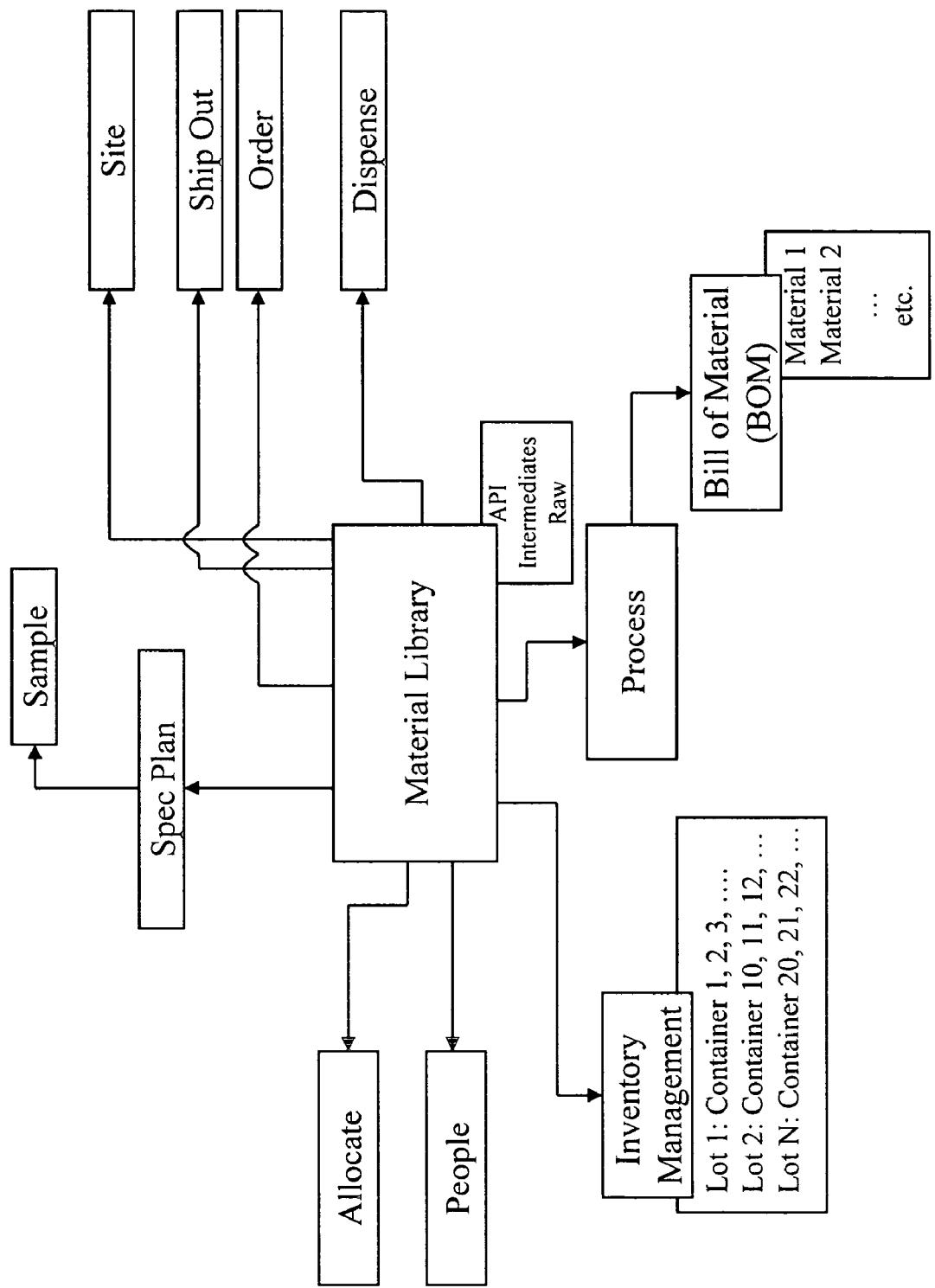
FIG. 6 illustrates a material management module.
Figure 7:
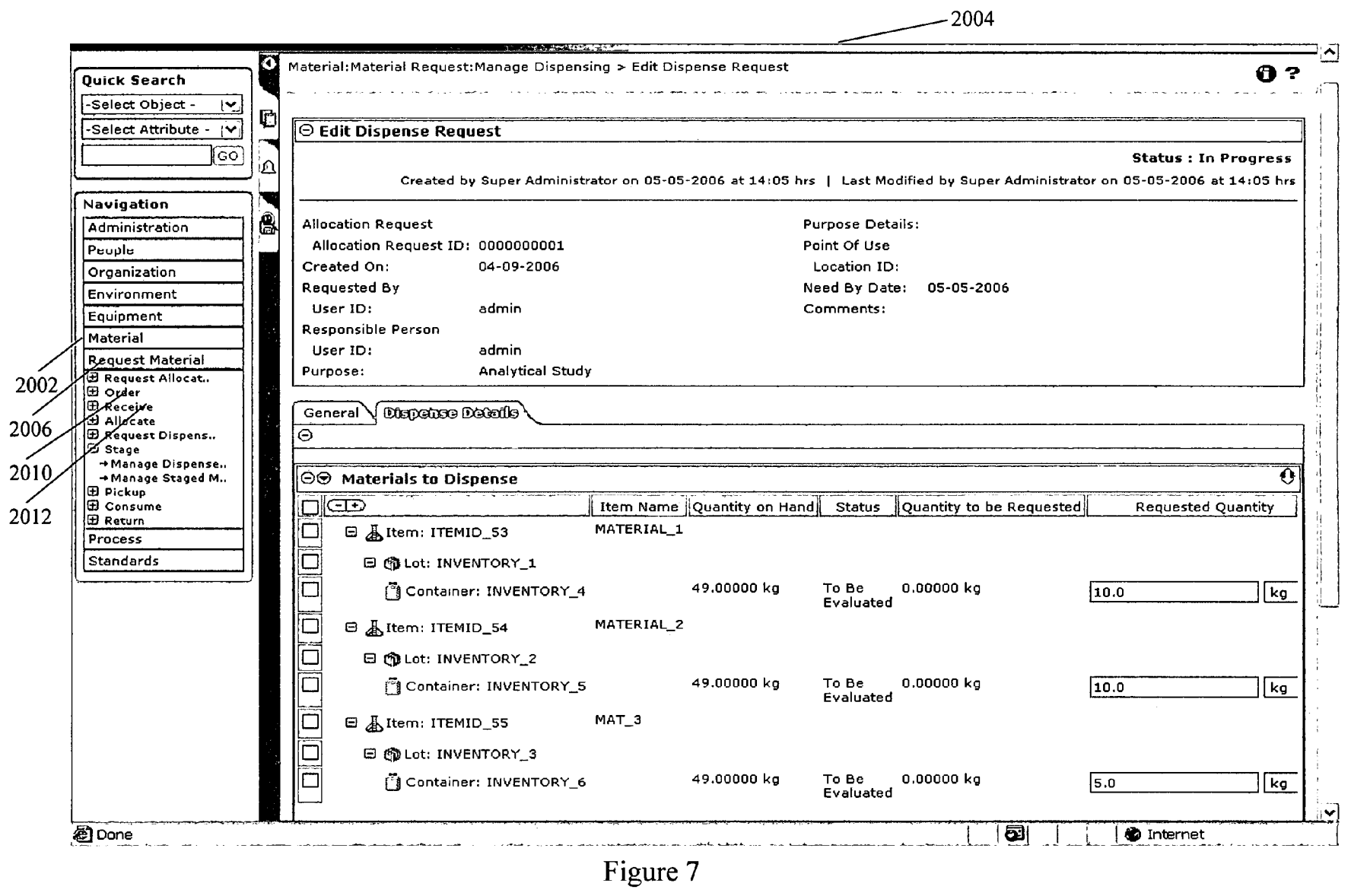

Advantageously, the present invention provides an enhanced inventory management module 100 termed a material management module 2000. In some embodiments, material management module 2000 provides the following services: adding material into inventory, managing the material inventory, tracking the movement and storage of material throughout a warehouse, checking material availability, allocating inventory by requirement, ordering material from vendors and other sites, managing the suppliers or vendors, managing ordering and receiving of materials, managing material dispensing and consumption, and setup and management of specification plans on material. FIG. 6 illustrates the interdependencies of various elements of core module 1000 with elements in material management module 2000. Referring to FIG. 7, in some embodiments, material management module 2000 can be accessed by material tab 2002 of screen 2004.

Material management module 2000 manages the material's inventory of lots and their associated containers. Material management module 2000 allows a user to monitor inventory levels, trigger restock levels, adjust inventory, dispose unwanted material, locate tracking and lot release status, track material usage, check retest and expiration dates, and check required lot documentation.

In some embodiments, material management module 2000 provides functionality for searching for a lot, searching for a container, searching for inventory disposals, searching for lots by allocation made on them, and searching for lots that require retesting.

Searching for a lot. A user can search by material category, common name, item id, compound number, item code, lot number, site, contact person and lot status. To view all lots, a user clicks on a Search button with out entering any search criteria. Wildcard characters are also accepted. On the Results page, the material and its corresponding lots are listed under each item with details like lot number, material name, item ID, item code, material type, quantity on hand, operating mode, contact person, site and lot status. In some embodiments, the results page has action buttons that let a user edit the material details, print label, create allocation request, adjust quantity, order a material, quarantine a lot, initiate material disposal, add material to inventory, re-allocate a material, move a material from one location to another and set the inventory restock limit for a given site.

Searching for a container. A user can search for a container by entering an item name in a "Locate Container" search view. A user would see the "Locate Container" view by clicking on the view pull down box located on the top right hand corner of the "Manage Inventory" screen. A user can also search by material category, common name, item id, compound number, item code, container number, operating mode, site, and storage location. The "Results" page displays details like container number, the corresponding lot number, material name, item id, item code, operating mode, storage location and site. On the "Results" page, there are action buttons that permit a user to edit the material details, print label, create allocation request, adjust quantity, order a material, quarantine a lot, initiate material disposal, add material to inventory, re-allocate a material, move a material from one location to another and set the inventory restock limit for a given site.

Searching for inventory disposals. A user can search for a material lot that is to be disposed on an "Inventory Disposal Search" screen. In some embodiments, a user clicks on a view pull down box located on the top right hand corner of a "Manage Inventory" screen to see an "Inventory Disposal" search option. The user can search by material name, item id, item code, lot number, container number, actual disposal range, and planned disposal date range, disposal status, disposal method, and waste stream identification, site of disposal or by the user who carried out the disposal operation. The result screen lets the user plan a disposal operation and dispose a lot.

Searching for lots requiring retests. A user can locate a lot that requires retesting by entering a material name in a "Lot Request Retest" search view. A Lot Request Retest view is visualized, in some embodiments, by clicking on the view pull down box located on the top right hand corner of a "Manage Inventory" screen. A user can search by item code, lot number, and test date. A "Result" page will display details like material name, item code, lot number, test type, test name, and re-test date. In some embodiments, on the Results page, there are action buttons that let a user edit the material details, print label, create allocation request, adjust quantity, order a material, to do peroxide testing on material, quarantine a lot, initiate material plan disposal, add material to inventory, de-allocate a material, move a material from one location to another and set the site requirement.

View inventory details. A default view in a "Manage Inventory" page allows a user to locate and view inventory details.

In some embodiments, the first half of the page lists information like lot number, lot status, operating mode, material category, material type, material name, common name, item id, item code, compound number, and contact person. In some embodiments, the second half of the "Lot Details" page provides tabs that display following details corresponding to the selected lot: general details, history, container details, and evaluations done on the lot. The details tab displays general details associated with the container like original quantity, quantity on hand, available quantity, date of receipt, container type, container size, etc. A container tab displays the details of the associated container. A history tab displays sub-tabs such as allocation, disposal, peroxide forming, adjustment history, and usage history. An allocation tab displays allocation details such as, allocated person, allocated quantity, project id, project name, project target molecule, campaign name, and requested material name. A disposal tab display details such as actual disposal date, quantity disposed, disposal method, waste stream id, site of disposal, and comments. An adjustment history tab: displays details such as adjustment id, adjustment date, container id, quantity adjusted, adjusted by, and reason for adjustment. A usage history tab displays details such as, dispense id, dispense request status, container id, quantity, transaction date, project, target molecule, and comments. A peroxide forming tab displays details such as next retest date, test result, test date, approved on, and identity of person granting approval. An evaluation tab displays evaluation details such as re-evaluation date, request Id, specification plan id, specification plan name, and requestor View lot details. A view lot details page provides all the information associated with a lot. In some embodiments, a first half of the page lists information like lot number, lot status, operating mode, material category, material type, material name, common name, item id, item code, compound number and contact person. In some embodiments, a second half of the lot details page provides tabs that display details corresponding to the selected lot such as general details, history, container details, and evaluations done on the lot. For example, a details tab displays general details associated with the container like original quantity, quantity on hand, available quantity, date of receipt, container type, container size, etc. A container tab displays the details of the associated container. A history tab displays detailed history of allocations, adjustments, disposals, peroxide formation test done and usage of the selected lot. The history tab can display sub tabs such as allocation, disposal, peroxide forming, adjustment history, and usage history. The allocation tab displays allocation details such as, allocated person, allocated quantity, project id, project name, project target molecule, campaign name, and requested material name. The disposal tab displays details such as, actual disposal date, quantity disposed, disposal method, waste stream id, site of disposal, and comments. The adjustment history tab displays details such as adjustment id, adjustment date, container id, quantity adjusted, adjusted by, and reason for adjustment. The usage history tab displays details such as, dispense id, dispense request status, container id, quantity, transaction date, project, target molecule, and comments. The peroxide forming tab displays details such as, next retest date, test result, test date, approved on, and person granting approval. An evaluation tab displays evaluation details like re-evaluation date, request id, specification plan id, specification plan name, and requester.

View associated containers. To view details of all containers associated with a lot, in some embodiments, a "Lot Details" page is provided with a "Containers tab." In some embodiments, when this tab is selected, the system will display number of containers, quantity on hand (total number of containers associated with the lot), quantity allocated, quantity available, storage location, and date of receipt.

View specification plans by lot. In some embodiments, specification plans have a re-evaluation period before which time one must retest a lot again for the specification plan. Multiple specification plans can be associated to a lot. In some embodiments, an "Evaluation tab" on a "Details page" leads to the display of the specification plans that has been evaluated against each lot. In some embodiments, the specific details that are displayed on the page include: re-evaluation date, request id, specification plan id, specification plan name, and requester.

View peroxide forming history. In some embodiments, the test history of a lot that is associated with a peroxide forming chemical material (material that is flagged 'Peroxide Forming'=Yes), is viewed by clicking on a "History tab" of a "Details page." When this is done, details such as next retest date, test result, test date, approved on and approver are provided.

View container details. In some embodiments, a "container details" page has informational tabs such as "Details", "History", and "Evaluation." The details tab displays general details associated with the container like original quantity, quantity on hand, available quantity, date of receipt, container type, container size, etc. The history tab displays detailed history of allocations, adjustments, disposals and usage of the material at container level. The evaluation tab displays the specification plan that has been evaluated against each container.

Alerts associated with material inventory. Advantageously, the system allows a user to configure custom alerts that will suit custom requirements. However, in some embodiments, there are four default alerts that are triggered at various stage of inventory processing: (i) lot/container quarantined alert, (ii) expiration alert, (iii) exceed adjustment threshold limit alert, and (iv) restock limit alert. The lot container quarantined alert is a mandatory alert that the system sends to the quality controller and the material manager(and other affected users) when a lot or container has been quarantined. The alert message will contain the details like lot number, quarantined date, quarantined by and reason for quarantining. If an entire lot has been quarantined, the alert message displays the lot number. If only a container has been quarantined, then the container and its associating lot are displayed in the alert message. The expiration alert is a mandatory alert that gets triggered on the expiration date of a lot. The message is sent to the "Material Manager" with details like lot number, material name, item id and expiration date. The exceed adjustment threshold limit alert gets triggered when the inventory adjustment exceeds the adjustment threshold limit. The alert message will contain details of the lot that has exceeded the inventory adjustment threshold which includes lot number, material name, item ID, adjustment threshold limit, adjustment ID, adjustment quantity, adjusted by and reason for adjustment. This alert is mandatory. The restock limit alert is a mandatory alert that is triggered to warn the material manager that the inventory needs to be restocked. The alert triggers off when "quantity on hand" of a material at a site becomes equal to the restock limit. The alert message will contain the details of the material to be restocked like the material name, common name, item ID, item code, restock limit and quantity on hand.

Quarantine a lot/container. The present invention provides procedures for quarantining incoming received material lots. Once a lot is under quarantine, the comprising containers are also quarantined automatically. Lots in "Quarantined" status cannot be used up in a GMP process. Advantageously, once a lot or container is quarantined, the system will prevent any users from dispensing the lot/container until they are released from quarantine. If the material is already dispensed before the quarantine effective date, it can be consumed. Otherwise, it cannot be consumed. Quarantine effective date is the date from which the material is quarantined. This date can be current or past date, but cannot be a future date. Allocation is allowed on quarantined materials. Any lot that has "Quantity on hand" greater than zero can be quarantined. In some embodiments, each time a lot or container is quarantined, the present invention sends an alert message to the material manager and the quality controller.

Monitor inventory level. The present invention allows for the monitoring of material inventory level at site level and ensures that the material doesn't fall below the restock levels. A user verifies that the material is always stocked at a required minimum level. In some embodiments, if inventory level falls below restock limit, a mandatory alert is triggered to warn the "Material Manager" that the inventory needs to be restocked. The alert message will contain the details of the material to be restocked like the material name, common name, item ID, item code, and restock limit and quantity on hand.

Adjust material inventory. The inventory can be adjusted in the system if the Quantity on Hand is not matching what is present in the system (Quantity Available). There is a threshold limit up to which a user can adjust the inventory. This Inventory Adjustment Threshold is calculated in percentage. If the user exceeds this limit while adjusting the inventory, the system will send an alert to the material managers and other subscribers. At this point, the system will reset the value of "total quantity adjusted to zero." Also, the adjustments requested are applied to the lots/container simultaneously. Low inventory level is the lowest stock limit. If the quantity on hand goes below the low inventory level, the material manager will get an alert to restock the inventory.

Dispose inventory. Disposing a material involves two steps: plan the disposal (specify the date of disposing, site of disposal etc.) and dispose the lot/container. Once a lot/container has been disposed, the system resets or decrements the inventory for the container and also changes the "Site for the Container" to the "Disposal Site." Inventory disposal is planed by entering the disposal date, and reason for disposal. The user may select one or many lots/containers and enter a planned disposal date. Once lots/containers are selected for disposal, the system changes the "Disposal Status" of these selected lots/containers to "Planned". When a user plans for lot or container disposal, the people associated with the inventory planned for disposal get a workflow task lined up in their tasks list for them to take some action. Each such person is termed a 'Contact Person' for the lot and anyone else that has been allocated to the inventory. The "Contact Person" and the people allocated to the inventory can confirm or reject the respective lots/containers associated with them. If the contact person and the allocated people accept their respective planned lots for disposal, the system automatically changes the Disposal Status to "Confirm". Once the disposal plan is in "Confirm" status, the user can go ahead and dispose the material. A disposal plan can contain one lot/container, or multiple lots/containers of different materials. For each planned group disposal, the following information can be recorded against the inventory: actual disposal date, quantity disposed, disposal method, waste stream identification, site of disposal, disposer, and comments. The system records this information against each lot/container, as the case may be. When the user has selected a lot for disposal, only the containers that are in inventory will be disposed. Containers currently out of inventory will not be affected by the disposal plan. Once a lot/container has been disposed, the system resets or decrements the inventory for the container and also changes the "Site for the Container" to the disposal site. In some embodiments, the system decrements a material's quantity from the inventory in four situations: (i) when a material is consumed for a process, (ii) when the material is dispensed to another plant/or for consumption, (iii) when the material is disposed, (iv) when the material is allocated. If the quantity of a container is zero, the system does not show this container for any search results except when a user specifically wants to see containers of zero quantity.

Inventory operating mode. The present invention allows a user to indicate the mode of operation for each lot or container received as GMP/Non-GMP. By default, a lot indicated with GMP (good manufacturing practice) mode will have containers flagged with GMP mode. If the inventory was produced in-house, the default operating mode would be what is specified for the campaign to produce the inventory. The system allows the user to modify operating mode form GMP to Non-GMP. However, it is not possible to modify operating mode from Non-GMP to GMP. A container operating mode overrides the lot operating mode. For example, a container can be dispensed/handled in non-GMP standard, which will change the container from GMP to non-GMP.

Set site requirements. A user will need to define and maintain the stock levels for materials in various sites from time to time. The user can select one or more sites and set the requirements by entering the following information: restock limit, quantity adjustment threshold, and low inventory threshold Modify a group of containers. In some embodiments, a user can modify attributes of containers either individually or as group, related to the same lot. In some embodiments, a user can make changes to the following container attributes: manufacturing operation mode, container location, container type, container size, material of construction, container gross weight, and container tare weight.

Lots—modify a lot. In some embodiments, a user can modify some attributes of a lot like contact person, manufacturer name, manufacturer site, manufactured date, expiration date, COA, TSE, certificate, crystal form, import status, stability flag, reason not on stability etc. In addition to these, if the user has some user-defined attributes, these can be edited as well.

Peroxide testing. While adding a material to the system inventory, a user may specify whether it is susceptible to peroxide formation by setting the flag Peroxide Forming=Yes. If it is, the user may want to do peroxide testing on the material. After the required tests on the material have been conducted, details of such tests are entered into the system. A user may select one or many lots/container associated with a material and globally update peroxide testing information by entering the following details such as: test name, test date, test result, next retest date, approved on, approved by, and comments.

Containers—modifying a container. A user can change the details pertaining to a container like the container site, storage location, operating mode, container type, container size, material of construction, gross weight, tare weight and storage location. Every time a user modifies a container, a user is prompted to enter the reason for modification and this information along with user name, date, and time of this action will be recorded as part of the audit trail.

Containers—add container while modifying lot. A user can add a container to an existing lot in the system. The container status will be lot status by default at the time of creation. However, the system allows the user to change status. While adding a container, the user needs to provide values for the following attributes: manufacturing operating mode, container location, container type, container size, material of construction, container gross weight, and container tare weight.

Figure 8:
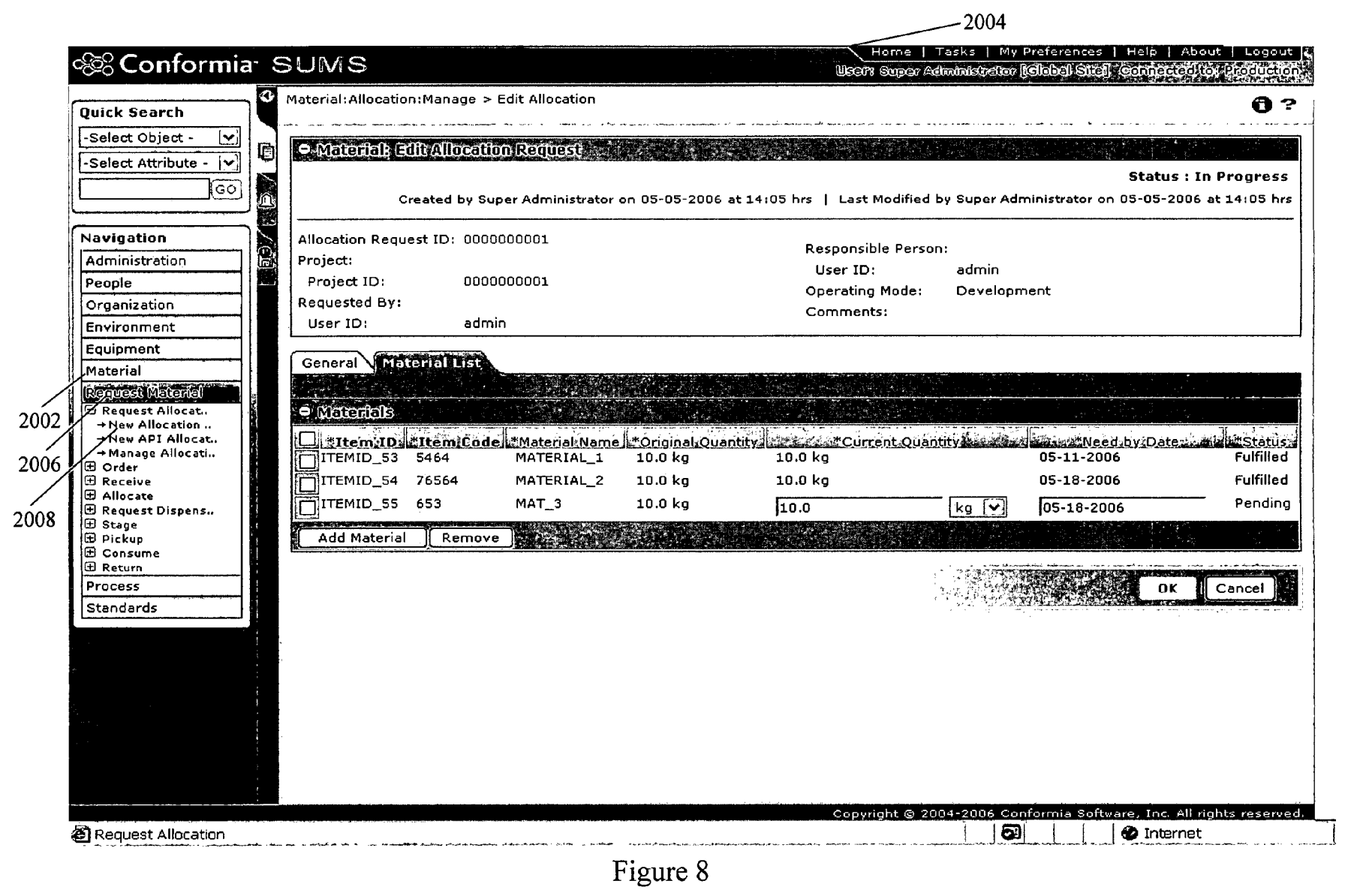
Figure 9:
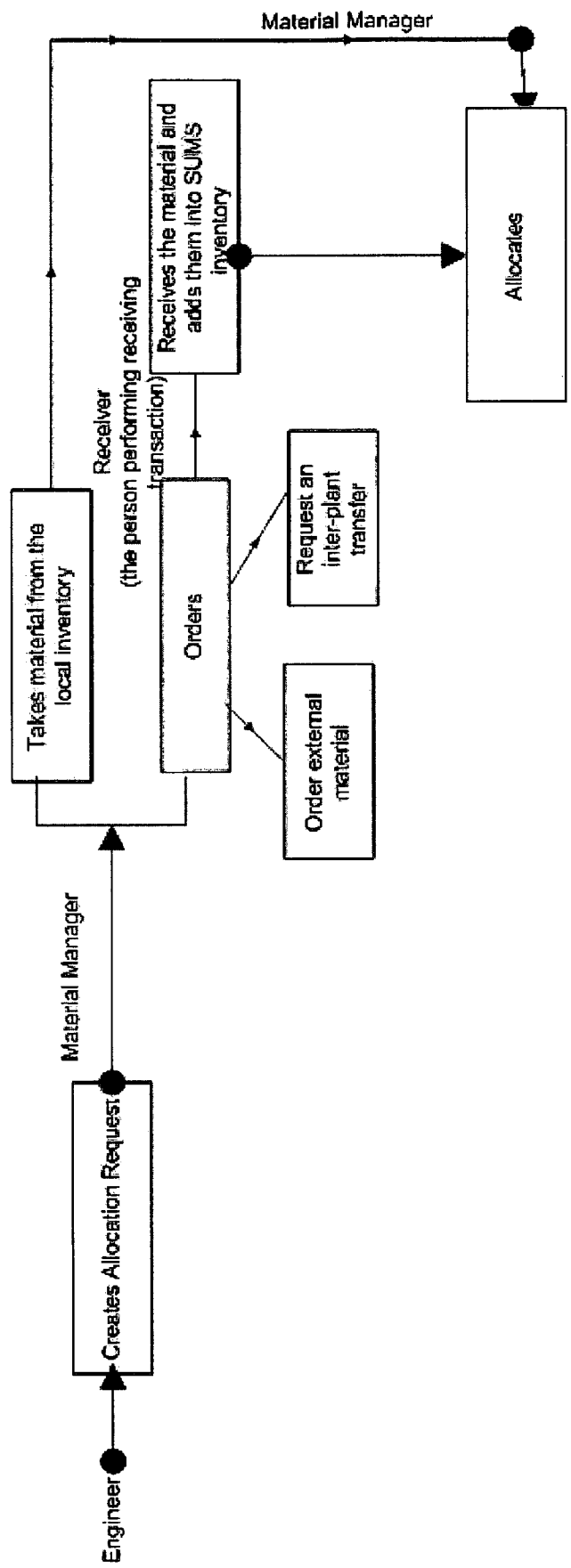
FIG. 9 depicts an allocation process in accordance with an embodiment of the present invention.

Create allocation request from inventory. When a user requires a material for a project, the user can send an allocation request to the material manager. In some embodiments, this is accomplished through request allocation tab 2006 of panel 2004 as illustrated in FIG. 7. Specifically, referring to FIG. 8, a user can select "New Allocation" tab 2008. The material manager can either allocate the requested material from the inventory if it is available or the user can purchase the material through an external vendor or do an inter-plant transfer. Such transactions are called ordering or sourcing. Once the material manager receives the ordered material, the user can allocate the material to the request. Hence, allocation process involves: creating an allocation request, modifying and canceling it. Methods for sourcing the material to fulfill the allocation request include, but are not limited to, purchasing material through external vendor, inter-plant transfer, allocating from existing inventory, locating allocation requests, and de-allocating the material. FIG. 9 depicts an allocation process in accordance with an embodiment of the present invention.

Search for an allocation request. The system lets users search for an allocation request through various search views such as basic, default, and allocation line item. Each of these screens has a different set of field values that from which the can enter a search criterion. Apart from these available views, the user can create custom views for the allocation request object. The basic search view allows a user to search for all the immediate details of interest about an allocation request. The user could also search by allocation request ID, status (of allocation request), requester, responsible person, project etc. The results page display information such as allocation request ID, requester, responsible person, project ID, process step name, operating mode, status (of allocation request), creator, and creation date. The default search view helps a user search for an allocation request by the associated Campaign, process step or project names. The default view is created by the system automatically, when the user creates the category. Hence, the default view will display all the attributes associated with the association category and the list of attributes will change as the data model changes. The user can select any of the views on the search screen to run a search. In some embodiments, there are action buttons on the results page that let the user create a new allocation request, edit an allocation request, view allocation status, allocate/de-allocate a material and, or place a new order from an allocation request. Some of the action buttons mentioned above will appear/disappear on the screen, depending upon the role the user has been assigned.

Search an allocation line item. In some instances, the user wants to search for details of the line items in an allocation request. In such embodiments, the user can search for allocation request line item by selecting Manage Allocation Request. On this page, a view pull down box, on the top right hand corner, provides a "Allocation Line Item" search screen. Searching from this screen allows a user to find all the line items and their details that comprises the specified allocation request, all the materials requested to be allocated by a specified user, all requested material that are under the responsibility of a specified user, all requested line items under a specified project, all details of a line item like the associated Allocation Request ID, requested by user, associated project, status and quantity requested, all line items that are in a particular status, etc. . Entry of any of the following as search criteria will get the above mentioned results: allocation request ID, quantity requested, quantity allocated, quantity ordered, quantity not sourced, requested by, responsible person, project, and material. The results view shows two subviews - 'Basic' and 'Summary'.

Alerts associated with allocation. In some embodiments, there are two alerts that are configured in the system which correspond to allocation activities. They are "line item allocated alert," and "deallocate alert." The line item allocated alert is a non-mandatory alert that is sent when a line item in an allocation request is fulfilled. The subject line will say "Material Allocated". In some embodiments, the following details will be enlisted in the body of the alert message, allocation request id, material item code, material name, quantity allocated, allocated on and allocator. The deallocate alert is a non-mandatory alert that gets triggered when a material is deallocated from an allocated list. The alert will carry a subject line that says "Material Deallocated". In some embodiments, the message body will contain the details such as allocation request id, material item code, material name, quantity deallocated, deallocated on, deallocated by, and new quantity allocated.

Request allocation. A user may make a request for a material by creating an Ad-hoc allocation request or creating an allocation requests from scaled, planned or production BOM. An allocation request can be saved in draft and submitted later. A user may create allocation requests for API or Non API substance or for a mix of both. But, in typical embodiments, a user cannot create allocation requests for expendable material. An adhoc allocation request is useful when the user has not figured out which specific batch record where the material is going to be consumed but still wants a list of material to be allocated for the project. The system prompts the user to enter the corresponding project name when creating an adhoc allocation request. There are three steps to create an adhoc allocation request: selecting the project, selecting material(s) against which the allocation request have to created, specifying the quantity and need by date against each item. In some embodiments, all materials that are added to the allocation request have to exist in the material library. A user cannot not specify the lots or containers at the time of creation an allocation request. In some embodiments, not all users have the right to create an allocation request. Typically a user needs to be an engineer, chemist or material manager to be able to access the screens for creating an allocation request.

A workflow gets triggered when a user creates an allocation request. A newly created allocation request is in the draft state. Allocation requests cannot be fulfilled until the request is in the submitted state. The final screen of create allocation request (viz, e.g. an action complete screen) allows a user to take action on the workflow state. The user can take action that will submit/cancel the allocation request or stop the associated workflow. The status of an allocation request is closely dependent on the associated workflow. An allocation request can assume any of the below status as the workflow transitions ahead: draft, submitted, in progress, completed, and cancelled. A newly created allocation request is in the draft state. A user cannot allocate any line items in this request, until it moves to the submitted state. The allocation request is in the "submitted" state when the user submits an allocation request through workflow task. When any requested line item in the allocation request is allocated, the status of the request becomes "In Progress". An allocation request goes to "Completed" status as soon as all the comprising line item are in "Fulfilled" state. When the user cancels an allocation request, it goes to "Cancelled" state. The status of the comprising material line items in an allocation request affects the status of the allocation request itself.

In some embodiments, an allocation request line item can have the following status: requested, pending, and fulfilled. When a user creates a new allocation request, the line items that comprises the allocation request are in the requested state, by default. When a line item is partially allocated it will be in the "pending" state. When the 'allocated quantity' of the line item=or is greater than 'current requested quantity', it will move to "fulfilled" status. If a user has the appropriate rights, the user may create an allocation request for an API substance. The system will display a list of API substance from which the user can select the line items for the request.

Request allocations from bill of material (BOM). Different materials are consumed at different stages of the production cycle. The user may want to use different raw materials, intermediates etc at various stages of a project. In some embodiments, the system allows the user to create material allocation requests from three various stages of development of a project—when specifying a scaled BOM, planned BOM or production BOM. The user can pick one or more from the listed materials on the scaled BOM and create an allocation request for the same. The quantity requested will be defaulted to the quantity of material from BOM.

Modify an allocation request. Editing an allocation request primarily allows a user to add or remove line items from the request. In some embodiments, the allocation request has to be in the draft state in order for the user to edit it and add/remove line items from it. If "Allocation Request" is in submitted or in progress status, then only the line item, whose status is not 'fulfilled' can be edited. In some embodiments, the allocation request should not be in Completed or Cancelled status in order to be edited. A user can update the current requested quantity and need by date, but the original requested quantity will not be updated.

Cancel an allocation request. In some embodiments, to reject an allocation request, a user must make sure that all the line items in the allocation request are in Pending or in "Requested" status. In preferred embodiments, a user must have the appropriate privileges to cancel an allocation request. The user may cancel only one request at a time. The line items in the allocation request that have already been allocated will not be affected by the cancellation of the enclosing allocation request. In some embodiments, the material manager can deallocate quantities from a cancelled allocation request and use them to fulfill other active allocation requests, but allocations are not allowed on the line items in the cancelled allocation request.

Duplicate an allocation request. In some embodiments, duplicating an allocation request is the fastest way to create a new allocation request from an existing request. The newly created allocation request will have a new request Id. The user can associate this new allocation request to a new project and assign a new responsible person. The user can also add or remove the materials that comprises the request. The system will prompt the user to enter the reason for duplication which will be recorded for audit purposes. An allocation request can be duplicated irrespective of its status. All the comprising material of the original request will be duplicated as part of the duplication process. A duplicated allocation request is in the draft status and status of line items will become "requested" only after the request is submitted.

Allocate a material. When an allocation request is to be fulfilled, a user may want to allocate material from the existing inventory or allocate from the inventory. Allocations are usually carried out by the material manager or the allocations manager. As the first step, the manager searches for the allocation request that is to be fulfilled, selects the items in the request and clicks "allocate." For each selected allocation line item, the system will display the lots/containers which has quantity on hand greater than zero on the Material:Allocate screen. The allocation id, comprising line items, lots and the associated containers are all displayed as a hierarchical tree with the container at the lowest level on this screen. The user may check the quantity on hand, quantity allocated and quantity available for each container before fulfilling the request. The user fulfills an allocation request at the container level. By default, the system will allow the allocation manager or the person performing fulfillment to select only those allocation requests that have been created in the same site as the fulfilling user's logged in site. Thus, the allocations manager from one site cannot allocate requests for material in another site. However, this rule does not apply, if the user is a super user. For each allocation request line item, if the allocated quantity is equal or greater than the "current requested quantity", then the status of the allocation request line item becomes "fulfilled". The requested line items can be completely fulfilled or partially fulfilled depending on the quantity allocated. The partially allocated line item will be in "pending" status and the partially fulfilled allocation request will be "in progress". Each time a user allocates a material from the inventory, the corresponding inventory quantity will be updated. Once an allocation is completed for a line item, the system updates its status to "fulfilled".

Deallocate a material. To fulfill a critical request for a material that is not immediately available in inventory, a user may want to free up that material from another existing allocation request. This happens through the process of deallocation. In some embodiments, on a deallocation screen, the program displays the available quantity (Qty on Hand-Quantity Allocated) for all the containers of a selected allocation request line item from which the user can decide on the quantity to be deallocated for each. Once a container is deallocated from an allocated material list, an alert is sent to the affected people. Also, the available quantity for the lot/container is updated accordingly, thus freeing up some more material from the allocated list which a user may in turn allocate to another user. Even after a lot or container is relieved from an allocated list, the system maintains a log of previous owner & project assigned to the lot/container which is viewable through the allocations history tab. In some embodiments, only those materials in an allocation request whose status is "completed" can be deallocated. Deallocation cannot be done on allocation requests that are in the draft or submitted state.

View allocation details. Important information corresponding to an allocation request is displayed on the view details page. In some embodiments, this page has four tabs apart from the header section: requested material, allocated material, allocation status. In some embodiments, on the top header section of the details page, information such as allocation request ID, project, requested by, responsible person, operating mode, and comments. By default, the requested material tab is highlighted. Under requested material, a user will see the over all details of the requested material like: item ID, item code, material name, and quantity requested. Clicking on allocated material tab affords a view status of each allocated line item comprising the selected allocation request like: material name, quantity on hand, quantity allocated, and status with in allocation request. This tab will be disabled if the selected allocation request has no fulfilled allocations. By clicking allocation status tab, the user will view line item status, dispense details by material consumed, and dispense details by material returned. The screen will have different values depending on when the allocation request is adhoc or made from scaled/planned/production BOM.

Allocated material. An allocation request might be in draft state, partially fulfilled or completely fulfilled at a given point of time. A user can check the current status of each line item in the request in order to know the state of each requested material. In some embodiments, an "Allocated Material tab" on a "Details page" displays the status of each allocated material in a request with respect to its lots and containers. On this screen, the user will see a tree view that depicts the material and the associated containers with the details like quantity on hand, quantity allocated and status of this material within the allocation request listed against each.

Allocation status. Viewing the current status of an allocation request is performed by locating the desired request, selecting it and clicking "View Allocation Status" in some embodiment. This action brings up a "View Allocation Status" page with the allocation status tab highlighted. The allocation status tab displays the complete comprehensive details about all stages associated with material allocation, right from requesting to consumption/return. The user may select at least any of the three detailed views on the allocation status tab to view: line item status, dispense details by material consumed, and dispense details by material returned. The line item status view displays the status of a line item in the request. Here, the user can review details like: status of each line item, quantity request against each line item, quantity of line item that is already sourced and the corresponding source ids, quantity not sourced, order id against each source id, and method of sourcing. The dispense details by material consumed view provides details of dispensed line items in the allocation request that are consumed. Here the user may view details such as dispense status, staging id, staged date, quantity staged, pick up id, pick up date, consume id, quantity consumed, and consumed date. The dispense details by material returned view provides details of dispensed line items in the allocation request that are returned. Here, the user may view details such as dispense status, staging id, staged date, quantity staged, pick up id, pick up date, return id, return date, and quantity returned.

Create orders from allocation request. If the requested quantity of materials in an allocation request is not available in the inventory, a user may want to place an order for those materials so that a user can fulfill the allocation request so that after they are received and entered into the program inventory, they can be used to fulfill the allocation request. The user may select one or more allocation requests at a time and place an order for the comprising line items. The program will prompt the user to enter ordered quantity per allocation request against each line item. For each material group of allocation request line items, the program sum up the total ordered quantity.

Ordering. When a user doesn't have a material in stock, or when there is an urgent allocation request for a particular material that is out of stock, the user can order it from an external vendor or do an inter-plant transfer. The order module in the program lets the user capture purchase or transfer order details. Referring to FIG. 8, a can: add details of a material order to an external vendor or by means of an inter-plant transfer, locate an order by its purchase order number, locate all the material purchased through a single order, modify an order, change the status and cancel an order, or remove an unused order from the user. Advantageously, the user can also create orders from an allocation request through a manage allocation screen. All data related to orders like purchase order number, orders Id, order type, order date, ordered by, expected arrival date, source site, number of items per order etc. is captured when a user adds a new order. Once an order is fulfilled, e.g., the order line items are received and entered into the program inventory, then the order status for the order line item will be updated by the program. All data related to orders like purchase order number, order Id, order type, order date, ordered by and expected arrival date is captured by the system. A user can also: locate an order, cancel an order, modify an order, or change the status of an order. Purchase orders are created when a user wants to replenish the inventory or when the user wants to fulfill an immediate allocation request. Hence, the program lets the user create adhoc orders from the main menu as well as from an allocation request. Creating a new order from the main menu is a two stepped process. First, a user enters the basic order information like the purchase order number, order type date, and user ID of the person who placed the order, expected arrival date and site from which the material is getting sourced. If it is an external order, the source site will be default working site of an affiliated supplier.

Next, the user searches and adds the material that is to be ordered. A newly created order will be in the Pending status.

If the requested quantity of materials in an allocation request is not available in the inventory, a user may want to place an order for those materials so that the user can fulfill the allocation request so that after they are received and entered into the program inventory, they can be used to fulfill the allocation request. The user may select one or more allocation requests at a time and place an order for the comprising line items. The program will prompt the user to enter ordered quantity per allocation request against each line item. For each material group of allocation request line items, the program would sum up the total ordered quantity.

Some embodiments of the present invention provide three different search views for locating an order: basic search, default search, and material details search. With administration rights, the user could design custom search and result views according to individual requirements. The default view is created by the program automatically, when the user create the categories. The user could run a basic search for an order entry by any of the following search criteria: order id, purchase order number, order type, status, ordered by, ordered date, expected arrival date, vendor, CAS number, and material name and the results page will list out the same details. The default search and results view will display all the attributes associated with order category. The material details search view is used to view details of line items in an order. This search results screen will display details like: item id, material name, order id, purchase order number, order type, total qty ordered, and total qty received.

Modifying an order. Once an order is placed, the user may go back and modify the order details. However, in some embodiments, only those orders in pending or in progress status can be edited. The order:edit screen mainly lets the user change the purchase order number, expected arrival date, source site, add or remove line items and the change total quantity of line items on the order. however, the user cannot modify the order id, order type and order date. On editing an in-progress order, the total ordered quantity for any material in the order cannot be set to be less than the already received quantity for that material. The user can also add notes and attachments to the order on the edit screen.

Cancel an order. If the user have placed an order which the user would like to cancel, the user can do it through, for example, a special manage screen. A cancelled order cannot be re used again. Only "pending" orders can be cancelled. Orders that are "completed" or "in progress" cannot be cancelled.

Set order status. In some embodiments, each time a received item is entered into the program, the corresponding order status also gets updated. An order can be in any of the following status: pending, in progress, completed, or cancelled. When pending, the order is created, but no line items have been received. When in progress, at least some quantity of a line item has been received. When completed, all order line items and their quantities have been received. Once all materials for the order are received that order status is automatically moved to completed. When cancelled, the order has been cancelled. The user can only cancel if the order is pending. The user cannot change the status of an order from pending to in-progress or from in-progress to complete manually. The status of the order will change from "in progress" or "pending" to "complete" when the user have received all the line items of that order. status will change from "pending" to "in-progress" when the order is partially fulfilled.

Remove an order. Once an order is fulfilled and done with, the user may want to remove it from the list of active orders in the program.

View order details. The order details page gives the user the complete details of the user purchase order, line items in the order and the details of received items, if any. For more information on each order, a user can click on a results page. The top header area of the screen displays the following order attributes: order id, purchase order number, order type, status, ordered by, ordered date, expected arrival date, vendor, and comments. The general tab displays the material list comprising an order. If the order has been made from an allocation request, the user will also see the corresponding allocation request id, responsible person, associated project id, current requested quantity and ordered quantity apart from the line item specific details like: material name, item id, and item code. If the order has been completely or partially fulfilled (e.g., if some quantity of the requested material has been received), the user will see the below receipt details corresponding to the line item such as quantity received, receipt id, and date of receipt. Apart from this, advantageously, the user may view the content of order notes and attachment, if any on the details screen.

Specification plan. Specification plans are templates that define test procedures for a material. A specification plan consists of a series of tests to identify and confirm certain characteristics about a material. Each specification plan is defined for a specific material. The user use these test plans to carry out tests on the material. A specification plan is valid on a material only for a certain period of time after which the user may have to rerun the specification plan on the material. hence, a re-evaluation period is defined for each material lot for a specification plan. As the engineer, the user would define a series of specification plans for a material, put some sample material through a series of assays or tests that are defined in the specification plan, and choose the qualified material lots that meet the specifications so that they can be consumed in the project. Specification plans can be of two types according to their area of usage: process specific, or general. A specification plan defines the following: name and usage type, start date, re-evaluation period, and list of test. In some embodiments of the present invention, a user clicks material>spec plan to: create new specification plan requests, modify existing specification plans, duplicate specification plans, remove specification plans, activate/de-activate specification plans, and/or view specification plan details. In some embodiments, a specification plan has the below attributes associated with it:

| ATTRIBUTE | DESCRIPTION |
|---|---|
| spec plan name | Name of the test plan. This field is mandatory. |
| spec plan type | Can be three types. 'clinical supply', 'synthetic', 'development'. A "development" specification plan indicates that this plan is used solely for non-GMP purposes to get some additional data. |
| material item id | The id of the material item that is associated with the specification plan. This field is mandatory. |
| usage type | Intended usage of the specification plan. the specification plan can be for initial general use, initial evaluation for process specific use, reevaluation for general use, and reevaluation for process specific use or process specific use. |
| approved supplier | This flag indicates that the material must come from a approved supplier for this specification plan to run. |
| description | Description of the specification plan. |
| re-evaluation period | The duration of time before a lot of material has to be retested for the given specification plan. the specification plan itself does not have an expiration date. this value is used to calculate the lot's re-evaluation date (expiration date) for a lot that was tested as specified in the specification plan. This field is mandatory. |
| tests | The tests that the specification plan is associated with. a specification plan can have one or more associated tests or assays. The attributes for a test is below: |
|   test purpose | Test's purpose |
|   test name | Test's name |
|   method id | Identification of the test procedural protocol. one or more method ids can be associated with a test name. |
|   to be monitored | This flag indicates whether the test needs to be monitored or not. |
|   acceptance criteria | The required result to indicate a successful test. if test type = forward processing, the program will ask for a value for "acceptance criteria". If the test type = development only, the program will not ask for a value for "acceptance criteria" This is mandatory. |
|   justification | Justification for the test and the acceptance criteria, this field is mandatory. |

Add specification plan. Adding a specification plan into the program is a two stepped process. First general details of the plan are specified like name, type, usage type, effective start date, associated material, re-evaluation period and rationale. Then specific tests are added to the plan by entering details like test name, purpose, method id, acceptance criteria etc.

A typical specification plan definition has the below characteristics: each specification plan is associated to one material item, while a material item can be associated to zero or many specification plan. Each specification plan will have a re-evaluation duration to determine a lot's re-evaluation date. Each specification plan will comprise one or more tests. Advantageously, a specification plan in the present invention has versioning. Each specification plan can have one and only one approved version active. The user create a specification plan, submit it for review and get it approved so that the user can use the specification plan to test a material sample. A workflow gets initiated when a new specification plan definition is created in the program. If the user is one of the authorized parties of the workflow, the user will see a take action button on the last screen of "add new specification plan" with a task id for the user to submit it for review. An alert gets triggered when the user submits the specification plan for review. This alert message goes to all authorized parties of the above workflow letting them to take the next step further. The user must have appropriate rights to be able to create a specification plan.

Search for a specification plan. The user may search for a specification plan by the following search criteria: material category, material type, material (reference), item id, item code, material name, compound number, spec plan id, spec plan name, version number, and status. The results page will have action buttons that let the user add a new specification plan, edit, duplicate, remove, activate or de-activate an existing specification plan. With appropriate rights, the user can create custom search and result views that may suite individual requirements.

Modify a specification plan. In some embodiments, with appropriate rights, the user can modify the details of an existing specification plan. Modification lets the user change the plan name, type, start date, end date, usage type, re-evaluation duration and rationale. The user may also add or remove tests associated with the specification plan. However, in typical embodiments, the user cannot modify the material item id associated with the specification plan. Modification is possible only if the specification plan is in draft, submitted or approved status. If the specification plan's status is draft, the user could make the following modifications: edit the re-evaluation duration, edit the rationale, and add/remove tests. However, editing a specification plan in draft state has the following constraints: no impact on the associated workflow, and only the workflow initiator/requester can do the editing. Editing will not generate a new version of the specification plan. If the specification plan's status is submitted, the user could make the following modifications: edit the re-evaluation duration, edit the rationale, and add/remove tests. Editing a specification plan in submitted state has constraints: (i) editing will expire workflow task notification which was sent when the user created the specification plan, (ii) only the workflow initiator/requester can do the editing, and (iii) editing will not generate a new version of the specification plan. If the specification plan's status is approved, the user could make the following modifications: edit the re-evaluation duration, edit the rationale, and add/remove tests.

When a specification plan is versioned, the user may edit an existing current version of the specification plan or may opt to create a new version of the specification plan while editing. When the user edits a specification plan in an approved state, a new major version of specification plan is created. If the specification plan status is "rejected" or "obsolete", the program will prevent the user from editing the specification plan.

The user may remove a specification plan if it is no longer of use. The user may view details of a specification plan. For instance, in some embodiments, the specification plan details page displays all associated details of a specification plan like specification plan id, name, type, start date, end date, associated material, re-evaluation period, rationales and the assays included in the plan. The version history tab on the details page displays information like version number, version date, approver, action taken, reason for action etc. Specification plans may be duplicated. This lets the user easily create a new specification plan by taking a copy of an older plan, and by modifying the associated attributes. All details of the original specification plan are copied to the new duplicated one, except the specification plan id which is auto generated.

Specification plans may be activated and deactivated. Deactivating a specification plan will make it unavailable for use. The status of the plan will be set to 'inactive'. Only approved specification plans can be deactivated. The user may re-activate a specification plan, if needed. When a specification plan is re-activated, the program will prompt for the reason for re-activation. By default, a newly created specification plan will be active.

Obsolete specification plans. Once a new version of specification plan is approved, the program moves the previous version of the plan to obsolete status. Thus the program allows only one approved version of the specification plan to be active at a given point of time. The user cannot request an obsolete specification plan to evaluate new lots. All new request to use the specification plan will use the latest version of the specification plan. If a previous version of the specification plan is still in use, the program will allow the associated workflows to be completed.

Approving a specification plan. After a favorable review of a specification plan, the user may want to have the specification plan approved. Approval of specification plan happens through workflow tasks.

Other features. A specification plan undergoes minor intermediate revisions(when the user modify it, etc.) until one of the revisions is approved and released as the next version. These minor revisions of specification plans can be deleted from the database when one version gets finalized (e.g., approved for release). Only the official version is retained for record keeping. In some embodiments of the present invention, the program lets the user compare two tests with the same name but in different versions.

Alerts associated with specification plans. One such alert is the "create request alert." This alert gets triggered when the user submits the specification plan for review and approval. This alert message goes to all authorized parties of the workflow that gets triggered when the user create a new specification plan. In some embodiments, the message will have the subject line which says "new specification plan request created." Another alert associated with specification plans is the cancel request alert. A cancel request alert message is sent when the user cancels a specification plan request. All the authorized parties of the workflow that gets triggered when the user create a workflow will receive this alert message. Another alert associated with specification plans is the approved request alert. This non-mandatory alert is sent if a specification plan is approved.

Workflows associated with specification plans. Some embodiments of the present invention provide two out of the box workflows on specification plans. They are create specification plan workflow and edit specification plan workflow. Workflows are triggered when the user create a specification plan and modifies it. A specification plan needs to be in approved status before the user can use it on a material. The status of a specification plan varies with the associated workflow states. One state that a specification plan can be in is draft state. Draft state is the first state that a specification plan is in (once the user creates a specification plan or once a new version of specification plan is generated). The user cannot use a specification plan in the draft state to evaluate a lot or a container. Another state that a specification plan can be in is submitted. The user cannot use the specification plan to evaluate a lot or container that is in the submitted status. If the specification plan has a workflow that is in progress, then the user cannot edit the specification plan. Another state that the specification can be in is approved. A specification plan has to be in approved state, before it can be used to test material. Actions like modify, duplicate, inactivate, activate and change status can be carried out on an approved specification plan. Still another state that a specification plan can be in is obsolete. Obsolete specification plans are out of use specification plans. When a new version of a specification plan is approved, the program marks the older version as obsolete. The user cannot use an obsolete specification plan to evaluate a material. However, obsolete specification plans can be duplicated. Still another state that the specification plan can be in is rejected. A rejected specification plan cannot be used.

The create specification plan workflow gets triggered the user create a specification plan in the program. Below is an example of the states that this workflow can go through, the action allowed on each state and roles that have the rights to take each action in accordance with an exemplary embodiment of the present invention.

| STATE | ACTIONS | ROLES |
| --- | --- | --- |
| draft(start) | Submit | engineer, chemist, material manager |
| technical review | need more information approve reject | chemist, senior engineer. |
| QC review | need more information approve reject | quality controller |
| approved(final) stopped(final) rejected(final) | | |

The edit specification plan workflow gets triggered when the user edit an approved specification plan. Below are the states that this workflow can go through, the action allowed on each state and roles that have the rights to take each action.

| STATE | ACTIONS | ROLES |
| --- | --- | --- |
| draft(start) | Submit | engineer, chemist, material manager |
| technical review | need more information approve reject | chemist, senior engineer. |
| QC review | need more information approve reject | quality controller |
| approved(final) stopped(final) rejected(final) | | |

A stop specification plan workflow is used when the user is the initiator of the workflow. The user may stop the create or edit workflow at any state. When a workflow is stopped the program will expire further task notifications to any authorized parties of the workflow, the program will obsolete previous revisions of the specification plan, and the current approved specification plan will still be active.

Receiving. Receiving is where the material manager (or the person who receives the material) adds the externally or internally received material into the program inventory. Hence, the creation of inventory for materials is mainly done through material receiving module. Receipts can be external or internal. Externally received materials are those received by place orders with external vendors. Internally received material are those the user receive through inter plant transfers. The user clicks material>receiving to: (i) add material lots and container that are received through external vendors/inter-plant transfers/internal plant transfers into the program inventory, (ii) remove received material lots/containers, (iii) evaluate specification plan against a received expendable lot, (iv) reconcile the receipt of received materials against a purchase order or a dispense to ship request, (v) locate received materials, and/or (vi) print a label for received lots or containers. Each time the user enters a received item into the program, the corresponding order status is also updated. The status of the order will change from "in progress" or "pending" to "complete" when the user has received all the line items of that order. Also, the status will change from "pending" to "in-progress" when the user receives a few of the line items in the order.

In typical embodiments, external material is merchandise received from qualified vendors that are not affiliated to the company. Such material is entered as a brand new receipt into the program. When the user adds a new received material in the program, the user is actually entering it into the program inventory. In an exemplary embodiment, this can be done through a new receiving page. Apart from general details, the user enters the following specific details about the manufacturer on the new receipt page of an externally received material: supplier lot number, internal lot number, manufacturer same as vendor (check box), manufacturer name, site id, and number of lots received. The user may enter the internal lot number, if the user would, otherwise, the program generates an internal lot number which will be displayed on the action complete screen. For each lot received, a user enters quantity received, number of containers, manufacturer date, expiration date, COA, TSE certificate, and comments. The associated container fields will show up if the receiving site has container tracking enabled. The user enters internal container number for each received container. If the user doesn't enter an internal container number, the program will generate one. After every receipt, the program will automatically increase the "quantity on hand" of the material inventory by the received quantity.

When ordered material arrives at the dock, the user captures the following details so that it will be updated to the program inventory: received by (logged in user, by default), receiving site, order type (external or internal), date of receipt, order id, purchase order no, source site and bill of lading. In an exemplary embodiments, the user is prompted to add the following details associated with bill of lading: material name, item id, item code, manufacturer name, site id, number of lots (associated with the manufacturer). Each received material item can have lots from multiple manufacturers. For each lot received, the program prompts the user to enter: supplier lot number, number of containers, date of manufacturer, expiration date, COA, TSE, received quantity, unit of measure, and comments. A lot being received could be a new lot or an existing lot. If it is an existing lot, the user will have new containers in that lot. For each container received for a lot, an exemplary embodiment of the invention prompts the user to enter the following container-level details: container number (optional), package verification, container MOC, container size, UOM (container size), quantity, UOM (quantity), status (container), storage location. The container quantity will sum up to the lot 'received quantity'. At least the following additional attributes may be specified for each lot: package verification, lot status, and storage site. Once a particular material is received, the program will increase the "quantity on hand" of the received material in the inventory by the received quantity. The order status for the order line item will also be updated during receiving.

In typical embodiments, the condition is imposed that material that is received has to be already existing active materials in the program inventory. Therefore, a user has the option of either having system generate or manually enter a unique lot number. The system verifies that the internal lot number is unique. In the case where the user is receiving containers into an existing lot, the lot number is already assigned.

Material received as a result of inter-plant transfer are entered into the program inventory. While receiving the transferred material, the program matches the purchase order number of receiving site with the dispense to ship id of source site. The user provides information like, number of lots received and quantity for each received material line item while adding the receipt. For each lot received, the user enters quantity received, number of containers, lot expiration date, COA, quantity, status, and comments. The user may need to enter container number for each received container. If the user doesn't enter an internal container number, the program will generate one.

A material receipt can be searched for with any combination of the following search criteria: receipt id, receiver, date of receipt, purchase order number (receipt), vendor id, vendor name, bill of lading, site, and status (receipt). In some embodiments, the results page will have action buttons that let the user add a new receipt, edit and remove receipt details, and modify receipt.

Editing receipts allows the user to add or remove line items, add or remove lots, add or remove containers. All of these actions will effectively modify the corresponding records in the program inventory. The user may remove a lot or a container only if no transactions have taken place on any of the lots or containers. When the user removes a material from the receipt, all associated lots and containers will also be removed. If any of the lots or containers of a material that is being removed has any ongoing transaction (for example, if it has been allocated to a process), the removal process will fail and the user will have to manually remove the lots and containers for that material against which no transaction has taken place. The user may edit a received container or lot details only if it has not been already allocated. please remember. In typical embodiments, the container status has to be "in progress" for the user to be able to edit it details. Apart from the above, the user may modify details like receiver user id, date of receipt, receiving site id, vendor site id, purchase order number etc.

All details pertaining to a receipt can be displayed in the view details screen. On the upper portion of this screen the user will see the following details listed: date of receipt, receipt id, order type, order id, received by user id, receiving site, site id, source site, comments, purchase order number, bill of lading, and BO status. The second half of the screen displays three tabs: details, notes, and attachments. The details tab has two sub-tabs: lot and containers. The lot tab displays all the relevant information about the received lot like item id, lot id, material name, manufacturer quantity, received number of containers, manufacturer date, expiration date, COA, TSE, etc. The containers tab details relevant information about the associated containers of the received lots, like container id, package verification, MOC, container size, container quantity, status, storage location etc.

The user may print label for received containers or lots at dock or at internal receiving. The user may select a specific container and print the label with the following information: material name, common name, item id, item code, compound number, handling precaution, NFPA health hazard, NFPA flammability, NFPA reactivity, NFPA special precaution, lot number, container number, quantity, contact person, and expiration date. Alternatively, the user can select a lot and the program will print the corresponding labels for each of the containers associated with the lot. information for the label would be the same as above.

Figure 10:
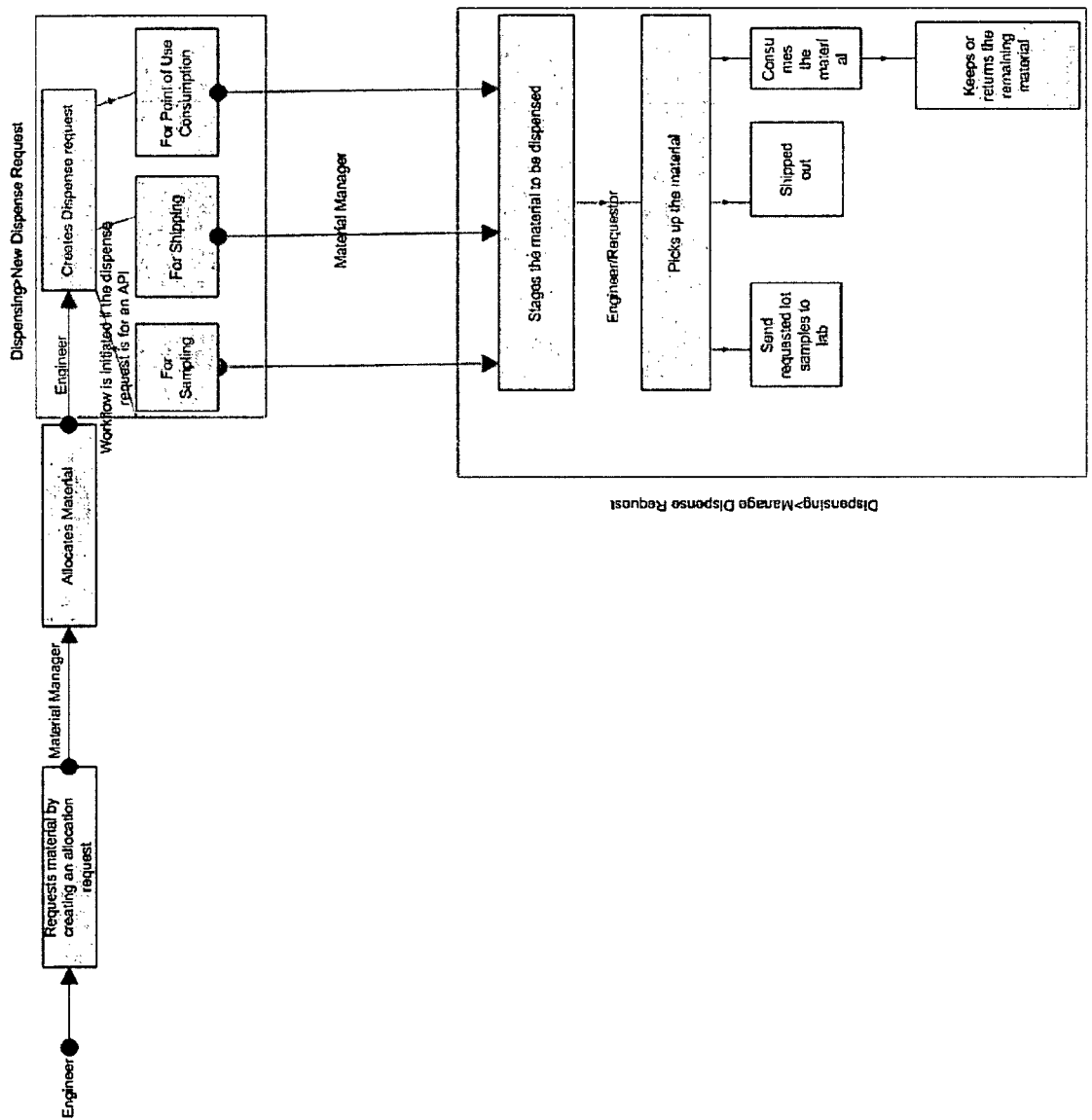
FIG. 10 depicts dispense process flow in accordance with an embodiment of the present invention.

Dispensing means making the material available for use. Material consumption is managed by the program's dispensing module. When an engineer/requester, submits a dispense request to the material manager, the material manager stages the dispensed material. The user can then pick up the qualified material for consumption or else return them. The user can only create a dispense request for a material that is already allocated. A dispensed material can be used for the following purposes: sampling (to be used as samples for test plans), consumption (to be used in the process), point of use (to be used in a process), or shipping (to be shipped out to other plants/locations). FIG. 10 depicts dispense process flow in accordance with an embodiment of the present invention.

Once a lot or container is allocated to a user, the user can go ahead and create a dispense request so that it may be dispensed to the user. Adding a dispense request into the program is a three stepped process: (i) specify general details like dispense type, allocation request id, responsible person, requested by user id, dispense purpose, need by date etc., (ii) specify details of the allocation request for which the dispensing is being requested, and (iii) select the lot/container to be dispensed and specify details like, quantity to be dispensed, date of staging etc. Once a dispensing transaction for a material is completed, the program will send an email alert to the pre-defined set of users with the material id, lot number and container number.

If the user have selected type equals point of use on the new dispensing page, the program will ask for the following details: allocation id (reference), dispense request id, dispense type, status (of dispense request), requester, responsible person, comments, and point of use location id. Apart from the above, the user is prompted to specify, at each line item, the: stage date, and stage quantity. Dispense requests can be created only for allocation requests with fulfilled line items. The user has the option to specify the process step if it is known at the time of the request and if it has not been provided at the time of the material request.

Add a dispense request for sampling. If the user has selected dispense type equals sampling on the new dispensing page, the program will ask for the following details: allocation id (reference), dispense request id, dispense type, status (of dispense request), requester, responsible person, comments, and need by staged date. Apart from the above, the user is prompted to specify the following for each material line item listed on the dispense request: number of samples, quantity per sample, and house sample. If the user selected specific lot and/or container for each material line item listed on the dispense request, the user will be prompted to enter the number of samples required and quantity per sample for each listed lot/container.

If the user has selected type equals dispense for ship on the new dispensing page, the program will ask for the following details: contact person, scheduled shipping date, and planned shipper. In some embodiments of the present invention, the user may search specifically for dispense to ship requests on the locate dispense to ship requests search page. The user may use any of the following attributes as search criteria on this page: dispense, request id, requester, status, contact person's id, contact person's name, contact person's first name, contact person's last name, contact person's email, contact person's company, purpose, shipper, planned shipper, tracking number, shipped date, need by date, project id, project name, target molecule, material name, item id, and item code. The results page will have action buttons that let the user add a new dispense request, edit it, duplicate it and stage a dispense request line item.

The user might want to cancel a dispense request if the requested material is no longer available for use. The user may cancel a dispense request, when user is the requester. The program will send an alert to the people associated with this dispense request workflow that no additional action is required for this dispense request. The user cannot cancel a dispense request that contains lots or container that has already been staged, unless they have been disposed or returned to the warehouse. A completed dispense request cannot be cancelled. With appropriate rights, the user may modify the details of a dispense request.

Staging. The program allows the user to track the process of staging the inventory to the consumption location. Once the user has created a dispense request in the program, the material manager or the responsible person can go ahead and stage the material. If the dispensing request contains specific lots and/or containers, the user may select and stage those lots/containers that match the requested inventories. If the requested lot/container is not available, the program allows the user to select a substitute lot/container to fulfill the dispense request. The user stages a material at a location within the site where dispense requests were made. When all requested line items and quantities have been staged, dispensing request status will become 'staged'. Locating the stage details of a particular allocation or dispense request is done through dispensing>manage staging screen. The user may search for a staged material through stage id, stage status, stage location and staged date. On the results screen, the user can view details like stage id, dispense request id, allocation request id, stage location, staged date and status. The results screen has action buttons that let the user edit stage details, pick-up a staged material, print labels and print staged report.

The user may locate a staged material by its dispense request id or the associated allocation request id. This can be done through locate by allocation/dispense search page. The following search criterion can be used on this search page: stage id, stage location, staged date, allocation request id, and dispense request id. On the results page, the user can enter the pickup details for a selected staged material.

Once the user has created a dispense request in the program, the material manager or the responsible person can go ahead and stage the material for dispensing. If it is an API dispense request, then the request is approved before it can be staged. To stage a material the users (i) selects the containers to be staged and (ii) enters the number of new containers and quantity to be staged. If the quantity on hand/available is greater than the quantity requested to be dispensed, the user might want to bring in some new containers and add only the requested quantity or the quantity that the user want to stage now to the new container(s). Hence, the user has the option to create a new container for material to be dispensed into, to select the container's material of construction and other details. The user further enters the details of the new containers that is going to be staged. Once the user adds a new container, the program will add this new container into the inventory of the corresponding lot.

Advantageously, in some embodiments of the present invention, a staging report displays all the details of a staged material. A staging sheet displays the following information: header area, dispensing request id, responsible person, need by date, intended use, dispense type, comments, and warehouse location. If a 'process' is associated to dispense request the following information is provided: project name, target molecule, material name (e.g. intermediate), item id, item code, and body (material name, item code, lot number, container number, amount requested, and staging location). For each line item on this staging sheet body, the user will see the following values listed: dispensed quantity of the staged material, date of dispensing transaction, time of dispensing transaction, weigh scale id, lot number, comments, two signature lines (dispenser and verifier), weighing, and dispensing. The program allows the user to track and monitor the weighing process during staging. To weigh a material to be dispensed and staged, on the stage screen, the user select the lot or container that is to be staged. If the requested lot/container is not available, the user enters the number of new containers to be added as substitute. In the case where weigh scale details are entered manually, the program ensures a second person's verification of the weigh and dispense transaction.

For each weighing action, the program will display a list of weigh scale ids from which the user can select the weigh scale id that was used for the action. this weigh scale should have at least one calibration logged against it during the course of the day. If the weigh scale has not been calibrated, the program will prompt a warning that says: "weigh scale has not been calibrated within the required calibration frequency. do the user want to continue?" When the user say 'yes', the user can continue with the weigh and dispense operation. If the user says 'no', the user will be provided with the option to calibrate the weigh scale and create the calibration activity log. The user weighs containers one by one. The program allows the user to record the container number via bar code scanning or manual entry. All the containers are listed on the dispense request.

If container-tracking is not enabled, each weigh and dispense transaction is for one lot. The program tracks the following details as the user weigh the contents of the lot/container: material id, lot number, container number, material name, weigh scale id, weighed quantity, new container number, container material of construction, and location. When all requested line items and quantities have been staged, dispensing request status will become 'staged'. If it is a dispense to sample request that is being fulfilled, the program will generate a sample id for each weigh and dispense action.

When the user pick-up items, the user will be required to fill out a specific screen in the program that documents this transaction. For each picked-up lot/container the user specifies the following details: item name, quantity requested, stage id, quantity staged, staged location, staged date, destination location. Once the user has entered the details, the program will generate a pick-up id. A picked up item can take any of the three below statuses: picked up, in progress, and completed.

Advantageously, the program has an effective mechanism that monitors material consumption. All material that has been picked up can be consumed. All materials consumed must come from a qualified site. The user enters the consumption details of a material. The user may also enter consumption details from scaled BOM. The user can locate a consumed material by the consume id or consumed by user id. The user may also search for consumed material the corresponding project id, project name, campaign name, or batch record is known. The search results page will let the user edit the details of a selected consumption transaction.

The user may locate all dispense requests for shipping on the locate dispense to ship search view. This view will display all the relevant details that the user require to know about a dispense request like the dispense request id, requester, status, contact person's details, planned shipper, tracking number, shipped date, need by date, project name, target molecule, material name, item code, item id, etc. The results screen has action buttons that let the user add new dispense request, edit it, duplicate it and stage a dispensed item. Modify a consume transaction. Once the user enters a consume transaction into the program, the user may go back and edit it at a later date, if necessary. A user should be able to edit consume transactions from the manage consume pages. While editing consume transactions, users should be able to consume material from new containers or change the quantity consumed already specified. the consumed quantity can be changed even if the container is returned.

The material library serves two main purposes: to create and maintain material categories. As a first step, to add a new type of material, different material types with their attributes have to be defined in the system. This is done by creating a material category. A material category defines the unique characteristics of a material type. For example, to add an expendable type material into the system, the user needs to first create and define a category called 'expendable'. The user needs administrator's rights to create and manage a material category. Managing material category involves: adding a new category, duplicating a category, removing a category, modifying a category, adding attributes to the category, and duplicating attributes. The user can add/define a new material category. Once material categories are added, the user can add a new material and assign it to a specific category.

Figure 14:
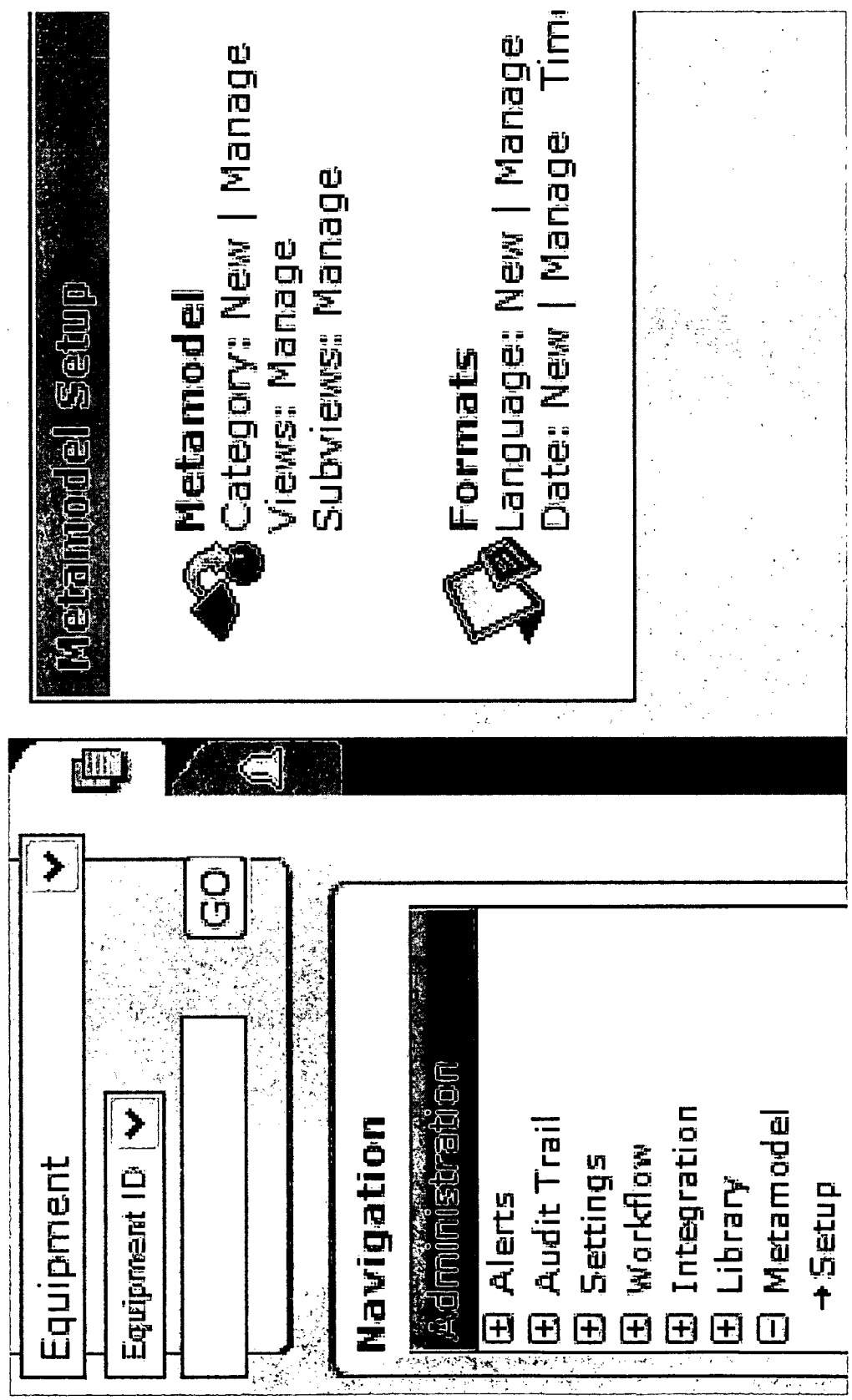
FIG. 14 illustrate a screen for adding a new material category in accordance with an embodiment of the present invention.

Adding a new material category includes the following steps: creating the category, adding attributes to the category, creating schema for the new category, creating views, and creating sub-views. Referring to FIG. 14, the user creates a category. The manage category screen displays with the tabs general, attributes, views and sub views tabs with options to add, edit, duplicate, remove and apply schema for the selected category.

Referring to FIGS. 15 and 16, the user can add new attributes to the material category with appropriate rights. While defining attributes for a material category, the user needs to provide values for the following: attribute name, attribute label, attribute db name, data type, description etc. The user may press click 'value required' to specify that this attribute cannot have null values. The user may click 'primary key' to specify that this attribute will be part of the primary key on the category. The user may click 'hidden' if the user doesn't want an attribute to be displayed on the user interface. The user may click 'privilege required' for the attribute to have privileges associated with it. The user may click 'auditable' to set the attribute as auditable so that all the changes on the attribute is trackable using audit trail. Clicking 'externally derived' is done for the values of this attribute to be derived externally. A web service, specified by the administrator, will fetch the values for externally derived attributes. Clicking 'required in view' for the attribute to be a part of all the views created on that category. A user may click 'indexed' for the database column created for this attribute to be indexed. A user may click 'editable' to indicate the value for this attribute can be edited. Clicking "hyperlinked" indicates that the given attribute will be shown as hyperlink. The new attribute details tab is highlighted with the name of the container category and attribute displayed on the top left side of the screen. The field names on the new attribute details tab depends on the data type that the new attribute belong to.

In order to duplicate an existing material category, the user specifies a unique name for this duplicated category and unique category database name. All properties of the original material category are duplicated, except for the data and the views of the category. the new category will be in "schema not created" state. The user creates schema for this category. In order to duplicate an existing attribute, the user needs to provide appropriate values such as: attribute name, attribute label, attribute db name, and description. If an inherited attribute is duplicated, the duplicated attribute will belong to the current category and not to the parent category. The user can modify details of the existing material category. For instance, in some embodiments, the program allows the user to change a database name as well as add or remove attributes. The program will not allow the user to delete an attribute if a value has been entered in the attribute of a piece of material.

Removing an existing material category is possible only if no material instances exist within that category. The program lets the user manage a material item by: creating, managing and viewing raw, intermediate, and final materials, duplicating a material, comparing materials, removing a material, moving a material, and activating/de-activating a material. For example, to add new material, the user enters material information in the following exemplary sequence: (i) type (raw, intermediate, API) and name, characteristics such as density, molecular weight, compound name, CAS composition, safety requirements such as if it's a controlled sequence possibly causing a NAPA heath hazard, storage and handling requirement such as required room temperature, storage conditions, and security requirements. When all the material information has been entered into the program, the user can search and modify it.

Figure 11:
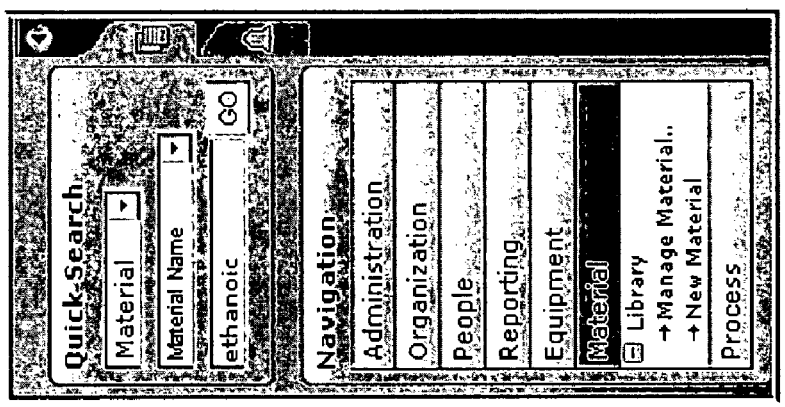
FIG. 11 illustrates an exemplary material search pane in accordance with an embodiment of the present invention.

The user can search for material when the user wants to take action on it such as modify, edit, copy, etc. The user can search, sort and filter material if the user has the privileges to do so. The user can also do a wildcard search. The user can search for a material by category. The user may also locate a material item by its name, category name, item id, material name, item code, material type, compound number, CAS number, CAS name, physical state, molecular formula etc. FIG. 11 illustrates an exemplary material search pane in accordance with an embodiment of the present invention.

Figure 12:
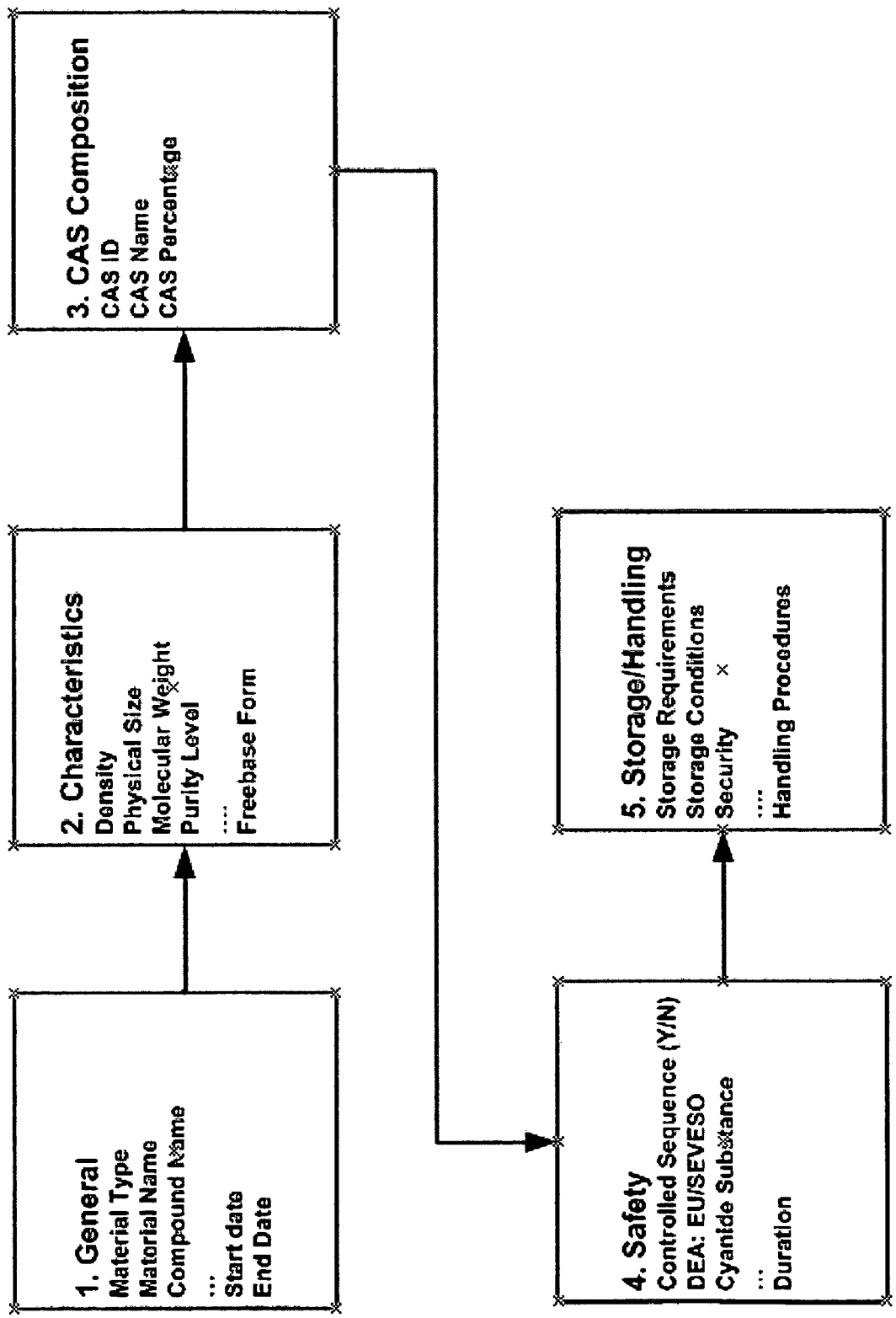
FIG. 12 illustrates a process for specifying the attributes of a material in accordance with an embodiment of the present invention.

The user can search for an expendable material by specifying the attributes like expendable type, expendable name, expendable item code etc. The program provides default expendable details search view for locating expendable type materials. Adding a new material into the program involves: selecting the category to which the material belongs and adding the new material into the category. The user enters a new material into the program by filling out five tabs that correspond to the five steps illustrated in FIG. 12. This describes the new material with its unique characteristics.

A duplicating material record results in creating a new instance of the material. In typical embodiments, the user has the appropriate rights to be able to duplicate a material. A duplicated material is editable. Further, with appropriate rights, the user may be able to remove a material that is not in use. The user will get an error message if the user try to remove a material that is used, consumed, dispensed, allocated or listed on a bill of material. A material that has never been used before may be removed. To remove a material, the user searches for the material, selects the material, and removes it. Modifying a material essentially means changing its general description, characteristics, CAS composition, safety attributes, and storage and handling specifications of the material. The material category and item id are not editable. Each time the user modifies a material, the user is prompted to enter the reason for modification and this information is logged into the material change history for audit purposes. The user should have the necessary privileges in order to be able to edit the details of a material. In some embodiments, the steps taken to modify a material begin with navigating to material bar>library>manage material, next on chemical material, the user clicks its expand icon (+)>select raw material. The user can select a different category id and the material would be different. Values are entered into the following fields: compound number, low inventory amount, effective start date, and purity level.

With appropriate rights, the user can activate or de-activate a material. The user will be prompted to enter the reason for change, with the start date, end date, time and name of the person while activating/de-activating. To activate or de-activate an item, the user searches for the item, selects the item, and activates or de-activates the item.

A user can move a material item from one category to another. If the new destination category has more attributes than the original one, the user needs to fill in the values for those extra attributes. If the material is moved to a category which has less number of attributes then a warning will be displayed that some of the data will be lost.

Material can take one of the four statuses: draft, submitted, approved, and rejected. When the user adds a new material it goes into draft status. Status of a material can be changed manually or through a workflow. The user needs to have the appropriate rights to be able to change the status of a material manually. A material can be used in a process only if it is in the approved status. The user can edit a material only if it is in the draft status.

There are two workflows that are initiated when the user creates a material: (i) create material type chemical workflow and (ii) create material type expendable workflow. The create material type chemical workflow initiates when a user creates a chemical material. The possible states for this workflow are: draft, submitted, approved (final state), stopped (final state), rejected (final state), and cancelled(final state). The action button on each state are given in the following chart.

| STATE | ALLOWED ACTIONS |
| --- | --- |
| draft | submit |
| submitted | revision requested, approve, reject, cancel. |

The roles and privileges on each workflow states are given in the following chart.

| ROLE | PRIVILEGES TO |
| --- | --- |
| chemist | create, submit |
| engineer | create, submit |
| material manager | create, submit, approve, request revision, reject, cancel. |
| material specialist | approve, request revision, reject, cancel. |
| QC | approve, request revision, reject, cancel. |

All the rules of workflow applies here. An initiator can stop the workflow at any state provided he has checked the "allow stop workflow" check box while creating the state.

Bill of material (BOM). A bill of materials, BOM, can be described as a list of materials required to produce a target quantity of material. The produced target material could in turn be an intermediate for producing another material with another bill of material associated with it. In typical embodiments, are three kinds of bill of material needed for a process: master bill of material, planned bill of material, and production bill of material. The master bill of material is the template by which the user defines the actual bill of materials that will be used up in the process. The planned BOM is a BOM lists material created from the master BOM, but with the materials that the user plans to use up in a process. However, this may not be sufficient to show the actual materials used or that are approved to be used in each stage of the production process. Hence, this is just a "planned" bill of material. A production bill of material is an approved planned BOM that is filled up with the actual available material listing becomes a production BOM. The production BOM is produced automatically by the program.

The BOM can be used to maintain a record of what happened in a production step even after the process is over. Once a production step is over, the material used in the process will be relieved from the inventory and the end product will be added into the inventory. With a BOM, the user can keep a record of the kind of materials used up in a process, the modifications that happened to the material during the process, thus providing a complete history of evolution of a new target material.

The straightforward way to create a master BOM in some embodiments of the program is through material>BOM>new. A given material can be a participating member of several BOMs. The user specifies the BOM name, type, target material, target material, quantity of target material to be produced etc. . In turn, the program will generate a BOM id for the user, once the user has finished creating a BOM. The user may also save a scaled BOM as a new draft master BOM or save it as an updated draft version of the referenced BOM from master batch record manage option. A 'save scaled BOM as a master BOM' option is available only on approved master batch record.

The user may locate a master BOM on a manage BOM search page by specifying any of the following search criteria: BOM type, master BOM id, material name, item id, compound number, item code, synthetic route, status, created by, version number, target molecule, created user, synthetic route, etc. The results page will display action buttons that let the user create a new master BOM, edit it, duplicate it, remove it, activate/de-activate it and change the status of a BOM. The edit page essentially lets a user add or remove material comprising the master BOM. Apart from this, the user may also change BOM name, type, synthetic route, target material and total target quantity. In preferred embodiments, the user may edit a BOM only if it is in the draft or published status. Editing a published/approved master BOM will effectively create a new copy of the BOM which will be in the draft status. The previous version of the master BOM will be stored in the database due to the fact that some batch records might still be using it. However, each time a user edits a published BOM, a new version of it is created. From then on, this new version will be active and the original version will become obsolete. Obsolete master BOMs cannot be used to create scaled BOMs.

A bill of material can be in any of the three below statuses through out its life period: draft, published, and obsolete. A newly added BOM is in the draft status. The user cannot import a master BOM in draft status to create a scaled BOM. However, the user can edit or remove such a master BOM. A published master BOM is an approved BOM. The user may change the status manually or it may happen through an associated workflow. The user may modify, duplicate or change the status of a published master BOM. An obsolete master BOM is not editable. Also, such a BOM cannot be used to create a new scaled BOM. The user may manually change the status of a master BOM to published or obsolete. With appropriate rights, the user may remove a master BOM. The program allows the user to remove a master BOM if it is in draft status and is not associated with a workflow.

Advantageously, in the present invention, a master BOM is versioned. There is a minor and major versioning. For example, in some embodiments, a newly created master BOM is versioned with the designation 0.1. Once the master BOM is approved, it will be assigned the next major version (1.0, 2.0 etc). Editing a master BOM will create a new minor version of the BOM. If the master BOM is rejected during approval process and a rework has been instructed, the minor version number will not be incremented. The save operation will not increment the minor version. However, any subsequent change after the master BOM has been approved and released for use will increment the minor version which will be driven completely by the workflow state configuration.

Figure 17:
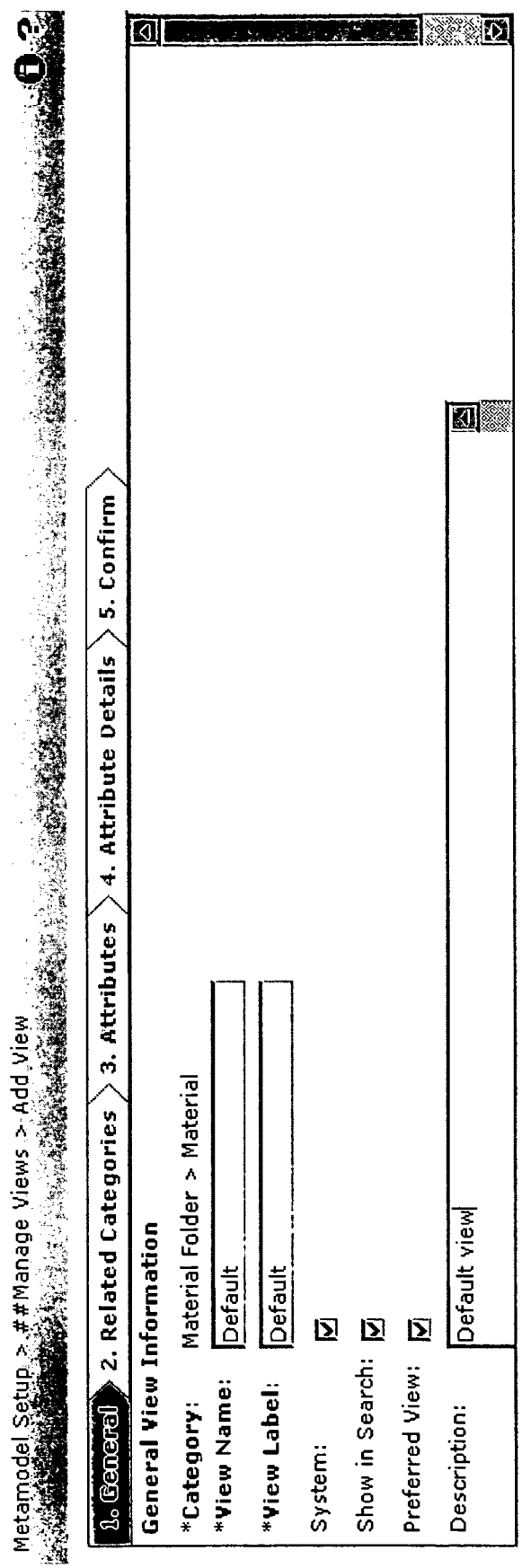
FIG. 17 illustrate how views can be created for material in accordance with an embodiment of the present invention.

Creating views for material. Advantageously, referring to FIG. 17, views can be created for a material.

Equipment Management Module

Figure 24:
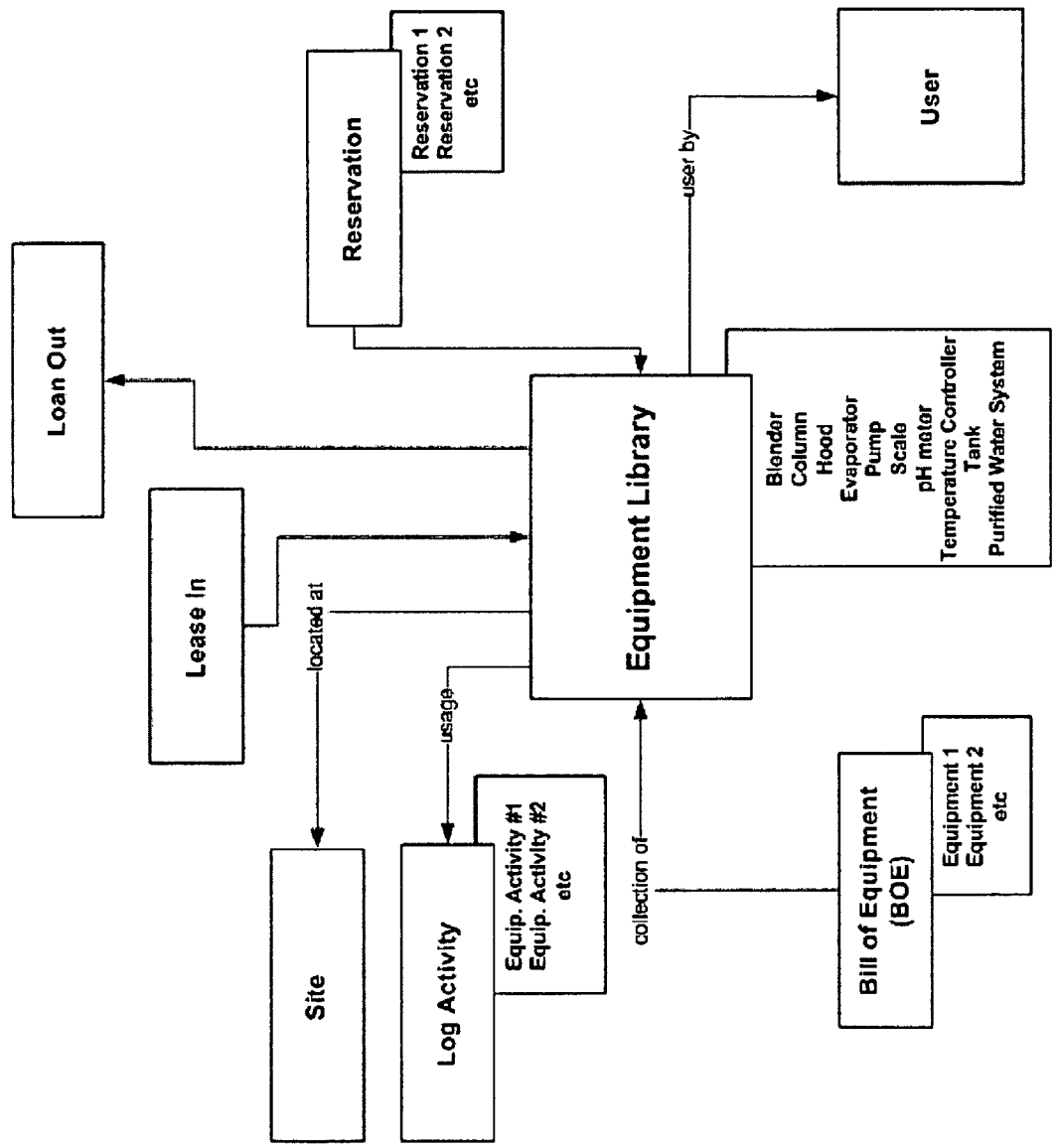
FIG. 24 illustrates the inter-dependencies of various element of SUMS with elements in the equipment management module in accordance with an embodiment of the present invention.
Figure 25:
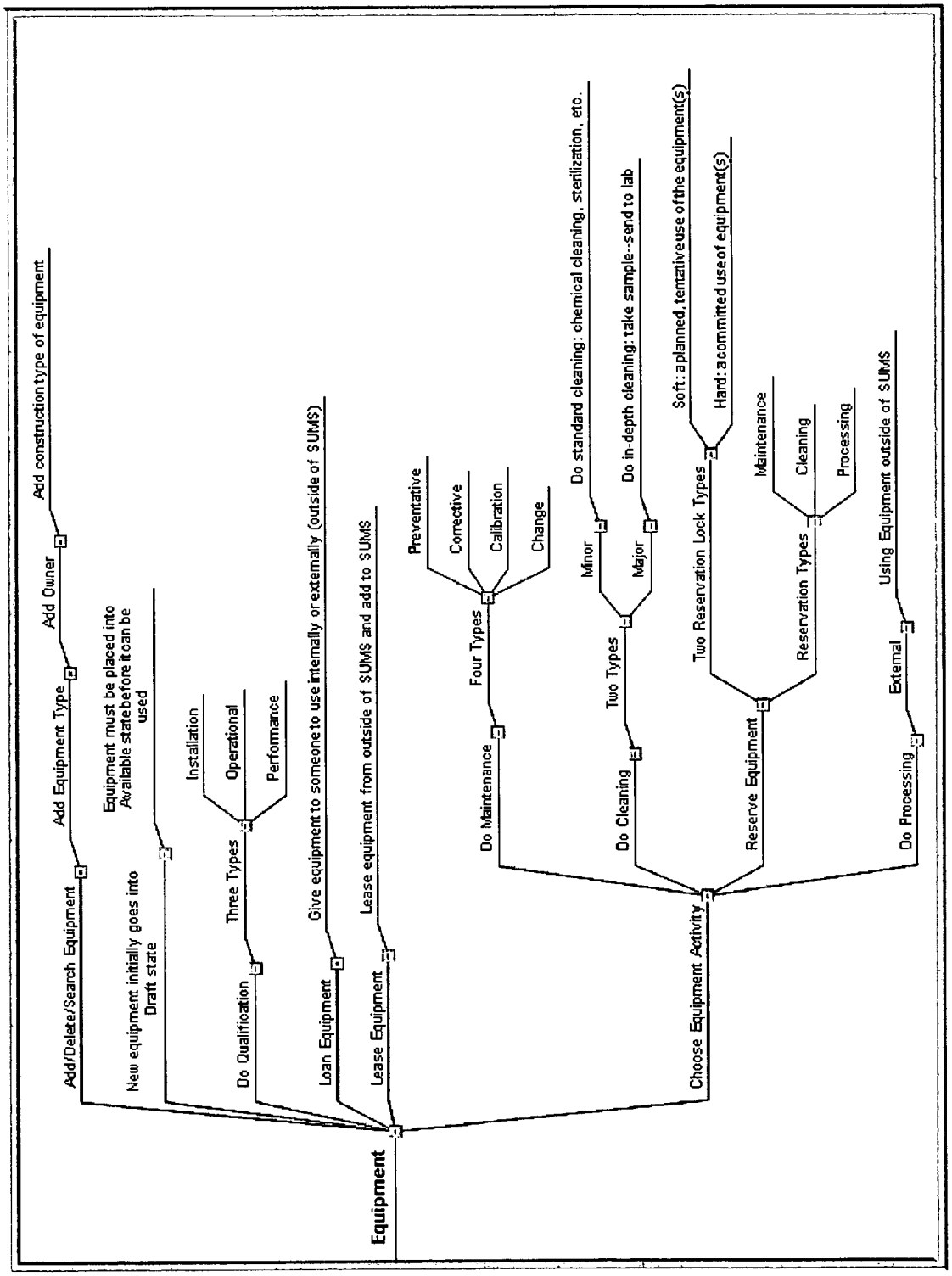
FIG. 25 illustrates what tasks can be accomplished with a equipment module in accordance with an embodiment of the present invention.
Figure 33:
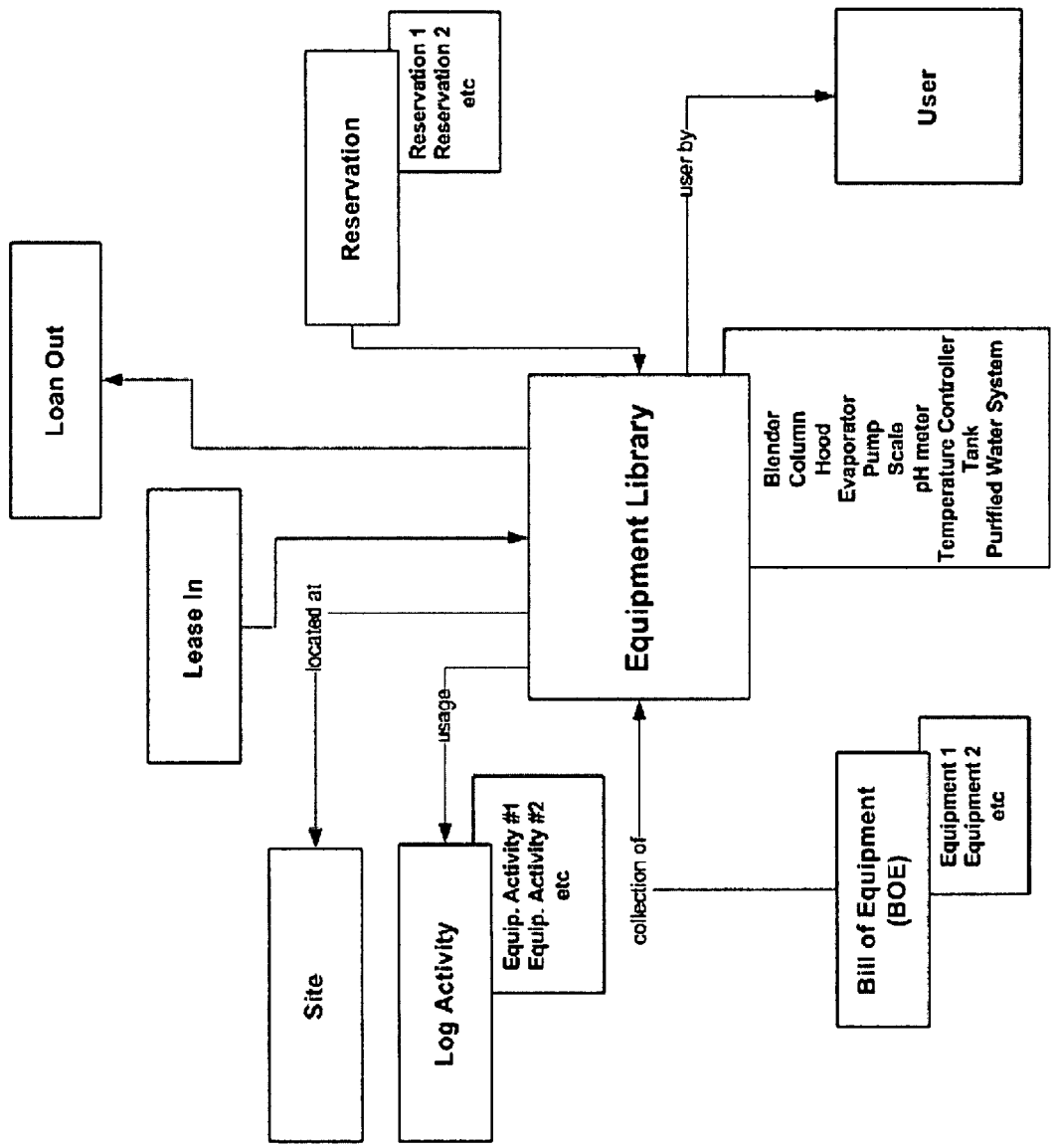
FIG. 33 illustrates the inter-dependencies of various elements of the program with elements in the equipment management module in accordance with an embodiment of the present invention.
Figure 34:
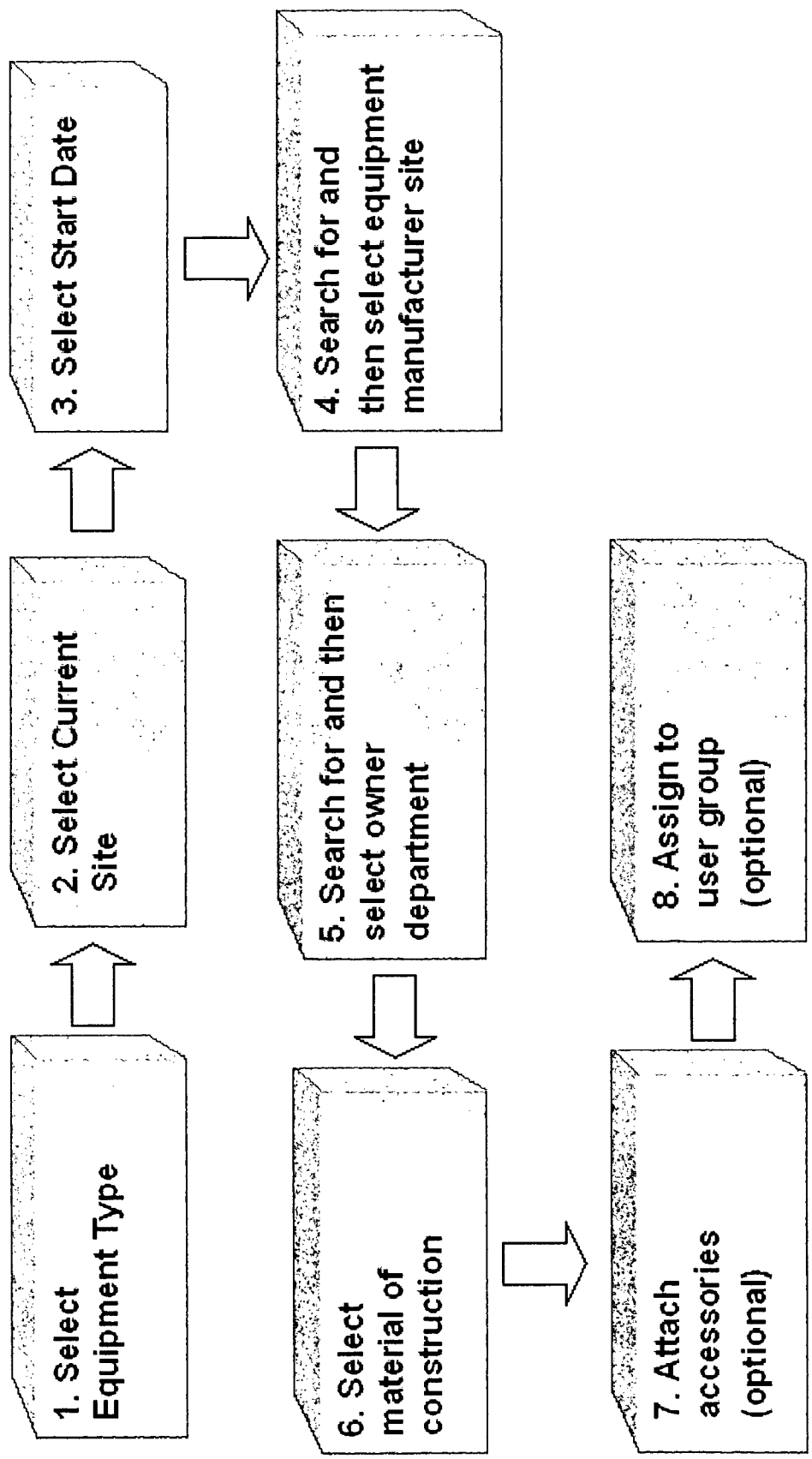
FIG. 34 provides examplary of steps for creating a new piece of equipment in accordance with an embodiment of the present invention.
Figure 35:
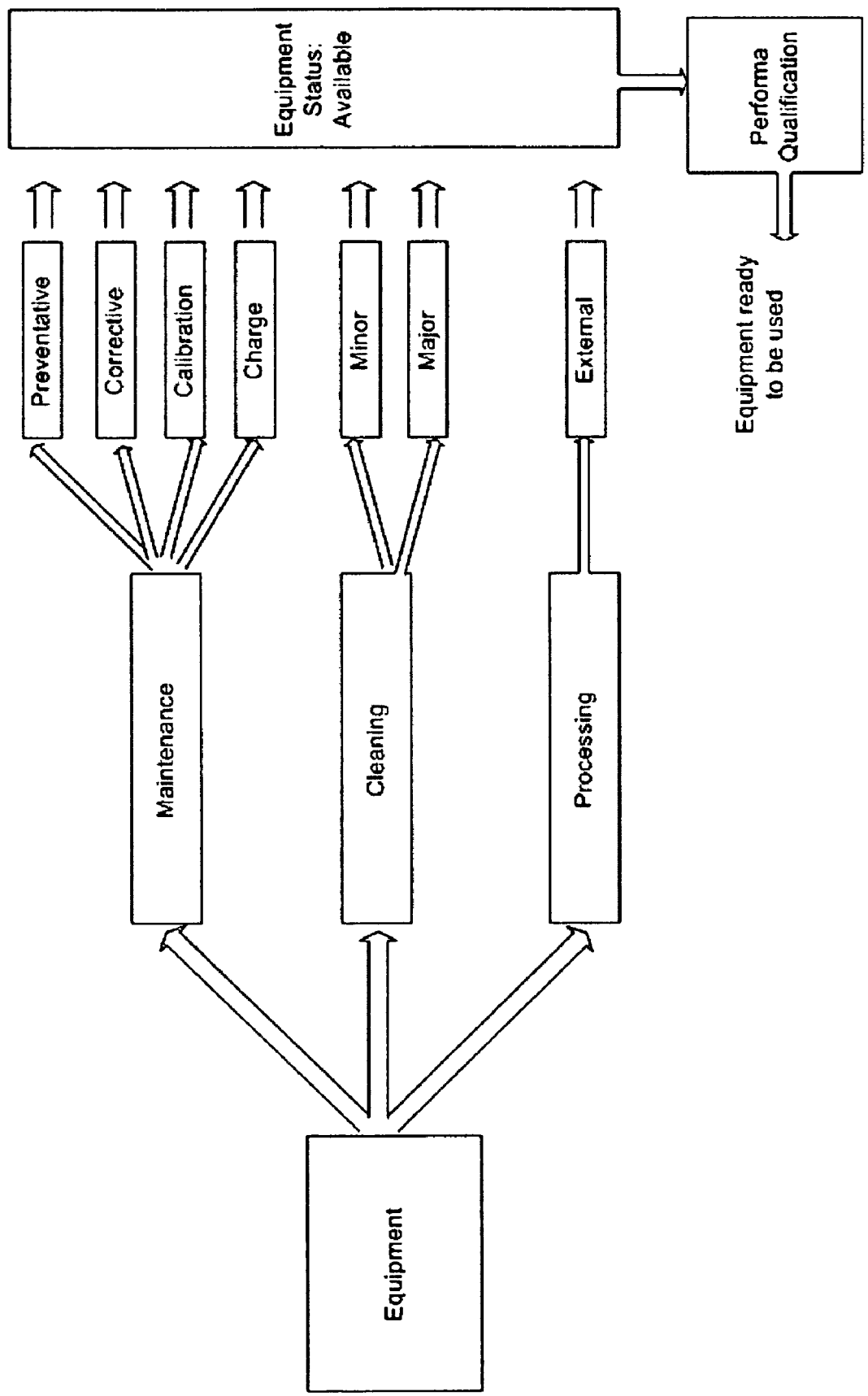
FIG. 35 illustrates equipment activity flow in accordance with an embodiment of the present invention.

The equipment management module of FIG. 13 allows a user to add new equipment, search and modify the equipment, compare equipment, activate and deactivate equipment, lease or loan equipment, make reservations on equipment and classify the same as a hard (firm) or soft reservation, check availability of equipment for reservation, and duplicate equipment. FIG. 24 illustrates the inter-dependencies of various elements of SUMS with elements in the equipment management module. FIG. 25 is a high-level graphic that illustrates what tasks can be accomplished with the equipment module (e.g., reservation, qualification, loan/lease, library, etc.). FIG. 33 illustrates the inter-dependencies of various elements of the program with elements in the equipment management module. FIG. 34 provide exemplary of steps for creating a new piece of equipment in accordance with an embodiment of the present invention. FIG. 35 illustrates equipment activity flow in accordance with an embodiment of the present invention.

Process Management Module

Figure 26:
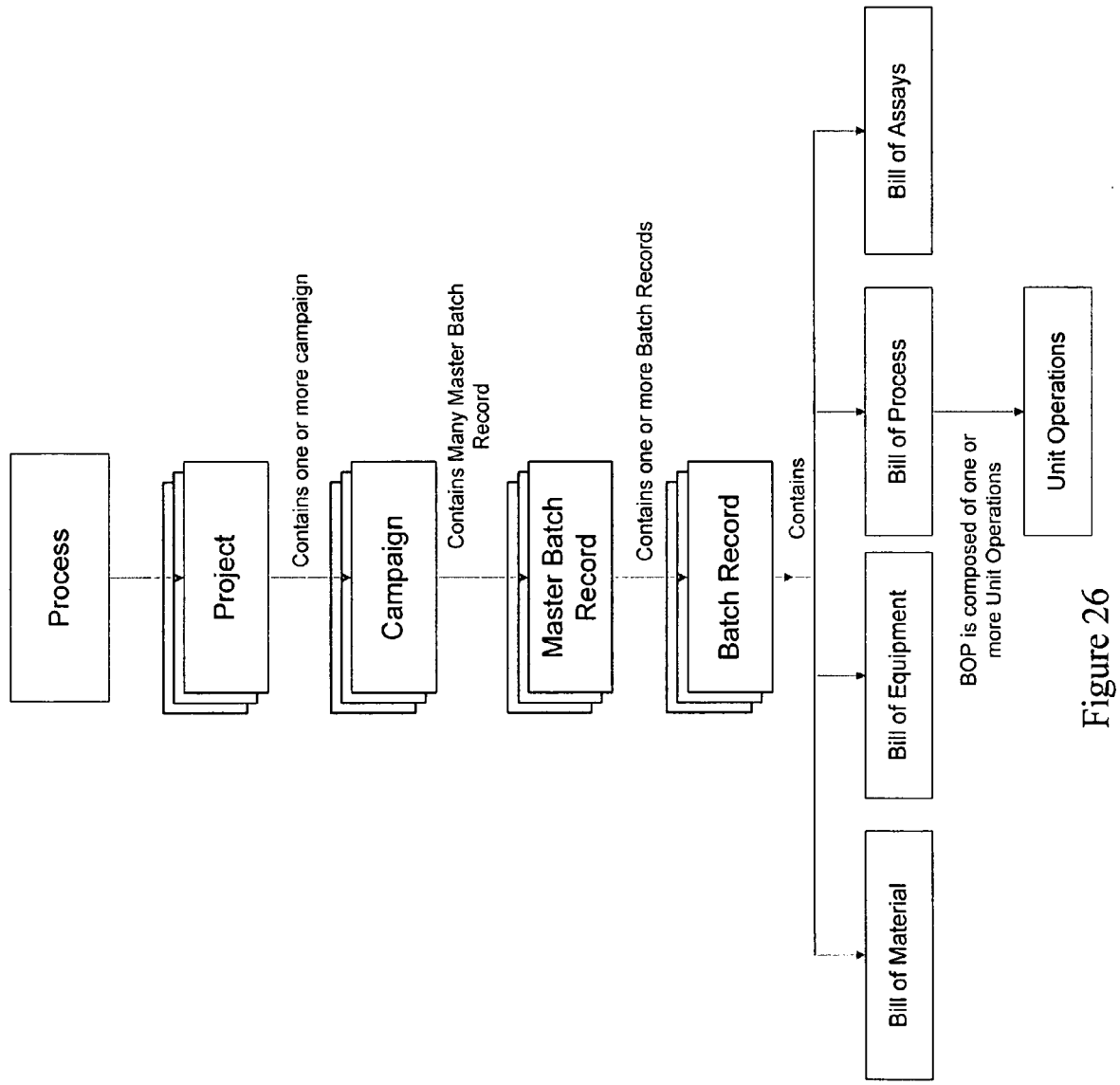
FIG. 26 illustrates a process flow diagram in accordance with an embodiment of the present invention.

A process is composed of five components: project, campaign, master batch record, batch records, and unit operations. FIG. 26 illustrates a process flow diagram in accordance with an embodiment of the present invention. The table below lists the five Components of the process.

| CATEGORY | DESCRIPTION |
| --- | --- |
| Project | Create new projects, modify them, add personnel to it, view its details, and create target molecules. |
| Campaign | Create one or more campaigns, search for a campaign and view its details. |
| Master Batch Record | Master batch record is a sequential process required to produce the required material. The user can create new master batch records that are procedures for creating the batch lots that lead to scaled up/down quantities of the materials being produced. |
| Batch Record | Batch records are produced to list all the materials, equipment, and master batch records that go into making a batch (also known as a lot) of immediate or target materials. (comprises a planned batch record section and a production batch record section.) |
| Unit Operation | A unit operation is a work instruction to perform one specific processing activity. Unit operation is made up of one or many unit operation actions. |

Figure 27:
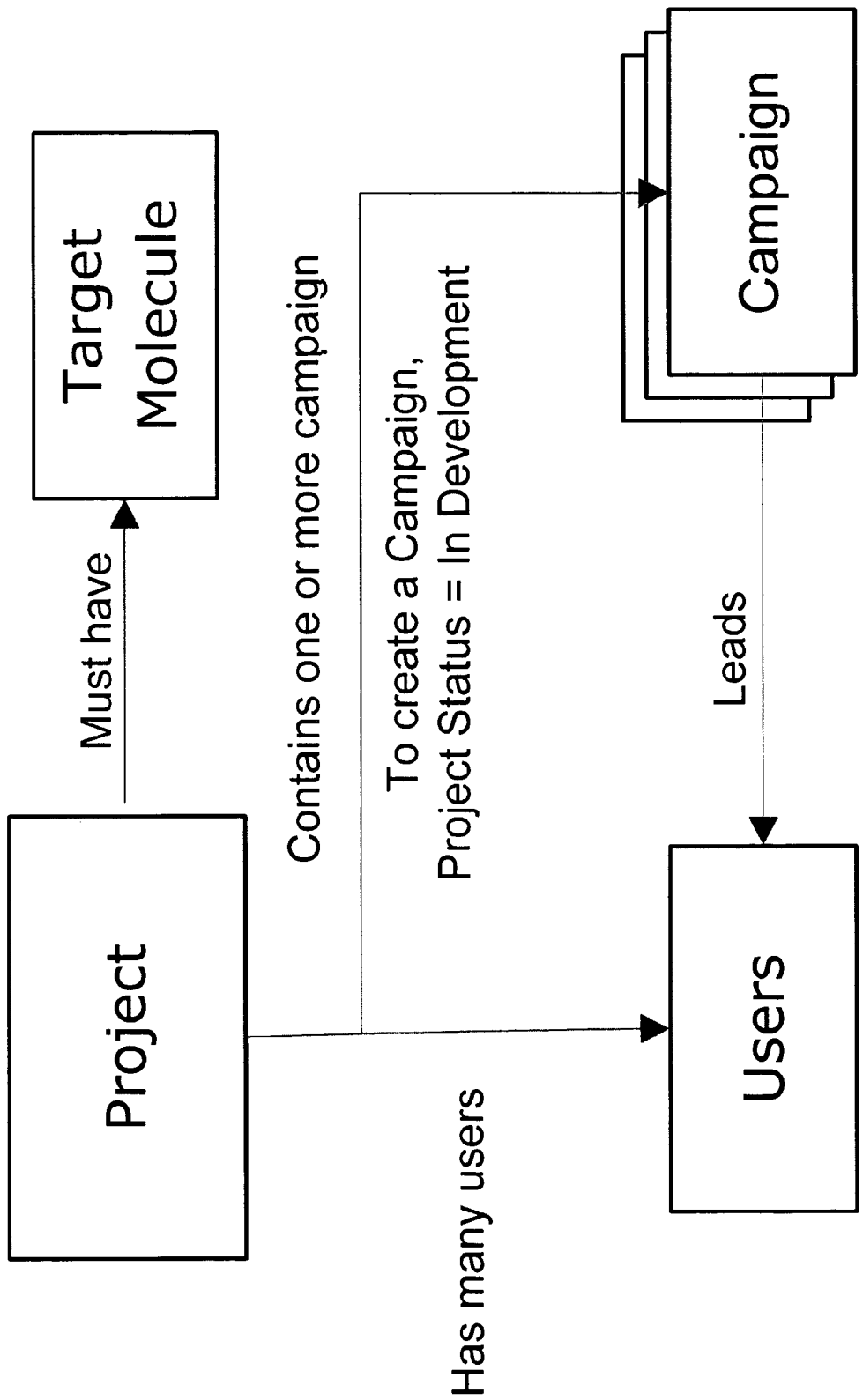
FIG. 27 depicts the inter-dependencies of various elements in a project in accordance with an embodiment of the present invention.

Project management. A project has one or multiple molecules (usually variants of the same base molecule) all aiming at synthesizing an API for a specific indication or indications. If the project is associated with more than one target molecules, the result table will display more than one row for the project with each row displaying an unique combination of the project and target molecule. The user initiates a project to develop a target material. A project typically is composed of one or more campaigns. It has many users (lead contacts). For example, to start a new target molecule research process, a user creates a project that will name the target material and all the personnel involved in the project. The diagram on FIG. 27 depicts the inter-dependencies of various elements in a project.

With the help of the new option from left navigation pane of the application, a user can add a new project. Adding a new project involves the following functionalities: general information, target molecule details, lead contacts details. With the help of the manage option from the left navigation pane of the application, a user can manage a project. Managing a project involves the following functionalities: add a new project, search for a project, create a target molecule, search for a target molecule, modify a project, view general project details, modify a project, remove a project, duplicate a project, deactivate a project, activate a project, manage a Campaign. For each project created, a user can associate multiple project leaders (lead contacts): CMC project manager, CMC project manager_backup, pharmaceutical scientist, lead chemist, analytical scientist, and toxicologist. The CMC project manager is the project manager responsible for managing a project through chemical, manufacturing, and control (CMC) regulatory process. The CMC project manager backup is the backup person for the CMC project manager. A pharmaceutical scientist is a person responsible for the development of the drug product. A lead chemist is the person responsible for the development of the project's drug substance. An analytical scientist is the person responsible for the development of the project's analytical development and test. The toxicologist is the person responsible for the development of the project's toxicology testing and analysis. A user can add a new project in two different ways: (i) by selecting the new option from the project drop-down menu in the left navigation pane of the Application, or (ii) by selecting the manage option from the project drop-down menu in the left navigation pane of the application.

While adding a new project, the user can associate multiple target molecules, multiple project leaders, and can add additional titles for lead contacts. The desired molecule must be in the program. If the molecule does not exist, a new target molecule is created. On selecting the target molecule with the in-development status that has been already assigned to some other project, it will display an error "target molecule already assigned to another project with status in development in row. 1" A sanctioned date has either current or some past date. The user should have the appropriate rights to set the status of project 'in development'. In preferred embodiments of the present invention, selecting a lead contact is mandatory. In case of non-selection of lead contact, it will display an error "lead contact is a required field in 1 row. Please enter a valid value." A project can have a number of target molecules. The default is one target molecule. With the appropriate rights, the user can create, modify, remove, duplicate views for a project (refer to metamodel>views>manage). Every view has searchable attributes and result attributes associated with it. Search screens would be rendered based on the searchable attributes and results screen would display values only for result attributes. However, specifying search criteria can perform search using all the result attributes as well.

Search for a project—basic. A user can search for a project by selecting the manage option from the project drop-down menu in the left navigation pane of the application. A user select the basic option from the view. Next the values are entered in the appropriate fields by clicking on the lookup icon or by entering the values manually or leave all the field blank to search for a project. The following search criteria may be used: indication, project id, project name, target molecule id, target molecule, project lifecycle, project status, therapeutic area, GBIP project number, and WBS code. The following are the column lists under result: project id, project name, target molecule id, target molecule, project lifecycle, project status, therapeutic area, indication, and comments. The user can search for a project by selecting the manage option from the project drop-down menu in the left navigation pane of the application. The user selects the default option from the view and then enters the values in the appropriate fields by clicking on the lookup icon or by entering the values manually or leave all the field blank to search for a project. The user then selects any of the following search criteria: project id, project name, therapeutic area, indication, description, project lifecycle, sanctioned date, comments, created date, modified date, created user, and/or modified user. The following are the column list under results: project id, project name, therapeutic area, indication, description, project lifecycle, sanctioned date, comments, created date, modified date, created user, and modified user.

The user can search for a project by selecting the manage option from the project drop-down menu in the left navigation pane of the application. select the locate by leaders option from the view. The user enters the values in the appropriate fields by clicking on the lookup icon or by entering the values manually or leave all the field blank to search for a project. click search. The following are the search criteria: project id, project name, target molecule id, target molecule, project status, lead contact type, lead contact id. lead contact name. The following are the column list under result: project id, project name, target molecule id, target molecule, project status, lead contact type, lead contact id, and lead contact name.

The user can search for a project by selecting the manage option from the project drop-down menu in the left navigation pane of the application. The user selects the locate by campaign option from the view and enters the values in the appropriate fields by clicking on the lookup icon or by entering the values manually or leaving all the fields blank to search for a project. click search. The following are the search criteria: project id, project name, target molecule id, target molecule, campaign id, campaign name, item code, item id, material name, compound number. The following are the column listed under result: project id, project name, target molecule id, target molecule, campaign id, campaign name, material, target delivery date, and campaign status.

The user can search for a project by selecting the manage option from the project drop-down menu in the left navigation pane of the application. The user selects the project quick search option from the view and enters the values in the appropriate fields by clicking on the lookup icon or by entering the values manually or leave all the field blank to search for a project. The following are the search criteria: project id, project name, and target molecule. The following are the column lists under result: project id, project name, target molecule, therapeutic area, and indication.

View project details. The user can view the project details by selecting the manage option from the project drop-down menu in the left navigation pane of the application. The user selects the view and then enters the values in the appropriate fields by clicking on the lookup icon or by entering the values manually or leaving all the fields blank to search for a project. The list of projects with the detail will be displayed under the result. The user clicks on the project id of the project the user are interested in, which is displayed in the search result of the different (e.g., default, basic, campaign, leaders, and quick search) views. The following are the tabs displayed in the project details page: details and characteristic (target molecule, lead contacts, campaign, synthetic routes).

The automatically track the following information: last modified (the program generates a time and date when a project was last modified), last modified by (the program captures the person that last modified the project), created date (the program generates a time and date when a project was created), created by (the program captures the person that created the project), and view project details (characteristics details). On clicking project id, the project details page of the project that the user is interested in will be displayed.

View project details. Target molecule details are viewed by clicking on the project id hyperlink that the user of interest. The user can view the target molecule details by clicking on details>target molecule. The target molecule details include the following information: molecule id, molecule name, and target molecule. Campaign includes the following information: target molecule id, campaign id, campaign name, campaign leader, campaign status, material name requested, material compound number requested, material item code, requested delivery date, requested quantity, requested original synthetic route, final synthetic route, actual delivery date, and actual quantity. The user can view the synthetic route details by clicking on synthetic route tab. The synthetic route includes the following information: project id, project name, target molecule id, molecule name, campaign id, campaign name, synthetic route, product name, and compound designation. The user should have appropriate rights to modify the project details through project>manage option of the menu. On continuation, the program will display a window to enter the reason for modifying a project. The program automatically tracks the following information: last modified (the program generates a time/date when a project was last modified), last modified by (the program captures the person that last modified the project), created date (the program generates a time/date when a project was created, and created by (the program captures the person that created the project. The user can modify project name, target molecule details, lead contact details, sanctioned date, project lifecycle, and therapeutic area. In preferred embodiments of the present invention, the user cannot modify project id.

Remove a project. In preferred embodiments of the present invention, the user has appropriate rights to remove the project from the program. The user can remove the project only when it is in the draft status. When removing a project, the program will display a dialog box saying "selected record(s) will be removed from the system, continue?" On continuation, the program will display a window to enter the reason for removing a project from the sums.

Duplicate a project. The user should have appropriate rights to create replica of the project with the all data that has been entered as part of the creation of the project. create the project in the draft mode. Since there is restriction on status of the target molecule, when cloning the project the sums present the UI with a list of target molecule(s) that were associated with the cloned project and allow the user cloning the project to modify their status. A project being cloned may have campaigns→master batch records→batch records associated with it. The duplication operation will not duplicate the association of the campaigns to projects. If a campaign or master batch record is active and in progress (e.g. in the middle for the workflow), while deactivating a project, the program will display a warning message. On continuation, the program will display a window to enter the reason for deactivating a project from the program.

Activate a project. While activating a deactivated project, the program will display a warning message. In some embodiments, the program will display a window to enter the reason for activating a deactivated project from the program. The program will capture the audit trail of this transaction. The user cannot change the project status to parked or cancelled when active campaign(s), master batch record(s), batch record(s), is(are) associated with the project.

Alerts associated with project. On alert associated with a project is a new project alert. This is a non-mandatory alert that gets triggered when a new project is created and the status of the newly created project is 'in development'. The alert message will contain the details like project id, project name, target molecule, therapeutic area, indication, sanctioned date, and status. Another alert related to a project is a cancelled project alert. This alert is triggered to warn all lead contacts associated with project that the project has been cancelled. The alert message will contain the details like project id, project name, target molecule, therapeutic area, indication, sanctioned date, and status. Still another alert associated with a project is a parked project alert. This alert is triggered to warn all lead contacts associated with project that the project has been parked. The alert message will contain the details like project id, project name, target molecule, therapeutic area, indication, sanctioned date, and status.

Figure 28:
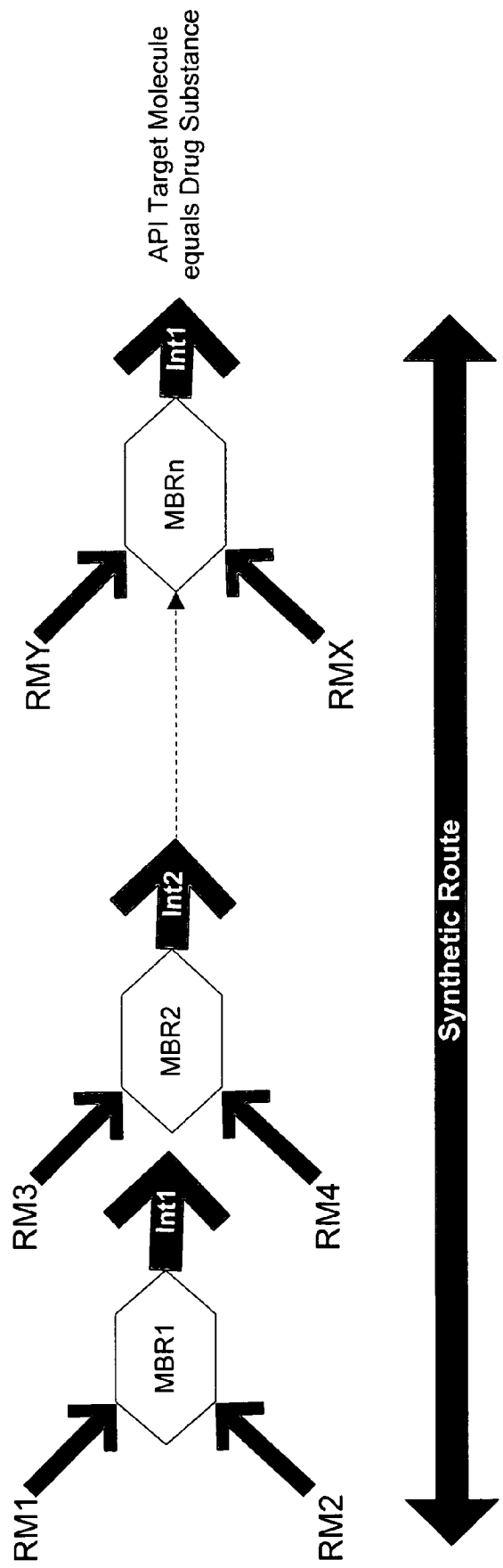
FIG. 28 depicts how a synthetic route is organized in accordance with an embodiment of the present invention, where RM stands for raw material, MBR stands for master batch record, and INT stands for intermediates.
Figure 29:
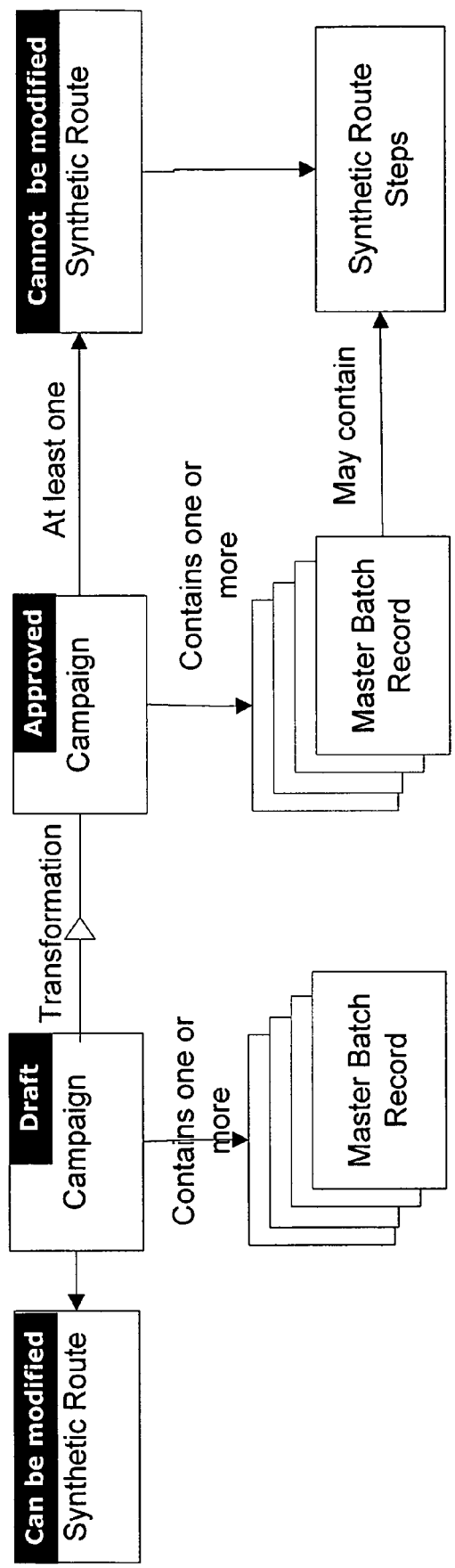
FIG. 29 depicts how a campaign, master batch records, and synthetic routes are inter-related in accordance with one embodiment of the present invention.

Campaign management. The user can create one or more campaigns within a project. A campaign typically is composed of many master batch records. For example, each campaign is designed to create the target material. The user needs to give an estimated date for creation of the target material and all personnel associated with each campaign. Each campaign can only have one target molecule. A target molecule is selected for the project as well as the project must be in an "in development" status. A campaign describes the production of a series of reactions (e.g. master batch record) to produce some defined quantity of final material, often the active pharmaceutical ingredient used in a drug product. The design of the series of reactions to produce a material is termed a "synthetic route". Each campaign has at least one synthetic route that defines the steps to make the molecule. A synthetic route cannot be editable after campaign is approved. FIG. 28 depicts a synthetic route in accordance with the present invention. In FIG. 28, RM stands for raw material, MBR stands for master batch record, and INT stands for intermediates. Raw materials RM1 & RM2 are combined with a procedure to make up master batch record 1 that produces intermediate INT1. Materials RM3 & RM4 and INT1 are combined with a procedure to make up master batch record 2 that produces intermediate INT2 and so on until the API target molecule is produced. FIG. 29 depicts how a campaign, master batch records, and synthetic routes are inter-related.

Campaign management involves adding a new campaign and managing existing campaigns. Adding a new campaign involves providing general information, characteristic details, objectives details, and lead contacts details. Managing a campaign involves the following functionalities: adding a new campaign, searching for a campaign, viewing campaign details, modifying a campaign, canceling a campaign, removing a campaign, assigning people to the campaign and the corresponding master batch records, duplicate a campaign, deactivate a campaign, activating a campaign, and managing master batch records Add a new campaign. In order to add a new campaign, a project should be active and in "in-development" status and project—target molecule in "in-development" status. To set the status of project in "in-development" status, the user sanctions (approve) the project. To sanction the project, the user enters the sanction date while adding or modifying the project. While creating a new campaign, the user selects the project and the associated target molecule, selects project leaders, adds additional titles for lead contacts, and adds campaign objectives details. The values are entered in the appropriate fields by clicking on the lookup icon or by entering the values manually to create a new project The user can add one or many master batch records associated with the campaign. Even if material is produced at in-house production facility like a pilot plant or a kilo lab, the user formally requests for a campaign. The following fields are populated when adding a new campaign: project—target molecule, campaign name, target material, requested quantity, operating mode, characteristics-original synthetic route, and objectives-campaign objective. In preferred embodiments, when leaving any of these fields blank, the program will display an error message. For example: if the user leaves 'project—target molecule' field blank, the program will display an error message "project—target molecule is a required field. please enter a valid value." In the case where a lead contact is not selected, in preferred embodiments the program will display an error "lead contact is a required field in 1 row. please enter a valid value." The user can also save the search parameters by clicking save search. After that, the user can recall the particular search parameter by clicking load search and selecting the required search parameter. The user can choose the number of results to be displayed on the screen by selecting the required option from the dropdown menu of 'results per page'.

With the appropriate rights, the user can create, modify, remove, duplicate views for a campaign. Every view has searchable attributes and result attributes associated with it. Search screens are rendered based on the searchable attributes and results screen display values only for result attributes. However, specifying search criteria can perform a search using all the result attributes as well.

Search for a campaign. The user can search for a campaign by entering the values in the appropriate fields of the campaign search menu and by clicking on the lookup icon or by entering the values manually or leave all the field blank to search for a campaign. Campaigns can be searched using the following search criteria: campaign id, campaign name, target molecule id, and target molecule. The following fields are provided as the results of such a search query: campaign id, campaign name, project name, target molecule id, target molecule, and target material name. The user can search for a project by selecting the manage option from the campaign drop-down menu in the left navigation pane of the application. The user can select the default option from the view and enter the values in the appropriate fields by clicking on the lookup icon or by entering the values manually or leaving all the field blank to search for a campaign. The following are the search criteria: campaign id, campaign name, project target molecule, description, target material, requested delivery date, actual delivery date, requested quantity, actual quantity, original synthetic route, final synthetic route, operating mode, comments, current workflow, BO status, created date, modified date, created user, modified user, and search clear. The following results are listed campaign id, campaign name, project target molecule, description, target material, requested delivery date, actual delivery date, requested quantity, actual quantity, original synthetic route, final synthetic route, operating mode, comments, current workflow, BO status, created date, modified date, created user, modified user. By leaving all the fields blank and clicking search a list all the projects available is provided Search for a campaign—locate campaign. The user can search for a campaign by selecting the manage option from the campaign drop-down menu in the left navigation pane of the application. The user select the locate campaign option from the view and enters the values in the appropriate fields by clicking on the lookup icon or by entering the values manually or leave all the field blank to search for a campaign. click search. The following are the search criteria: campaign id, campaign name, project id, project name, target molecule id, target molecule, lead contact type, lead contact id, lead contact name, campaign status, material, original synthetic route, campaign objective, operating mode. The user can view the campaign details by selecting the manage option from the campaign drop-down menu in the left navigation pane of the application, select the view, and enter the values in the appropriate fields by clicking on the lookup icon or by entering the values manually or leave all the field blank to search for a campaign. The list of campaigns with the detail will be displayed under the result. The following are the tabs displayed in the associated campaign details page: details, characteristic, objectives, lead contacts, and master batch record. Campaign request details will remain same for all the options mentioned above. The program automatically track the following information: last modified, date when a campaign was last modified, last modified by, created date, and created by.

On clicking campaign ID, the user interested in campaign details page will be displayed. Characteristic details is the user preferred view. It means as soon as the user clicks on campaign ID the user is interested in, characteristic details screen will be displayed. The characteristic details includes the following information: original synthetic route, and master batch record. The master batch record includes the following information: batch record sequence, master batch record name, process step status, product name, product compound number, product item id, regulatory designation, synthetic route, campaign id, campaign name, target molecule, project id, project name, and target quantity.

Modify a campaign. In preferred embodiments, the user can modify requested delivery date, description, requested quantity, operating mode, original synthetic route, campaign objective, and lead contacts. In preferred embodiments, the user cannot modify project name, project id, target molecule, target molecule id, campaign id, and campaign name.

Cancel a campaign. The program will send an alert to the user that campaign is not completed yet if master batch records/batch records associated with the campaign have not started or is still in progress. When canceling a campaign, the program will display an alert that campaign is not completed yet if master batch records associated with the campaign have not started or is still in progress. On continuation, the program will display a window to enter the reason for canceling a campaign. The program provides the following list of potential reasons: adverse clinical result, adverse toxicology result, adverse lab result, low return on investment, other. Having the appropriate rights the user can also provide additional details of cancellation beyond the list of reasons in the comment field. Once a campaign has been cancelled, an e-mail alert for this new status will be sent to owners (e.g. responsible person) of the campaign master batch records, campaign site leader, campaign leader, and contacts associated with this project (e.g. development project manager, chemist). If campaign is in draft status and no work-flow is associated with the campaign, then the user can remove a campaign if it does not have master batch records/batch records associated with it.

Duplicate campaign. The program provides the following two options to perform the duplication of campaign: (i)duplicate only the campaign information without any master batch records and (ii) duplicate the campaign along with all or selected master batch records. The user should create a duplicate of campaign along with the master batch records in a 'draft' mode. The application will not duplicate the batch records associated with each of the master batch records.

Deactivate a campaign. All the outstanding workflows related to the campaign that will be impacted by this status change will be displayed. If a campaign has an active workflow, while deactivating a campaign, the program will display a warning message. On continuation, the program will display a window to enter the reason for deactivating a campaign from the sums. The program will send an alert to all the people associated with the active workflows for this campaign and all the people responsible for campaign and campaign steps.

Alerts associated with a campaign. One alert associated with a new campaign request approval alert. This alert gets triggered and sent to leaders, including campaign leader, when a new campaign request is approved. The alert message will contain the details like project id, project name, target molecule, campaign name, campaign leader, material name requested, material item id requested, quantity requested, and delivery date requested. Another alert associated with a campaign is a campaign request rejected or hold alert. This alert gets triggered when a campaign request has been rejected (or has been put on hold). The alert message will contain the details like project id, project name, target molecule, campaign name, campaign leader, material name requested, material item id requested, quantity requested, and delivery date requested. Still another alert associated with a campaign is a cancel campaign request alert. This mandatory alert gets triggered when a campaign request has been cancelled. Yet another alert associated with a campaign is a campaign modification alert. This mandatory alert gets triggered if any one of the following campaign object is modified: quantity requested or requested delivery date Unit Operation Management UO consists of statements or several actions, which describe the work that needs to be done eventually on a batch record. UO is a work instruction to perform one specific processing activity. UO is made up of one or many unit operation actions. These unit operation actions are referred to as unit actions (UA). Unit operations can be grouped together to create a template. A UO is a template which fills in (at a high level) the type of materials and equipment that might be used for a particular process. The user can setup unit operations by selecting the category of equipment or material. The program automatically generates version number for a UO once the UO is approved. Any edits after it is approved increments the minor version and the status of the UO will go back to draft.

Unit operations or templates can be used in a master batch record. A master batch record is a collection of information (such as BOMs, BOEs, general references, parameters, parameter thresholds, etc.) which is approved for various processes, and incorporated as part of a site-wide library. With the help of this library of UOs, the user can create a batch record. Advantageously, in preferred embodiments of the invention, the user must construct master batch records using only UOs that consists of approved UAs. In this manner, uniformity across synthetic schemes is ensured since all routes are using pre-approved UOs.

A unit action is embedded within the unit operation. Several unit actions might create one unit operation. A unit action provides flexibility to the user to break down a complex operations into several simple steps, and re-use those steps in other unit operations. For instance, duplicate operation of the unit operation should duplicate all the unit actions. Unit actions will use variables as placeholders to define certain types or categories of equipment, material, safety statements etc. Variables could also be critical process parameters, with their thresholds defined to ensure that the user has enough information to execute the batch record.

The variables will be detailed more when this unit action (within the unit operation) is used within a master batch record, which in turn drives the batch record/ticket view. As the unit action is detailed more and more, by the time it is used in a batch record, the parameter would be pointing to an actual equipment or material in the system (with an asset id).

During batch record creation/planning, the user can specify an actual equipment/material which might be changed (with the proper signatures) to another equipment/material due to unavailability of that actual asset id. The user should have appropriate rights to create a unit operation (UO). An approved unit operation can be created and saved in a library for reusability.

Figure 30:
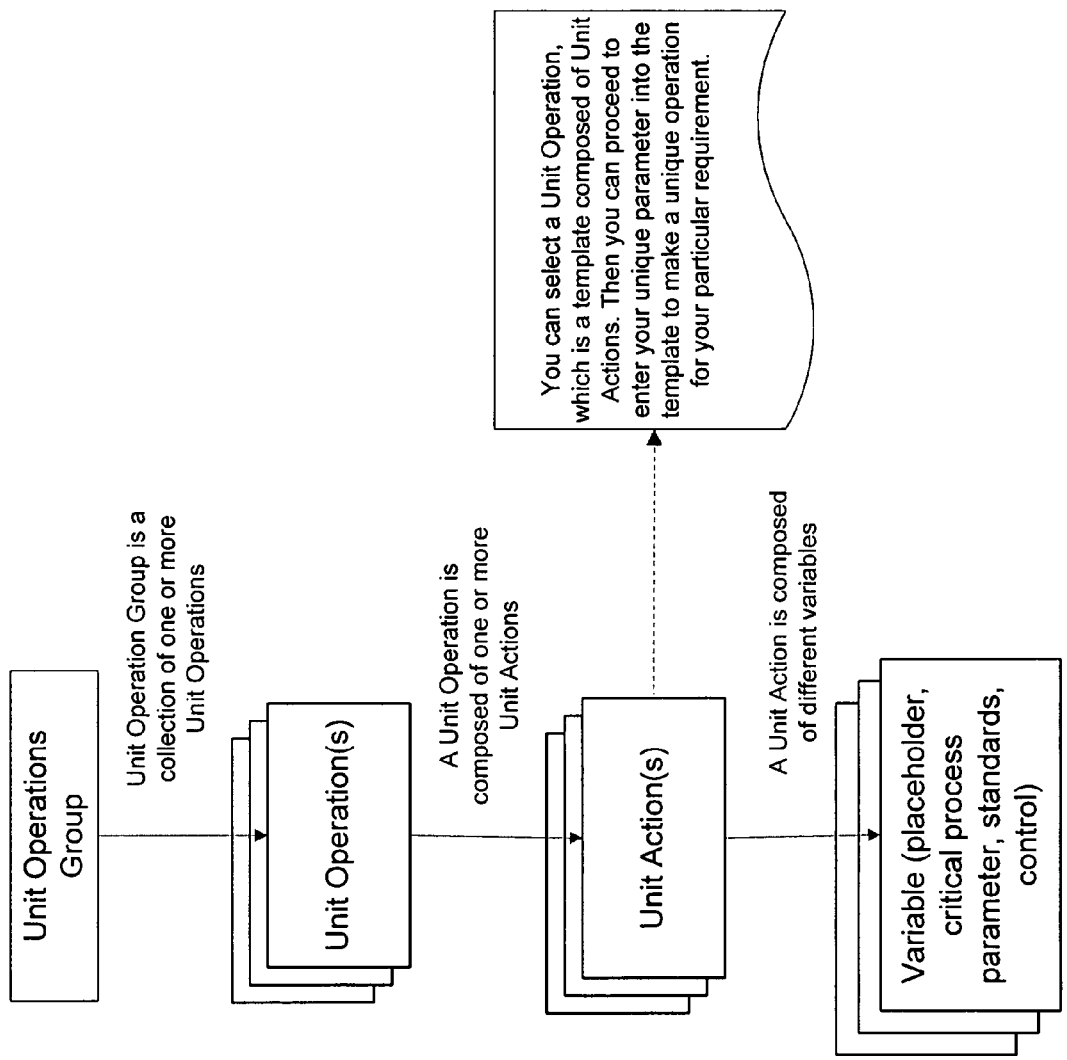
FIG. 30 depicts how the unit operation, unit operation group & unit actions are inter-related in accordance with an embodiment of the present invention.

FIG. 30 depicts the unit operation, unit operation group & unit actions are inter-related. The flow between unit action/OP all the way to the batch record execution can be described in the following manner. At the unit OP set up level, the user can choose the category of equipment & material (equipment=type like reactor, material=type like intermediate). At master batch record authoring level, the user can choose from library of unit OPs where the user can get the equation written earlier. The user can choose or re-define new variables, as well as the user can set up search attributes (lining material of the equipment=stainless steel and capacity of the equipment>30 ml) for all the variables that show up in the equation—all of these search criteria need to be captured in the PDD data. Additionally, the user selects the actual equipment and or material. At BR authoring level, the user can choose the master batch record, which was earlier approved and create the BR. The user can edit or add some information specific to the BR, and then submit for execution. At this point, before submission to the approval work flow, the user can point to the actual material or equipment available in the system and perhaps the characteristics also. The pointing to the actual material & equipment is mandatory at this step. At BR execution level, the user can read all the attributes of the equipment and materials, search for the actual equipment and material or even a sub-ticket or batch record the user like to use (if the equipment & material specified at the BR authoring step is not available, then they would specify alternate ones) and record the measurements for the new equipment and the material the user is making.

Library management. The user can create and save unit operations in a library. The user can add a unit operation to the library, search for a unit operation, view unit operation details, modify a unit operation, remove unit operation, duplicate unit operation, activate unit operation, deactivate unit operation, and add unit operation. The user can create a unique unit operation (UO) that can be saved, searchable, and usable in authoring a master batch record, and ultimately in a batch record. The user can also flag the UO to indicate if electronic signature is required. A unit operation is composed of one or more unit actions (UA). When creating a unit operation the user can determined whether the to associate a subticket with it or not. A sub-ticket is a type of ticket or material being requested on a master batch record (e.g. create buffer, create media) that is going to be performed by a different group. Variables will be used within unit actions to reference sub-tickets within the system. For subtickets outside the program, the program will provide a means to capture it as a free text (in setup of UA). The user can further define order (e.g., "u0a") to indicate the ordering of the unit actions (UA) within a UO). The user can further provide a unit action description which shows up in the summary unit action context table above the unit action editor. Here the user can write a description for each unit action in 'unit action description' text field. In general, a second person can be specified in a UA to ensure that someone looks at the unit action being executed and sign off on it. For each UO action, the user can flag whether the UO action requires second person verification. A unit action can be authored using a text box provided by the present invention. The user can type in all the steps needed to perform the unit operation, insert tables, and do some simple formatting within the text box. For instance, in some embodiments of the present invention, the user can insert control variables to be measured (control variables are input fields such as pressure, temperature, volume) when operators are executing batch record. The user can further provide one or more placeholders <variables>to denote either equipment or material, which would later on be matched to actual equipment or material. The user can further provide references to standards (hazards, job aids, cautions, abbreviations, etc.) which would be expanded to the description at the time of printing. The user can further provide references to assays that would need to be run against a material sample—those assay parameters would be printed as is in the final print out. The user can also provide detailed instructions on how to perform certain operations as part of the process of creating a new API (once the user have written out each instruction, the user can reference those variables anywhere in the collection of instructions).

Once the user organizes an individual unit actions, then the user can save the unit operation and continue working on it until all the parameters, variables etc. have been defined completely. The unit action can then be submitted to a work flow. Once completely approved by QA/QC and other affected groups of users, these unit operations can be re-used to create templates or directly be used in master batch records belonging to the project/campaign.

A new unit requires the following values: unit operation name, operating mode, unit operation type, functional purpose. In addition, the notification group field becomes mandatory if the user select 'yes' for subticket. The alert will be sent to this notification group while the BR is executing.

The user can search for a UO using the same techniques used to search for campaigns and projects. With the appropriate rights, the user can create, modify, remove, duplicate views for a unit operation. Every view has searchable attributes and result attributes associated with it. Search screens would be rendered based on the searchable attributes and results screen would display values only for result attributes. However, specifying search criteria can perform the search using all the result attributes as well.

The user can modify a unit operation when status=draft or approved. Modifying a unit operation includes the UO actions and UO general fields with the exception of 'unit operation id' and 'status'. Modifying an approved version of a unit operation creates a new revision of the UO record if UO status=approved. The user can modify a UO action during the creation of a UO. The user can change variables or text of the UO action.

UOs can be removed, duplicated, activated, and deactivated in the same general manner as campaigns and projects.

In preferred embodiments of the present invention, any UO can be deleted if and only if it is not used in any UO template, master batch record or batch record and its state is draft. When unit operation is being approved, the program will increment the version to a whole number. Only approved UOs can be used in UO template, master batch record and batch records. When a UO in draft state is modified, there is no change in its state. When a UO in approved or rejected state is modified, the state of the UO is changed to draft and the minor version on the UO is incremented by 1. When UO in draft, approved or rejected state is duplicated, a new UO is created in the draft state with 0.1 as it version.

Alerts associated with UO. An alert is triggered when the unit operation is created or when the version of the unit operation is changed. The ticket author group is a role that is set up, with associated users. The program sends an alert to all users within that role. The program sends a non-mandatory system alert to team leads, including ticket authoring group. QA/QC groups should also receive a notification. A non-mandatory alert gets triggered when a new unit operation has been approved. The alert message will contain the details like unit operation name, unit operation id, creation date, and version number. A non-mandatory alert gets triggered when a unit operation has been rejected. The alert message will contain the details like unit operation name, unit operation id, creation date, and version number.

Unit operation group management. The user can create a group from any combination of the existing unit operations available in the BR cores library. With administration rights, the user can create a group consisting of a group of logically connected unit operations. A group of unit operations is a pre-defined sequence of unit operations to perform a major production process. This group is independent of projects and is more for user convenience. A group is created, archived, and reused to create master batch record quickly.

Unit operation group library management. A user can add a new unit operation group to a library. Adding a new unit operation group involves the following functionalities: general information and details. The user can manage a unit operation group in the library. Managing a unit operation group involves the following functionalities: adding a unit operation group, searching for a unit operation group, viewing a unit operation group details, modifying a unit operation group, removing a unit operation group, duplicating a unit operation group, activating a unit operation group, and/or deactivating unit operation group. The user can build a group from one or many unit operations by combining the existing unit operations available in the BR cores library. The user can provide the description of unit operation group in 'UO group description' field. The user can search for a UO by specifying any of the following search criteria: UO group type, UO group description, UO group name, UO group id, effective start date, effective end date, is active, created date, modified date, created user, modified user. The following are the column lists provided in the search results window: UO group type, UO group description, UO group name, UQ group id, effective start date, effective end date, is active, created date, modified date, created user, and modified user.

Master Batch Record Management

Figure 31:
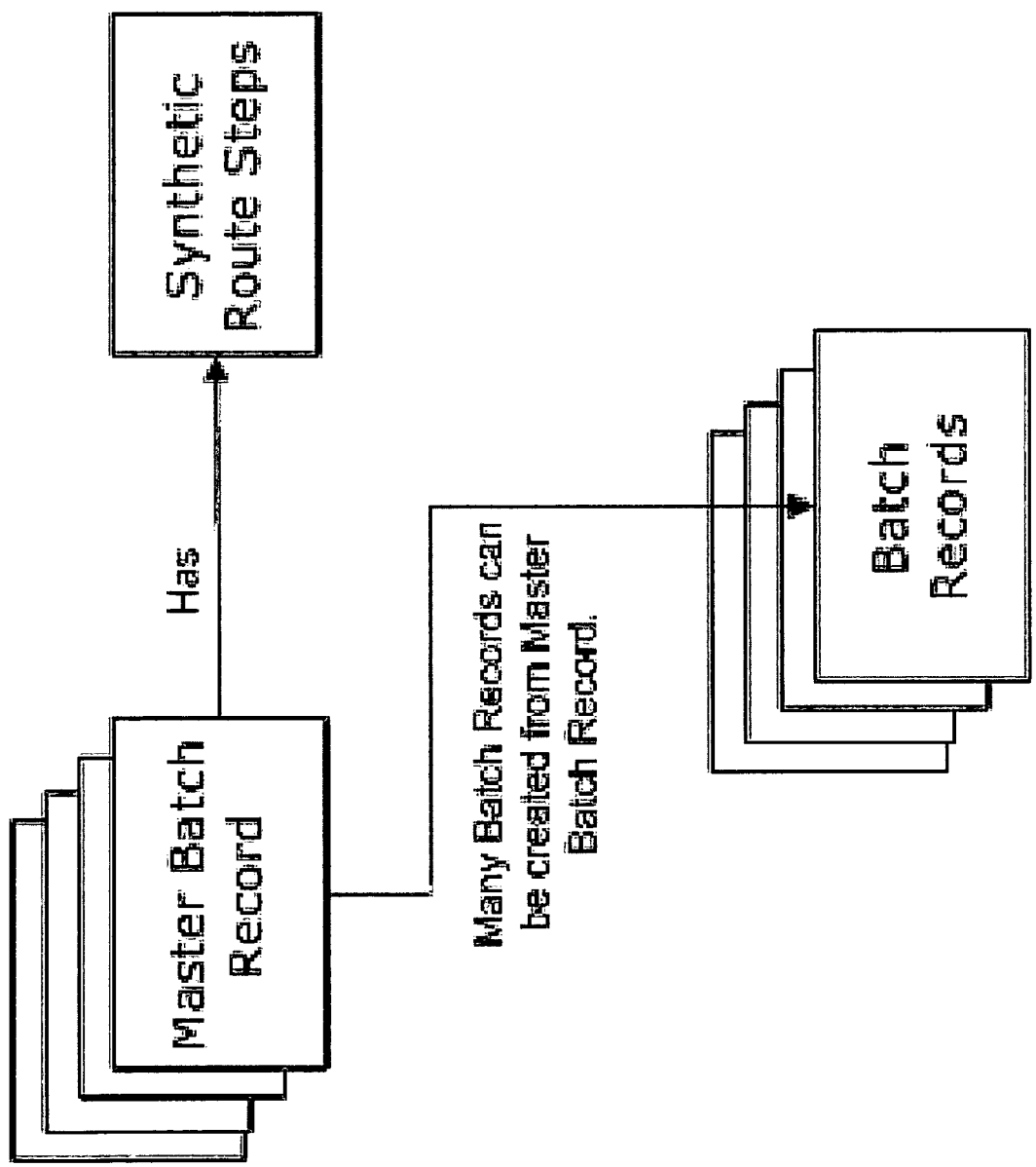
FIG. 31 depicts the inter-dependencies of various elements in master batch record in accordance with an embodiment of the present invention.

A master batch record is the data associated with the process within the inventive program. A master batch record gathers and defines all the information needed to create a working batch record eventually regardless of location or site or personnel. FIG. 31 depicts the inter-dependencies of various elements in master batch record in accordance with an embodiment of the present invention. The collection of data that is needed to define the master batch record is a BOM (bill of material), BOE (bill of equipment), BOA (bill of assays), BOP (bill of process), and references to various procedures/safety statements etc. Once the master batch record is defined/created, it needs to be approved (if going to be used in a BR that is governed by good manufacturing practice (GMP)) and placed in a library to be re-used by other users who are going to create a batch record. Advantageously, the master batch record is built up by the user from a set of unit operations created as a separate step and available in a library of unit operations. The unit operations are used in a particular order within the master batch record. The references to material/equipment/statements, parameters etc. from within the unit operation will be brought into the master batch record being created and displayed in the BOM, BOE, references, parameters sections respectively.

When creating the master batch record, the user can also choose to edit the lists of equipment, materials etc. or bring in new lists, or individual items. In general, the master batch record is the place where the user collects all the series of actions or operations. A master batch record represents a chemical reaction that produces a product (e.g. an isolated intermediate) and some by-products or wastes. A master batch record comprises a bill of process, scaled bill of material, step bill of equipment, and bill of assays. The bill of process (BOP) is a collection of unit operations that the user can select from the library to use within the master batch record. Along with the BOP. The user also needs to specify the equipment and materials the user would be using. The program provide "type of materials used" and "type of equipment used", which lists BOM and BOE respectively. The program also provides options to add other material or equipment from the library on an ad-hoc basis.

The BOP is the heart of the master batch record, and will provide the order in which unit operations would be executed. The user can provide references to safety statements, caution statements etc. that would need to be used in this master batch record context. The bill of material is part of the core component that defines the list of materials that that is required to make some quantity of a product. If the user decides to start creating the BOM by first specifying the list of operations (BOP), then there are some options to populate the scaled BOM tab within the master batch record. The program provides a scaled BOM tab that is auto-populated with the materials used already in the operations specified earlier. In addition, the program allows the user to import a previously created & approved master BOM to create the master list of materials that might need to be used as part of the operations. Also, the program allows the user to add ad-hoc individual materials. Additionally, for convenience, the program allows the user to save the list created on the scaled BOM tab to a new version of a master BOM (or a new master BOM).

The BOM list can be changed if required at the master batch record creation step, or at the batch record authoring (to create the planned BR) step or at the BR execution step. The approval process for the BOM is part of the approval process for the master batch record itself. The BOM does not stand independent of the master batch record.

In addition to bringing in the master BOM list, the program provide the ability to scale the BOM list up or down, based on the target quantity of the API being produced. The user can do the scaling at this early master batch record authoring stage, because the target quantity of the material being produced at this time is known. The scaling factor, as well editable fields need to be provided to scale the individual quantities of the materials specified on the BOM tab.

Once the material list is acceptable to the user, the user can reference those items in the operations on the BOP tab. The user can point to these materials through the concept of "variables" within the unit operation.

The step bill of equipment (BOE) is a list of equipment associated to a master batch record. A step BOE is optional. The program provides users the flexibility to create the step BOE at the time of master batch record planning. Step BOE cannot be a standalone-it has to be associated with a master batch record.

The bill of assays (BOA), like BOM or BOE, brings together all the assays (tests) that will have to be conducted on the material being produced by the master batch record or BR. Each of the assays in the BOA will have their respective thresholds as defined in the unit operations (they will be defined as assay parameters, similar to control parameters). BOA is similar to a 'dashboard' view of the assays s (it is not a collection of assays that are repeatedly performed hence needing a grouping function). It helps in scoping the effort required from analytical chemists. It also serves as a reminder on which tests are planned and which ones got executed, and what the results were. It will also help print out the separate assay section at the end of the batch record printout.

To add a new master batch record the following is defined: general information, characteristic details, lead contacts details, BOP, scaled BOM, step BOE, and BOA. Managing master batch records includes: searching for a master batch record, viewing master batch record details, modifying a master batch record, removing a master batch record, activating a master batch record, deactivating a master batch record, adding a batch record, managing a batch record, reserving a BOE, and adding a new master batch record. While adding a master batch record, the user can specify general information, characteristic details, lead contacts details, BOP, step BOE, and scaled BOM in order to generate the batch record. The user can view the list of assays under BOA after adding BOP, scaled BOM, and step BOE and clicking on tab BOA.

A user can select the point of insertion of a new unit operation into a MBR. Further, the user can add, remove, modify unit operations, unit operation group in a MBR. The program allows the user to associated a subticket with a MBR. Sub-tickets are a type of ticket or material being requested on a master batch record (e.g. create buffer, create media)—that is going to be performed by a different group. Variables are used within unit actions to reference sub-tickets within the system. For subtickets outside the program, the program will provide a means to capture it as a free text (in setup of UA). The user needs to specify (within the master batch record) the following: the unit operation with a "trigger sub-operation" set to yes, the material that gets made by a sub-ticket on the BOM tab (buffer, media) etc.—these materials should exist in the materials library, without a lot# and amount=0, and add scaled BOM. The program provides a mechanism to plan for all materials needed to deliver total target quantity for a master batch record, through scaled BOM. The user should create scaled BOM for each master batch record. The program supports the following methods for creating a scaled BOM: (i) import available master BOM that is associated with the master batch record. 'scale factor for a lot' will apply, (ii) select an existing master BOM. 'scale factor for a lot' will apply, (iii) select materials and build a new scaled BOM using the scale factor per lot. 'scale factor for a lot' will not be available (user will have to manually calculate quantity). If a master BOM is referenced when creating a scaled BOM, the program will estimate the required materials by multiplying the master BOM 'target quantity' by a scale factor to arrive at the total 'scaled quantity'. The 'total quantity' of the scaled BOM is derived by multiplying "scaled quantity" and the "plan number of lots" for a master batch record. the user can edit both quantities: 'scaled quantity' and 'total quantity'.

For each material line item selected, the user can locate the spec plan id that is used to evaluate lots associated with the listed material line item. Additionally, the user can free-text materials that might not have been added to the material library yet. The user can add one or more pieces of equipment to the BOE. For each such piece of equipment, the user can: enter a cleaning limit, provide comment, or enter "other equipment".

When adding a new master batch record, the following fields are populated: campaign id, , master batch record sequence, master batch record name, target product name, item id, target quantity, regulatory designation, and synthetic route. When adding characteristic details, the following fields are populated: expected yield, target start date, target end date planned number of lots. When adding lead contacts, the following fields are populated: lead contact type and contact name. When adding scaled BOM, the following fields are populated: per lot quantity, total quantity, and specification play.

The program allows a user to create an allocation directly from the scaled BOM. The user can select one or more material line items listed on the scaled BOM. The listed "total quantity" of the line item on the scaled BOM default is the allocation request quantity. The program allows the user to edit the allocation request quantity. The program provides a summary of the allocated materials for each scaled BOM of a master batch record. The program will provide the following information: material name, material item id, total quantity, current requested quantity, quantity procured, quantity allocated, quantity available. The program will allow an authorized user to manage allocation request from the scaled BOM. The user has full capability of managing allocation for each of the line item.

The program enables an authorized user to reserve either the entire step BOE or individual pieces of equipment listed in the BOE. While reserving the equipment through a of step BOE, by default the program will display the master batch record estimated start and end date for the reservation duration in the 'reservation start date' and 'reservation end date' fields respectively. The user can change the reservation either at the step BOE level or for each individual piece of equipment. Each reservation is for a single site. The user can reserve equipment while editing the BOE. When reserving the equipment through step BOE, the following fields are populated: reserved for—user id, reservation site—site id, reservation start date, and reservation end date. Managing a reservation from step BOE involves the following functionalities: add a new reservation, cancel reservation, edit reservation, lock reservation, unlock reservation. while adding a new reservation the following fields are populated: reserved for, reservation start date, reservation end date, reservation site, purpose (e.g., cleaning, process, maintenance). If the user selects the cleaning option, then the program will prompt for the batch record. If the user selects the process option, then the program will prompt for project target molecule (project target molecule field is mandatory) and batch record (batch record field is non-mandatory). If the user selects the maintenance option, then the program will prompt for maintenance type (maintenance type field is mandatory), work order number and final due date (work order number and final due date fields are non-mandatory).

Advantageously, the program provides a view of the state of readiness for equipment listed on the step, production, or planned BOE. The program provide the following information on clicking check suitability option: equipment id, equipment status, product name, master batch record sequence, lot number, synthetic route, end date, recorded value, required cleaning limit(mg/l), meets cleaning limit, and result. The user can search for a master batch record with the following different views: batch record details, default, equipment cleaning history, equipment process history, lead contact quick search, locate by material BOM, master batch record BOE reservations, master batch record details, and product name quick search. Master batch record details is the user preferred view. Fields under locate master batch record and column list under result will vary from view to view. If the user want to further narrow the scope of search, then in the results screen the user will click on the filter icon and select the fields with appropriate values. The user can also save the search parameters by clicking save search. After that the user can recall the particular search parameter by clicking load search and selecting the required search parameter. The user can choose the number of results to be displayed by selecting the required option from the dropdown menu of 'results per page'. With the appropriate rights, the user can create, modify, remove, duplicate views for a master batch record. Every view has searchable attributes and the result attributes associated with it. Search screens would be rendered based on the searchable attributes and results screen would display values only for result attributes. However, specifying search criteria can perform search using all the result attributes as well.

In some embodiments, the user can view master batch record details by selecting the manage option from the master batch record drop-down menu in the left navigation pane of the application. The list of master batch records with the details will be displayed under the result. The following are the tabs displayed in the master batch record details page: details, characteristic, lead contacts, BOP, scaled BOM, step BOE, BOA, and batch record. The master batch record details will remain the same for all the options mentioned above. When clicking master batch record name, the master batch record details page will be displayed. Characteristic details is the user preferred view. When the user clicks on master batch record name of interest, characteristic details screen will be displayed with the following details: manufacturing site, site id, description, expected yield, target start date, target end date, planned number of lots, and comments.

Once a master batch record has been associated to a campaign, the user cannot change the association of the master batch record to the campaign. The program will display a warning message to the user if there is a new version of the referenced master BOM, at the time of saving. In preferred embodiments of the present invention, a user can remove the master batch record if all the following conditions are true: a batch record has not been created against the master batch record., material allocation request has not been made for the master batch record, equipment reservation has not been made for this master batch record, the master batch record is not completed yet. If BR is cancelled, it can be removed. With the appropriate rights, the user can duplicate all the info from the original master batch record (including BOMs, BOEs, and BOPs) and make it available as a new master batch record. This saves time and make all master batch records consistent. For example: a master batch record "mbr1" which is a part of a campaign "c1" can be duplicated to become "mbr1" of another campaign "c2". It need not be restricted to duplicating under one campaign.

A master batch record can be deactivated if there is no planned BR related to it. If a master batch record has been deactivated, the user cannot initiate any new workflow against this master batch record. The program will warn the user of this behavior and provide a list of workflow associated to the master batch records that are still in progress. On continuation, the program will display a window to enter the 'effective end date' and 'reason for change' for deactivating a master batch record.

A master batch record can be activated. The program will display a window to enter the reason for activating a deactivated master batch record from the sums. In response, the user should enter <effective start date> and enter the reason for activating the master batch record in some embodiments of the present invention.

The status of a master batch record can be changed. Change status will allow the user to change the status of the selected master batch record manually. Changes in the status can be either driven by workflow or the user can change the master batch record status manually by selecting an option on clicking the 'set status' button.

Alerts associated with master batch record. Alerts can be generated when a master batch record is either submitted for approval or approved. Such an alert gets triggered to warn team leads, including campaign leader, batch record authors, and QA/QC groups that the master batch record is being submitted for approval, approved, rejected or kept on hold. If master batch record status equals submit or approved, then a alert message such as "the master batch record has been submitted or has been approved." can be triggered. The alert message will contain the details like project id, project name, target molecule, campaign name, campaign leader, master batch record name, and master batch record id. If the master batch record status equals reject or hold, then an alert message such as "the master batch record request has been rejected (or has been put on hold)." can be triggered. Such an alert message will contain the details like project id, project name, target molecule, campaign name, campaign leader, master batch record name, and master batch record id.

Validate master batch record. The program provides a validate function for the master batch record which calls common code used by the master batch record before submitting to a formal workflow. This validates the BOM, BOE used on the BOP and provides a consolidated list of errors (or provide a red asterisk and a set of comments next to the field that has issues). The program will display a warning message: if equipment or materials used on the BOE/BOM have a status of non-qualified, if they have a status of unavailable or non-qualified for equipment, if they have variables being used in the master batch record that is not bound to any equip, materials. In addition, a window will pop up to allow the user to match the variables with the right equipment or material. For example: check <pressure> without pressure being bound to equipment—this is not allowed. The user has to qualify the "control" parameter called "pressure" with its appropriate equipment or material. The program will validate the "operating mode" of the equipment as per the master batch record operating mode. In general, a sweeping validation of the master batch record can be enabled using this special "validate" button.

Batch Record

Figure 32:
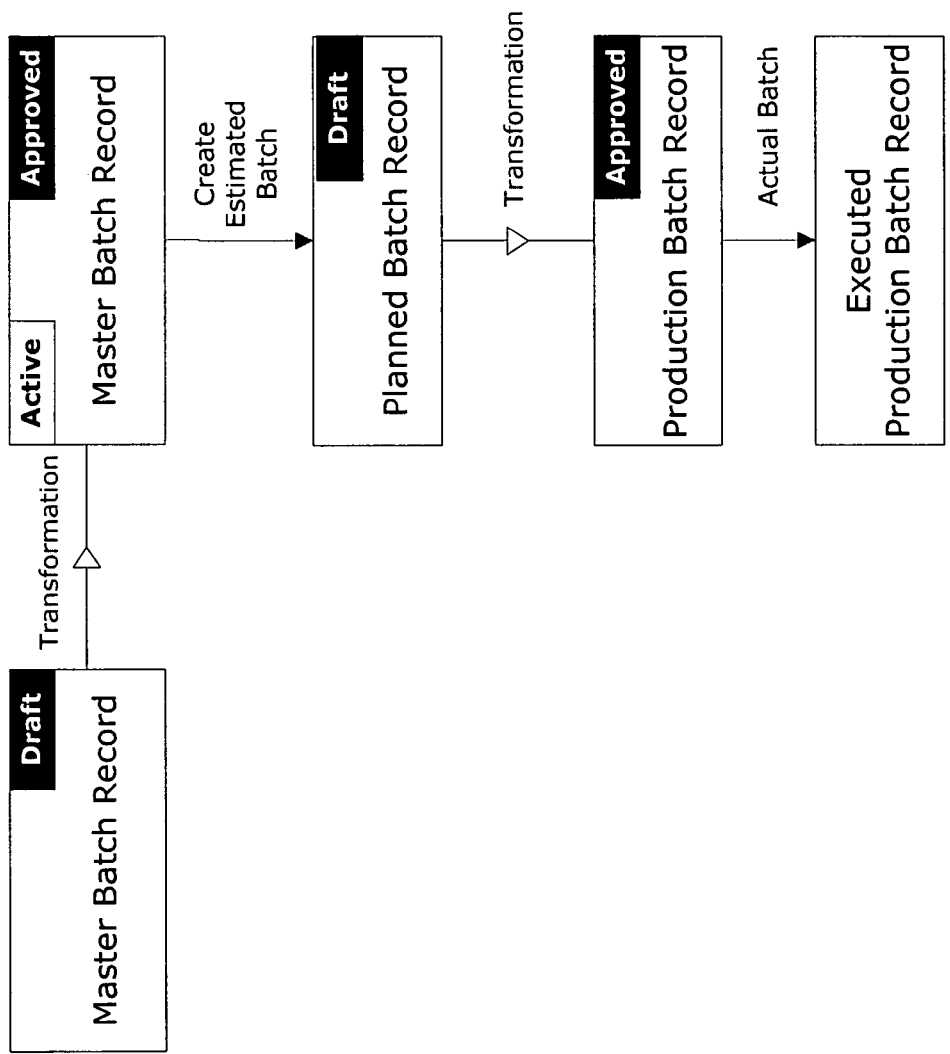
FIG. 32 depicts the different phases of a batch record, in accordance with an embodiment of the present invention.

Batch Record is part of the formal process that is required to create a target compound or a lot of a particular Material. In other words, batch records are the produced lists of all the materials, equipment, and master batch records that go into making a batch lot. There are four phases in batch records: master BR, planned BR, production BR, and executed production batch record. The master batch record is a template by which a user creates the planned batch record. Planned batch records are estimates of what it takes to build a batch of material. Production BR are approved planned batch records generated within the program. An executed production BR is an actual batch record, which the user can draw out by executing the production batch with the actual values for BOM (Bill of Material), BOE (Bill of Equipment), BOP (Bill of Process), and BOA (Bill of Assays). FIG. 32 depicts the different phases of the batch record.

Planned batch record. A planned batch record comprises a planned Bill of Process (BOP), planned bill of material (BOM), planned bill of equipment (BOE), and planned bill of assays (BOA). A user can add a planned batch record by adding the general information, planned BOP, planned BOM, and planned BOE. For each planned batch record, the BOM inherited from the master batch record will be the planned BOM. A user can add or remove materials from this BOM. Anything added to the planned BOM directly will not be updated in the process step BOM. If material lots have been allocated to the master batch record, the program will copy over any lots and containers allocated for a material in the process step BOM and create the planned BOM. The program can let the user select the lots and containers for individual materials and add them to the planned BOM. If the batch record is a cleaning batch record, the program will default a blank planned BOM. The user will need to add material that is needed for cleaning. If material lots have been allocated to the master batch record, the user can select the lots for planned BOM.

For each batch record, a planned BOE including "Other Equipment" will automatically be created from the step BOE of Master Batch Record. In the case of a cleaning batch record, if the user creates an ad hoc with no association to a master batch record, the planned BOE will be blank when created. The user will have to locate and add equipment to the BOE. If BR operating mode=GMP, the program will add GMP equipment. A user can modify a planned BOM if the batch record is in 'draft' or 'submitted' status. A user can modify 'remove material'. If material is removed, any lots associated with material will also be removed. A user can also modify 'add material', 'associate inventory', 'estimated quantity', 'other materials', and 'spec plan ID' fields. The program will verify that the lot selected has been evaluated against Spec Plan ID. A user can modify 'add equipment', 'remove equipment' (hard delete), 'cleaning limit', and 'other equipment' fields. The step BOE will not be able to capture any updates to the equipment list if the changes are completed at the planned BOE level.

The procedure to modify planned batch record is to validate material in the planned batch record. The program will display and validate the state of the lot/container which is being used in the planning phase. The user can select one or more lots/containers from the BOM. The program displays the following information about the selected lot/containers: material name, lot number, lot expiry date, container number, supplier name, qualification status (of the vendor), manufacturer name, COA received, TSE received, spec plan id, re-evaluation date, and lot/container release status The creation of a production batch record implies that the approved planned BOP, planned BOM and planned BOE will be cloned to create a "production" version. If workflow is associated with creation of batch record, workflow will automatically move the batch record to an "approved" status. This will generate the production batch record. A batch record has to be paired with a BOP, BOM and BOE. Consequently, planned/production BOE and planned/production BOM will not have unique identifiers associated with them. Instead, both planned/production BOE and planned/planned BOM will use the batch record as a reference. Planned batch record and production batch record should be transparent and seamless. Both planned and production batch records will contain the same header information.

When a batch record is approved and batch record is in the 'approved' status, the program will automatically clone the planned BOP to create a Production BOP. Once the planned BOP is approved, the user cannot edit Planned BOP. When a batch record is approved and batch record is in the 'approved' status, the program will automatically clone the planned BOM to create a production BOM. In preferred embodiments of the present invention, all materials must have a spec plan identified in order for the planned patch record to be approved. The program verifies that a lot added to a production BOM is released. Once the planned BOM is approved, the user cannot edit the planned BOM.

The program will automatically place the materials used in the variables into the BOM tab and also perhaps provide an icon to show that the items were 'derived' from unit actions as opposed to added manually. When a batch Record is approved and batch record is in the 'approved' status, the program will automatically clone the planned BOE to create a production BOE. Once the planned BOE is approved, the user cannot edit the planned BOE. If BR operating mode is equal to GMP, the program can only add GMP equipment.

Modifying a production BOM. A user can add certain equipment, like scales and other portable equipment only at the time of use. Therefore, the user needs to update the production BOE with this equipment that is not listed on the planned BOE. A user can locate the BOE and then locate the equipment to add. The program will allow the user to remove (hard delete) the line item on the production BOE. The user can edit the start date. However, the program will verify that the 'start date' is not before the 'production batch record start date'.

Validate material in production batch record. The program displays and validates the state of the lot/container which is being used in the planning phase. The user can select one or more lots/containers from the BOM. The program displays the following information about the selected lot/containers: material name, lot number, lot expiry date, container number, supplier name, qualification status (of the vendor), manufacturer name, COA received, TSE received, Spec Plan ID, re-evaluation date, and lot/container release status. Validation ensures that the vendor of the material is qualified, and that the lot has not expired. These situations will lead to the product throwing up an error.

Verify user has read safety standards. The program will ensure that everyone accessing the batch record has read the safety statements found in the batch record at least once. If the program detects that the login user has not read the safety statements, then it will display the summary of safety statements for the user to read. The user must acknowledge reading the safety statements.

Search for a Batch Record. A user can search for a batch record with the following different views: BR Quick Search, default, locate BR basic, and locate BR default. Locate BR default is the user preferred view. Fields under search batch record and column list under result will vary from view to view. If a user wants to further narrow the scope of search, then in the results screen, the user can click on the filter icon and select the fields with appropriate values. A user can also save the search parameters by clicking save search. After that a user can recall the particular search parameter by clicking load search and selecting the required search parameter. A user can choose the number of results to be displayed on your screen by selecting the required option from the dropdown menu of 'results per page'. With the appropriate rights, a user can create, modify, remove, or duplicate views for a batch record. Every view has searchable attributes and result attributes associated with it. Search screens are rendered based on the searchable attributes and results screen display values only for result attributes. However, specifying search criteria can perform search using all the result attributes as well. The following are the search criteria: batch record ID and lot number. The following are the column list under result: batch record ID, batch record type, lot number, product name, and product item ID. A user can search for a project by selecting the manage option from the batch record drop-down menu in the left navigation pane of the application. Select the default option from the view. Enter the values in the appropriate fields by clicking on the lookup icon or by entering the values manually or leave all the field blank to search for a project. The following are the search criteria in this view: batch record type, operating mode, process step, comments, planned batch record, responsible person, implementation site, max expected quantity, batch record id, min expected quantity, current workflow, BO status, created date, modified date, created user, and modified user. The following are the column lists under result for this view: batch record type, operating mode, process step—process step name, campaign, material output type, comments, planned batch record responsible person—user id, implementation site—site id, maximum expected quantity, batch record id, minimum expected quantity current workflow—process instance id, BO status—status id, created date, modified date, created user—user id, modified user—user id,

PCM

PCM is the underlying platform that supports SUMS's and it has nine major service components: organizational management, people management, administration management, workflow management, alert management, meta modeling, audit trial, general administration, and security.

Organizational management. Every company has an organizational structure through which each personnel interacts with the other. PCM supports this by creating the organizational structure that will streamline the communication and track the progress of the works. For example, the administrator will create a company and assign a site to it.

People management. Employees with various designations use this application. And then there are external companies which are associated in different capacities like supplier, distributor, transporters etc. This functionality helps to keep adequate information of the people who use this application and that of the external contacts. For example, the administrator creates a user or vendor and records the vital information like the address, contact number, profile etc.

Administration management: With this functionality, the administrator can initialize and manage cache by module functionality. The administrator can also set the preferences like language, currency, time zone, time format etc., according to the local needs.

Meta modeling. The data modeling functionality is primarily expressed in its meta modeling capability whereby the Administrator can create new business objects.

Workflow management. A typical user will want to create workflows to make the job easier. In an examplary process there may be three people involved, a boss, the bosses' boss, and the bosses' bosses' boss, all who get the request from a worker to either approve or disapprove a process or work. So the administrator creates a workflow for your process. Then, when the boss gets a request it's just a simple matter of checking either approval or disapproval. When the boss approves or disapproves, an e-mail is sent to all the concerned person in the chain.

Alert Management: Using the alert management tool, the administrator triggers alerts for the user. For example, an alert is sent to all users of a company when a new site is added.

Audit trial. PCM provides audit trails on key functions thus meeting regulatory requirements. For example, whenever anyone goes in to make changes an attribute, say the boiling point attribute on a piece of equipment, that change will be logged in and kept in audit trial table.

Integration services. The application provides webservice integrated framework, which invokes external web services and plugged-in custom-built web services. In some embodiments of the present invention, the integration is XML based and all the communication between SUMS and external application takes place in XML format.

Authorization. At the time of creation of a business object (BO), the author of the BO can specify if the user would want to restrict the edit and delete privileges to specific users. If the author does not enter any user then the BO can be edited or modified by anyone that has the privilege to (via role) to edit/delete the BO.

The following is a table which gives a quick reference to what PCM as a platform provides required services to SUMS.

| PCM CORE SERVICE | CONFIGURE SUMS. |
| --- | --- |
| Organizational Management | Create an Organizational structure. Example: create a department which is hierarchically associated to company and location. |
| People Management | manage user profiles. Users can be both internal and external people of the company. Example: Create user/contact ID, maintain their details like contact number, education qualification, photo identity etc. |
| Administration Management | Create and manage organizational information including company, department, sites locations. |
| Meta Model | Create new categories with new attributes. Example: create a new API material with new properties. |
| Workflow | Create a new workflow. Example: automate a five-step approval process. |
| Alerts | Create new alerts that are part of a workflow process. Example: After every step of a workflow process, have an alert sent to the workflow process owner. |
| Workflow Management | Create a new workflow. Example: Automate a five-step approval process. |
| Audit Trails | Provides records of certain key events, possibly to fulfill legal requirements. |
| Security | Keeps the SUMS data secure. |
| Integration | Allows SUMS to link to other applications. |

Business objects. A business object (BO) abstracts the entities in the domain. Entities are concepts that are pertinent to a domain. For example, "material" is an entity business object and from it are derived a chemical material, an API, a raw material, etc. A user can create new object types within these categories. All categories created for a given database points to a default BO called default. Hence, a BO can be defined as an assortment of categories. It consists of a primary driver category, and a group of categories that come together to describe a BO, such as, project, library, campaign, batch record, user, etc.

BOs are organized in a hierarchy as in a "process". A BO may have children BOs, such as, project, campaign, batch record, process step, BOM, BOE, etc. A BO is characterized by a business object ID (BO ID), a BO name, a parent BO, an alert view, a workflow view, etc. Each BO can have several statuses with a status ID, status name, description and delete operation (indicating whether a BO is allowed to be soft or hard), this field is used internally by the application to perform certain validations. A BO can have only one active workflow associated with it at any point of time. The above status fields also play an important role as part of workflow definition as each BO with, for example, status1 being moved to the next state (status2) thus driving the workflow ahead.

Figure 36:
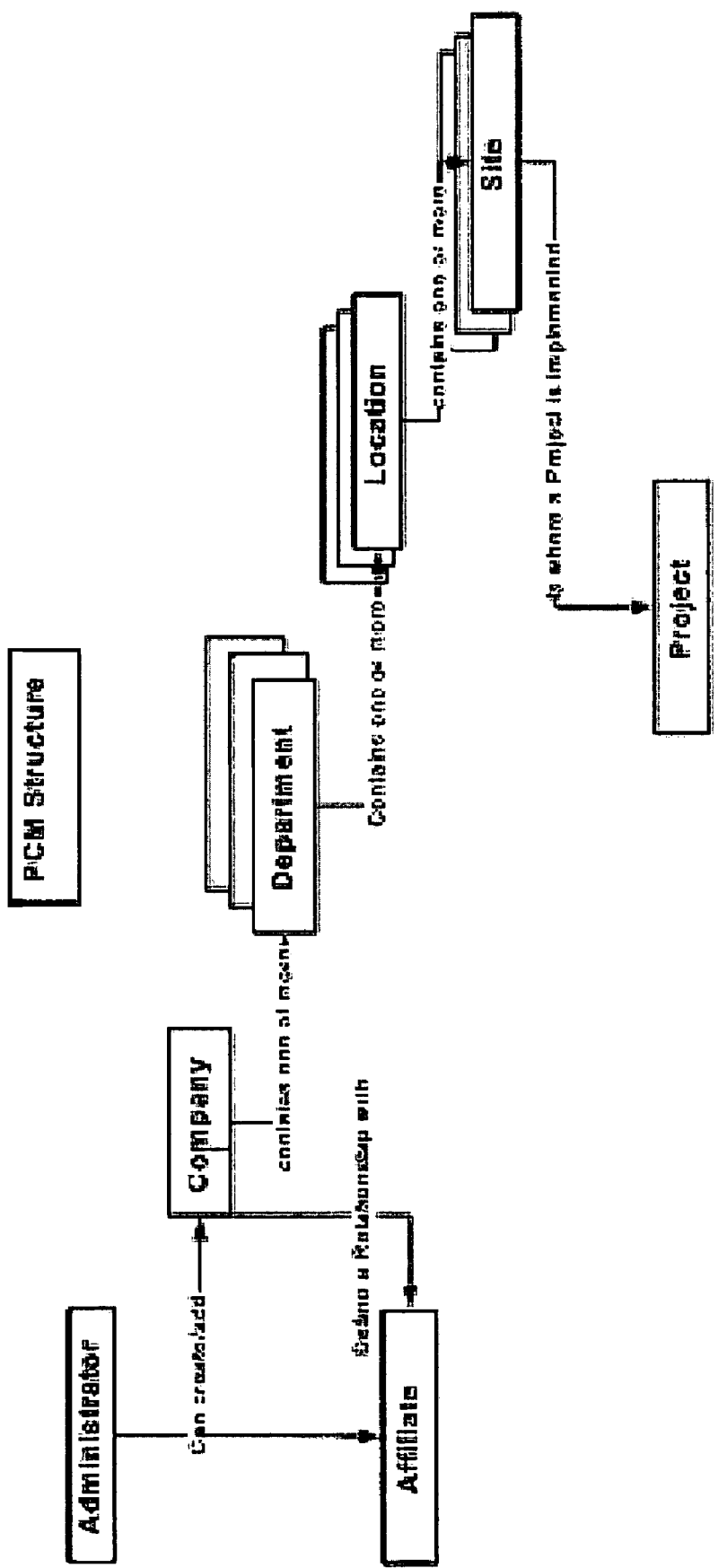
FIG. 36 illustrates the organizational structure of a PCM in accordance with an embodiment of the present invention.

The organizational structure of PCM in accordance with an embodiment of the present invention is depicted in FIG. 36. All companies have an organizational structure and the user too can create one. PCM has four major organizational structures, which are interdependent. That is, a site cannot exist without a company and a company cannot be created without having a default site. The four major organizational structures are: a company, a department (only within a given company, not for external companies), a site (only for a given company, not for external companies), a location (only for a given company). A user can add, modify, duplicate and remove the above organizational elements only with administrator rights in preferred embodiments of the present invention. Note also that there can be multiple companies in an organization. And each company can be made up of one or more sites and each site may comprise of one or more locations. Note also that there can be multiple companies in an organization. And each company can be made up of one or more sites and each site may comprise of one or more locations.

Meta Models

An advantageous feature of the present invention is its meta-modeling capability. This meta-modeling ability allows a user to modify program categories and their attributes. Within the meta-modeling category, the following folders are provided: meta model, system, environment, equipment, material, and process. Within each of these folders are business objects that are related to the folder category. For example, within the equipment folder are the following equipment business objects: blender, column, dryer, evaporator, filter, hood, pH meter, reactor, tank, pump, scale, scrubber, sieve, syrup can, temperature controller, vacuum meter, cyromat, distributed solvent system, flow chart, HVAC system, infrared analyzer, mass flow volume density meter, mill module, nitrogen system, purified water system and thermal fluid system. A business object is a classification of a common piece of equipment with the same characteristics. For example, a user can create any number of blenders, columns, dryers, etc. In addition, a user can add their own characteristics (attributes) to each equipment type. An example of blender characteristics (attributes) includes: calibration frequency, cleaning method, created date, PPM limits, etc. So every time a user create a new blender type, a user will inherit these characteristics and others and, in addition, a user will be able to add their own characteristics. As used herein, the terms business object, category, and table are interchangeable.

As an administrator, the second major meta modeling task, after creating categories, is to create views and sub-views for users. Advantageously, a user can do this dynamically by first selecting a business object and the object within it, and then selecting the characteristics a user want in their view. No programming is involved.

The application in accordance with the present invention has a well organized record management system which serves as a useful tool for creation, retention, destruction and use of records. The library lets a privileged user locate records, add the records directly into the database, have multiple result views, compare records and duplicate them. Information is organized depending on functionality. each function is stored as separate categories or folders. Each category has a set of attributes. There is a parent category which is the base or root of the category hierarchy tree. A child category inherits all attributes of a parent category. For example, "view" is one of the sub categories of metamodel.

To add a new record, one navigates to new record. Under select category, the user clicks on the category a user wants to add attribute records to. Under create new record, the user enters the values. The create new record screen will differ depending upon the category under which a user are adding the record. To add multiple records, a user navigates to administration>library>new record. Under select category, the user clicks on the category a user want to add attribute records to. The create new record screen will differ depending upon the category under which a user are adding the record. To add multiple records, the number of records that a user want to add is entered on the text field before add row(s) button. In order for this text field to show up, a user must have checked the allow multi-record additions check box on the new category page when a user created the above category.

In the present invention, a category represents a database table. It comprises attributes. These attributes are viewed through views and sub views. Categories in a database are associated to one another. These associations create relationships in the database among categories. This relationship creates a category hierarchical structure. A user can add, search, view, modify, duplicate, export and remove a category. The browse data categories screen displays the hierarchical tree structure of category database. The base provides a platform to store categories in the application. A user can add categories: at the base, at the default category folders (e.g., administration, metamodel, organization, people, equipment, material, and process), in the category hierarchy tree. The categories are referred to as parent categories and child categories. A child category inherits the properties of the parent category.

Category. A category can be classified as a system category or a folder category. A system category is a category that provides application data. It comprises attributes of its own. It also allows a user to add data records. A folder category is a container object. However, it does not allow a user to add data records. It can have categories of both system or folder type. They can be referred to as child categories. It has attributes of its own. The child categories inherit the properties of the parent category, as well as have attributes of its own.

Attribute. An attribute represents columns of a category. The attribute can be referred to as category properties. It defines the data type for a column in a category and other necessary user interface and back end properties of the category and attributes. Every attribute is associated with a display type. The user interface types include: a combo box with an option to pick up the data type, a checkbox, an image, and an input text box. The views/sub-views display the attributes as per the user interfaces specified for each attribute. The system category contains the default categories with default attributes. A user can add, search, modify, duplicate, or remove attributes.

Adding a new category. Adding a category includes the following steps: (i) adding a new category under the base or the default folders, (ii) creating schema for a category, (iii) adding attributes for the category, (iv) adding views(v) adding sub-views, and (vi) adding a category at the base. The base category is a default category with common attributes. This is the parent category for all the system categories. The system categories inherit the attributes of the base category. A user can create categories of system or folder type under this category.

Adding a category under the default folders. The system folders provide the data required to construct and manage the application. A user can configure these folders to setup the data in the category required by the client. They include metamodel, system settings, environment, material, equipment, and process folder. The metamodel folder serves to setup default categories for roles, material, equipment, attributes for categories, databases to define type of data, etc. The system settings folder serves to setup user preferences for UOM, date, time etc. The environment folder provides the environment setting for the product material. The material folder provides the setup for the categories for materials. The equipment provides the setup the categories for materials. The process folder provides the setup for the categories for materials.

Creating the schema for the new category. When a new category is added, by default, it is in "schema not created" status. The tables are not created in the database. To create the schema status, a user should create schema. This option is displayed at the bottom of the page with create, refresh schema, and duplicate schemas. A table is created in the database with the category name and the data type. The category status is updated with "schema created." Then, records can be queried from the database. A default view for the category including the inherited and the current attributes is available.

Adding attributes to a category. If a category belongs to a child category type, it inherits the properties of the parent category. A user can add specific attributes to the category. In some embodiments of the present invention, there are two types of attributes, namely, inherited attributes and category specific attributes. The inherited attributes are the attributes inherited from the parent category, if it is a child category.

Adding views to the category. The present invention allows a user to create custom defined views with default view for any category containing the selected type and number of attributes. In one embodiment, adding a view comprises the following steps: selecting the category, assigning a name to the view, determining whether the view should be a system view, and deciding whether the view should have preference over the default view.

Adding sub-views to the category. A view can have many sub-views attached to it. With appropriate privileges, a user can add a sub-view for any main view according to preferences.

Searching a category. A user can search for a category when a user want to modify the category, duplicate the category, move the category, add notes to the category, add attachments to the category or remove a category. The manage menu allows a user to search a category. The browse categories screen displays the category hierarchical tree structure. The search criterion includes all the fields, such as, name, database name, status etc. In some embodiments of the present invention, the search category screen provides the options: categories, attributes, views, and sub-views. The categories option allows a user to find a category with a category name, database name etc. The attributes option allows a user to find categories based on the selected attribute. The views option allows a user to find categories associated with that type of view. The sub-views option allows a user find categories associated with that type of sub-view. The search results screen displays the results based on the search criterion specified. It provides options to modify, duplicate, move and remove categories of that type, export, compare, and attach notes, attachments for future references.

Viewing category details. A user can view the category details. The attributes of the current category and the parent category, the views and sub views can be displayed.

Modifying a category. Modifying a category involves (i) changing the name, label, database name, system flag setting, and/or folder flag setting; (ii) adding or removing associated attributes; (iii) modifying existing attribute details, and (iv) adding or removing associated views, or sub-views. A user can modify a system category to a folder and vice-versa. In preferred embodiments, a user cannot uncheck the allow attachments, allow notes, or allow multi-record additions, if any attachments, notes, or records are attached to the category. If any meta-data information related to schema is changed for an attribute, it will be marked as "schema refresh required" state. A user needs to refresh the schema in order to submit these changes. The category and its views cannot be used to query or edit records in the category in the above state. If a user has administrator's rights, a user can use "refresh schema" option to recreate/refresh the schema in the database. This alters the table structure.

This will also update the default view of the category. A warning is shown to the administrator at this point if there are no primary keys defined for this category. Once the schema is refreshed category schema status will become "schema created". This "refresh schema" action will complete all the pending schema operation of the category & the attributes of the category.

Re-categorizing categories. A user can move a category from one parent category to another parent category. All child categories can be selected and moved to a different parent category. In preferred embodiments, a child category having data in it cannot be moved from one parent to another parent. Moving a category causes the following actions to occur: (i) all the properties inherited from the parent category are removed, (ii) all the existing views are removed, (iii) the old schema is dropped and the schema needs to be created again, and (iv) all the properties of the current parent are inherited. In preferred embodiments, a category cannot be moved if it contains any data.

Duplicating a category. In order to duplicate a category, a user needs to specify a unique name for this duplicated category. All properties of the original category are duplicated, except for the data and the views of the category. The new category will be in "schema not created" state. A user needs to create schema for this category. Child categories of the duplicated category are not duplicated although all the attributes and any other meta data of the original category are copied over to the duplicated category. The views associated with the original category and the data in the category are also not copied.

A user can move this category under any other parent category.

Removing a category. In preferred embodiments of the present invention, a user can remove a category if and only if (i) a category does not have any child categories, (ii) does not hold any data or records in the database, and (iii) does not have any links or references defined into other categories.

Adding a category. In some embodiments of the present invention, adding a category includes the following steps: (i) adding a new category under the base or the default folders, (ii) creating schema for a category, (iii) adding attributes for the category, (iv) adding views, and (v) adding sub-views. The base category is a default category with common attributes. This is the parent category for all the system categories. The system categories inherit the attributes of the base category. A user can create categories of system or folder type under this category. The system folders provide the data required to construct and manage the application. A user can configure these folders to setup the data in the category required by the client. The system folder includes metamodel, system settings, environment, material, equipment, and process. The metamodel folder provide default categories for roles, material, equipment, attributes for categories, databases to define type of data, etc. The system settings folder provides configuration to setup user preferences for UOM, date, time etc. The environment folder defines the environment setting for the product material. The material folder is configured to setup the categories for materials. The equipment folder is configured to setup the categories for materials. The process folder is configured to setup the categories for materials. Any manipulations to the default folders are not recommended except by the administrator.

When a new category is added, by default, it is in "schema not created" status. The tables are not created in the database. To create the schema status, a user should create schema. In some embodiments of the present invention, this option is displayed at the bottom of the page with create; refresh schema, and duplicate schemas. A table is created in the database with the category name and the data type. The category status is updated with "schema created." Now, records can be queried from the database. A default view for the category including the inherited and the current attributes is available.

Adding attributes to a category. If a category belongs to a child category type, it inherits the properties of the parent category. a user can add specific attributes to the category. There are two types of attributes, namely, inherited attributes and category specific attributes. The inherited attributes are the attributes inherited from the parent category, if it is a child category.

Before a user modifies a category, the user needs to browse for it and find out where the category is in the category hierarchy. A user can also view the details of the category, attributes, views and sub views associated with a specific category once a user has selected a category from the data category tree. A user can search for a category when the user wants to modify the category, duplicate the category, move the category, add notes to the category, add attachments to the category, or remove the category. In some embodiments of the present invention, the manage menu allows a user to search a category. The browse categories screen displays the category hierarchical tree structure. The search criterion includes all the fields, such as, name, database name, status, etc. In some embodiments, the search category screen provides the following options: categories, attributes, views, and sub-views. The categories option allows a user to find a category with a category name, database name, etc. The attributes option allows a user to find categories based on the selected attribute. The views option allows a user to find categories associated with that type of view. The sub-views option allows a user find categories associated with that type of sub view. The search results screen displays the results based on the search criterion specified. It provides options to modify, duplicate, move and remove categories of that type, export, compare, and attach notes, attachments for future references.

Modifying a category. Modifying a category involves: (i) changing the name, label, database name, is system flag setting, is folder flag setting; (ii) adding or removing associated attributes, (iii) modifying existing attribute details, and (iv) adding or removing associated views, sub views. A user can modify a system category to a folder and vice-versa. In preferred embodiments, a user cannot uncheck the allow attachments, allow notes, or allow multi-record additions, if any attachments, notes, or records are attached to the category. If any meta-data information related to schema is changed for an attribute, it will be marked as "schema refresh required" state. A user can refresh the schema in order to submit these changes. The category and its views cannot be used to query or edit records in the category in the above state. In preferred embodiments, if a user have administrator's rights, a user can use "refresh schema" option to recreate/refresh the schema in the database. This simply alters the underlying table structure. This will also result in updating the default view of the category. A warning is shown to the administrator at this point if there are no primary keys defined for this category. Once the schema is refreshed category schema status will become "schema created". This "refresh schema" action will complete all the pending schema operation of the category & the attributes of the category.

Duplicating a category. To duplicate a category, a user needs to specify a unique name for this duplicated category. All properties of the original category are duplicated, except for the data and the views of the category. The new category will be in "schema not created" state. A user need creates a schema for this category. Child categories of the duplicated category are not duplicated although all the attributes and any other meta data of the original category are copied over to the duplicated category. The views associated with the original category and the data in the category are also not copied in preferred embodiments of the present invention. A user can move this category under any other parent category.

Moving a category. Advantageously, a user can move a category in the category hierarchy tree. A user can move a category from one parent category to another parent category. All child categories can be selected and moved to a different parent category. A child category having data in it cannot be moved from one parent to another parent. Moving a category modifies the following data in the categories: (i) all the properties inherited from the parent category are removed, (ii) all the existing views are removed, (iii) the old schema is dropped and the schema needs to be created again, (iv) all the properties of the current parent are inherited. A category cannot be moved, if it contains any data.

Removing a category. In preferred embodiments of the present invention, a user can remove a category, if and only if a category (i) does not have any child categories, (ii) does not hold any data or records in the database, and (iii) does not have any links or references defined into other categories.

Adding a new attribute. A user can add attributes. An attribute represents columns of a category. The attribute can be referred to as category properties. It defines the data type for a column in a category and other necessary user UI and back—end properties of the category and attributes. Every attribute is associated with a display type. In some embodiments, the user interface types include: (i) a combo box with an option to pick up the data type, (ii) a checkbox, (iii) an image, and (iv) an input text box. The views/sub-views display the attributes as per the user interfaces specified for each attribute. The system category contains the default categories with default attributes. A user can add, search, modify, duplicate, or remove attributes. In some embodiments of the present invention, selection of a 'value required' option specifies that this attribute cannot have null values. A 'primary key' option specifies that this attribute will be part of the primary key on the category. A 'hidden' option is selected if a user doesn't want this attribute to be displayed on the user interface. A 'privilege required' option is selected for the attribute to have privileges associated with it. An 'auditable' option is selected to set the attribute as auditable (so that all the changes on the attribute are trackable using audit trail). An 'localizable' option is selected for the attribute to be localizable. An 'externally derived' option is selected for the values of this attribute to be derived externally. A web service, specified by the administrator, will fetch the values for externally derived attributes. A 'required in view' option is selected for the attribute to be a part of all the views created on that category. An 'indexed' option is selected for the database column created for this attribute to be indexed.

Searching an attribute. A user will search for an attribute, for example, when a user wants to modify, duplicate or remove an attribute. The manage menu allows a user to search an attribute based on the search criterion specified. The search criterion includes all the fields, such as, name, database name, etc. If no search criterion is specified, the application retrieves all the attributes in the database.

Modifying an attribute. A user can modify an attribute for its data type, display type of an attribute. When there is data in the attribute, and a user change the data type, the data becomes invalid data. A user cannot view the data records with the new data type. If the data type of an attribute is a modification of a category, a user needs to refresh the schema. If a user marks an attribute as non-editable, while defining it, a warning is displayed on the screen which says "this is a non editable attribute". All the fields on the edit screen for this attribute are non-editable, except the 'editable' check box. If the attribute is editable, a user can change all the details of the attributes. Editing an attribute is similar to adding it.

Removing an attribute. In preferred embodiments of the present invention, a user can remove an attribute, only if (i) the attribute does not have any associated data, and (ii) it is not a part of a view/sub-view. In such embodiments, if a user tries to remove an attribute associated to views/sub views that contains data, a message is displayed about the association to views/sub-views. A user needs to remove the attribute associated with the view/sub-view and then remove the attribute. When an attribute is removed from a category, the schema status of that category needs to be updated.

Managing attributes. Attributes represent the characteristics of a category. They specify the data type and other necessary user interface and back-end properties of the category. The attributes of a category can also be referred to as its properties. Attributes are created based on user requirements. To specify an attribute for a category, a user needs to first define a user interface display type. In some embodiments of the present invention, the display types include a combo box with an option to pick up the data type, a check box, image, and an input text box. every attribute is associated with a display type. These display types are displayed in the views/sub-views. The system category folder contain the default categories with default attributes. A user can add, search, modify, duplicate, or remove attributes.

Searching an attribute. A user can search for an attribute. This is desired, for example, when the user wants to modify, duplicate or remove an attribute. The manage menu allows a user to search an attribute based on the search criterion specified. The search criterion includes all the fields, such as, name, database name, etc.

Modifying an attribute. A user can modify an attribute for its data type, display type of an attribute. When there is data in the attribute, and a user changes the data type, the data becomes invalid data. A user cannot view the data records with the new data type. If the data type of an attribute is a modification of a category, a user needs to refresh the schema.

Duplicating an attribute. A user can duplicate an attribute to create a new attribute of a similar type. The attribute duplicated can belong to a parent or a child category. In typical embodiments, when a user duplicates an attribute, a user needs to specify a unique new name and database name of the category. The data of the existing attribute is copied over. to the duplicated attribute.

Inherited attributes and category-specific attributes. There are two types of attributes, namely, inherited attributes and category specific attributes. The inherited attributes are the attributes inherited from the parent category, if it is a child category. The category specific attributes are the specific attributes for the new category. Inherited attributes can only be duplicated and cannot be created, modified or removed.

Adding a new attribute. A user can add attributes. An attribute represents columns of a category. The attribute can be referred to as category properties. It defines the data type for a column in a category and other necessary user UI and back-end properties of the category and attributes. Every attribute is associated with a display type. In some embodiment of the present invention, the user interface types include but are not limited to (i) a combo box with an option to pick up the data type, (ii) a checkbox, (iii) an image, and (iv) an input text box. The views/sub-views display the attributes as per the user interfaces specified for each attribute. The system category contains the default categories with default attributes. A user can add, search, modify, duplicate, or remove attributes. A 'value required' option specifies that this attribute cannot have null values. A 'primary key' specifies that this attribute will be part of the primary key on the category. A 'hidden' option is used when a user doesn't want the attribute to be displayed on the user interface. A 'privilege required' option is used when the attribute has privileges associated with it. An 'auditable' option is used to set the attribute as auditable so that all the changes on the attribute are trackable using audit trail. A 'localizable' option is used when the attribute to be localizable. An 'externally derived' option is used when the values of this attribute to be derived externally. In such instances, a web service, specified by the administrator, will fetch the values for externally derived attributes. A 'required in view' option is used when the attribute is a part of all the views created on that category. An 'indexed' option is used when the database column created for this attribute is to be indexed. In some embodiments, the new attribute details tab is highlighted with the name of the container category and attribute displayed on the top left side of the screen. The field names on the new attribute details tab depends on the data type that the new attribute belongs.

Modifying an attribute. A user can modify an attribute for its data type or display type of an attribute. When there is data in the attribute, and a user changes the data type, the data becomes invalid data. In preferred embodiments, a user cannot view the data records with the new data type. If the data type of an attribute is modified of a category, a user need to refresh schema. If a user mark an attribute as non-editable, while defining it, a warning is displayed on the screen which says "this is a non editable attribute". All the field on the edit screen for this attribute are non editable, except the 'editable' check box. If the attribute is editable, a user can change all the details of the attributes. Editing an attribute is similar to adding it.

Duplicating an attribute. A user will duplicate an attribute to create a new attribute of a similar type. The attribute duplicated can belong to a parent or a child category. When a user duplicates an attribute, the user needs to specify a unique new name and database name of the category. The data of the existing attribute is copied over to the duplicated attribute.

Removing an attribute. In preferred embodiments, a user can remove an attribute, only if (i) the attribute does not have any associated data, and (ii) it is not a part of a view/sub-view. If a user try to remove an attribute associated to views/sub views, contains data, a message is displayed about the association to views/sub-views. a user need to remove the attribute associated with the view/sub-view and then remove the attribute. When an attribute is removed from a category, the schema status of that category needs to be updated.

Managing views. The program allows a user to manage and display a variety of different types of data by creating and customizable views. A user can define the display order of the attributes of each category to be displayed on the screen for each action as views and save the views in the system. By default, the program maintains a view with all the attributes of a category called the 'default' view. This view contains all the attributes of the category including all its inherited attributes. This view cannot be edited or removed by an administrator. With the appropriate rights, a user can create/modify/remove/ duplicate views for a category. Every view has searchable attributes and result attributes associated with it. Search screens are rendered based on the searchable attributes and results screen display values only for result attributes. However, specifying search criteria can perform search using all the result attributes as well. If a foreign key attribute is added to a view, on the search screen, the values for foreign key attribute can be selected via lookup on related category's attributes or as a drop down list of all values in the related category. A user cannot specify the search criteria for a related attribute manually. Views can be marked as system views. These system views can be modified, deleted, duplicated from admit screens but it is understood that a user can potentially break the application by making changes to the system views. A user can modify a view, if a user have the appropriate rights. a user can change the details of the existing view attributes, add, remove or reorder view attributes. Once a view is edited, all existing objects in the application created on that view is invalidated automatically. A warning is displayed if a view is in use, while it is getting edited.

A user can create a new view by basing it on an existing view by duplicating the existing view. A user locates the view, saves it under a different name and modifies the attributes, to create a new duplicated view of the old one. Specifying a new name for the new duplicated view can duplicate any existing view associated with any category. Advantageously, all attributes of the view and associated meta data gets copied over to the newly duplicated view. It is possible to remove a view after all view related data including the view attribute details are removed. If a user has the specific rights, a user can remove any view associated with any category. A user can define sub-views based on a view. If a view contains sub views, all the sub-views of the view will also be removed. A warning, that the view might be in use, is shown to a user on this action.

Adding a view. With administrator rights, a user can add a view for any category including system categories. A view can contain attributes from categories which are related to the owner category of the view. For fetching the attributes from the related categories, the related categories are shown in hierarchical format with category name and foreign key attribute names.

Searching for a view. With administrator rights a user can search view. The searchable parameters to locate a view would be view name, view label, is system flag, display order and description. An administrator can use this functionality to fetch existing views. The administrator can then see details of the view, edit a view, remove a view or clone the view.

Modifying a view. Administrators of an application can edit any view associated with any category. For example, an administrator can change the view name, view label, display locale id, description of the view and display order. Once a view is edited, all existing objects in the system created on that view are invalidated. A warning that the view might be in use is shown to the administrator on this action. An owner category of a view cannot be changed while editing the view. The default view on any category is not allowed to be edited in preferred embodiments of the present invention. In preferred embodiments, an owner category of a view cannot be changed while editing the view.

Duplicate a view. With administrator rights, a user can duplicate a view associated with any category and specify a new name for this duplicated view. All attributes of the view and associated meta data gets copied over to the newly duplicated view. A user can also modify the details of a duplicated view.

View details of a view. As an administrator, a user can details of any view. The details page will display the attributes, custom labels, display order etc.

Remove a view. When removing a view, all view related data including the view attribute details are removed. All sub-views of the view are also removed. A warning, that the view might be in use, is be shown on this action. A "default" view on any category cannot be removed.

Managing sub-views. A sub-view is a subset of a main view. It contains a collection of result attributes on the main view. Sub-views are defined in situations where a user doesn't always want to view all the attributes connected to the main view. Once a user defines a sub-view, the user can switch to it while the user is on a result page. In such instances, only the attributes which are part of the sub-view appears. Sub-view names are localizable. A user can search, modify, duplicate, and remove a sub-view.

Adding a sub-view. With administrator rights, a user can add a sub-view for any main view. The main view can be based on a category which has direct attributes and inherited attributes from the parent category. While creating sub-views, the main view and sub-view name combination should be unique.

Searching for a sub-view. With administrator rights, a user can locate a sub-view associated with any main view. In embodiments, the searchable parameters to locate a view include but are not limited to sub-view name, sub-view label, view, is system flag, display order and description. Administrators can use this functionality to fetch existing sub-views and than see details of the sub-view, edit a sub-view, remove a sub-view or clone the sub-view.

Modifying a sub-view. With administrator rights, a user can edit any sub-view associated with any main view. The administrator can change a name of the sub-view (sub-view name), a label of the sub-view (sub-view label), a system flag (system), a description, and a display order. The administrator can also change details of the existing sub-view attributes, as well as add, remove, and reorder sub-view attributes. In preferred embodiments of the present invention, a user cannot modify a default view. If desired, the administrator can change the details of the existing sub-view attributes, as well as add, remove, and reorder sub-view attributes. Once a sub-view is edited, all existing objects in the application created on that sub view are invalidated. On editing a sub-view that is in use, the application displays a warning. A user can modify/remove a sub-view only if it is not in use.

Viewing a sub-view. A user can also view the details of the sub-view attributes in a hierarchical format. That is, if there are any cross-category attributes added to a sub-view, the information about the owner category and parent foreign key attribute is available.

Duplicating a sub-view. With administrator rights, a user can duplicate a sub-view associated with any main view and specify a new name for this duplicated sub-view. All attributes of the sub-view and associated meta data gets copied over to the newly duplicated sub-view. A user can be able to modify the details of a duplicated sub view.

Removing a sub-view. With administrator rights, a user can remove any sub-view associated with any main view. Once a sub-view is deleted, all existing objects in the system created on that sub-view will be invalidated. A warning that the sub-view might be in use will be shown to the administrator on this action.

Unit of measurement (UOM) management. Unit of measure(UOM), in this context, are measurement units defined by the user which the application will recognize. All custom UOMs can be modified, removed or duplicated according to user preferences. The application allows a user to define a unit of measure and add it into the system as per requirements. UOMs can be added individually or as groups. a UOM group as a collection of one or more unit OD measurements. As an administrator, a user can define a unit of measure (UOM). A collection of UOMs with similar characteristics can be grouped under a name to form a UOM group. With administrator rights, a user can also carry out conversions from one unit of measure to others by specifying the conversion factor. The program allows a user to define UOMs and convert one UOM to another. A unit of measure can be converted to another unit by defining the conversion factor. A UOM conversion is specified by selecting "from UOM", "to UOM" and the conversion formula. A conversion formula is defined as a string expression, in which the macro @original_value represents the value being converted. Advantageously, a user can add, modify, duplicate or remove UOMs, UOM groups, and UOM conversions if a user has the right privileges.

UOM conversion. The program allows its users to define UOMs and convert one UOM to another. A unit of measure can be converted to another unit by defining the conversion factor. A UOM conversion is specified by selecting "from UOM", "to UOM", and the conversion formula. The conversion formula is defined as a string expression, in which the macro @original_value represents the value being converted. If a user is an authorized user, the user can add a unit of measure (UOM) conversion definition into the system. In some embodiments, the formula is specified as text formula expression, where "@original_value" macro is used to represent the value associated with from UOM. This formula text has to be a well formed expression which can be used for calculations. The from UOM and to UOM should belong to same UOM group for defining a conversion. For example: a user cannot convert a kilogram to Celsius. Two unit of measures cannot have more than one conversion factors. With administrator rights, a user can edit a UOM conversion definition at any point of time. A user can remove any unit of measure (UOM) conversion if it is not currently in use. If a UOM is removed from a group, all the conversions associated with the UOM in the current group is removed. A user can also duplicate a UOM conversion, by specifying a new "from UOM" and "to UOM" for the new duplicated UOM conversion. The associations of the original UOM conversion with UOM(s) is not copied over to the duplicated UOM conversion. If a user wants to define more than one UOM conversion, the user enters the number in the 'selected' field and click add row(s). A user may also select a UOM conversion definitions and click remove to remove the UOM conversion definition.

UOM group. a UOM group is a collection of one or more unit OD measurements. A privileged user can define their own unit of measure (UOM) in the system. A collection of UOMs with similar characteristics can be grouped under a name to form a UOM group. A UOM group can be created without having any UOM as well. UOMs can be associated later to the group. The attributes to be added while adding a UOM group are: field header, description, name, name of the UOM group, description, a brief explanation about the behavioral characteristics of the group, alias, another name given to the group, UOM identifier, the identifiers of the UOMs to be included in the group, name, name of the member UOM, description, description of the member, symbol, and symbol associated with the member UOM. Once created, a UOM can be modified if needed, at a later point of time. A user can modify a UOM group changing name, description and the alias associated with the group including the attributes of each individual UOMs in the group. Other attributes of the UOM within a group like display order can also be changed while editing the UOM group. A user needs to have specific rights to modify a unit of measure (UOM) group. If a UOM group is no longer in use, a user can remove it. When a user removes a member UOM from its group, all conversions associated with that UOM in the UOM group are removed as well. When removing a UOM group, all associations with the UOMs are removed, but the UOMs associated are not deleted.

Advantageously, a user can create a new UOM group quickly by copying an existing UOM group and changing its name. This is called duplicating a UOM. Using this feature saves time because a user does not have to re-enter the various attributes for the UOM group. All associations of the original UOM group with UOM(s) are not be copied over to the cloned UOM group. A user can duplicate a UOM group only if a user has the appropriate rights.

The program allows a user to create customized locale by which the headers, help messages, tool tip text and dialogs will appear in your locale. Once a user creates a locale definition and set it as default, then text messages, warning messages and error messages will be shown in logged-in the locale. Name of the month, date, time and time zone etc. will be based on locale.

The present invention can be implemented as a computer program product that comprises a computer program mechanism embedded in a computer readable storage medium. For instance, the computer program product could contain the program modules illustrated in any of the Figures of the present invention. These program modules can be stored on a CD-ROM, DVD, magnetic disk storage product, or any other computer readable data or program storage product. The program modules can also be embedded in permanent storage, such as ROM, one or more programmable chip, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for monitoring a chemical process for the development and manufacture of a drug, the method comprising:
  recording information about the chemical process using a user interface comprising one or more options including an administration option that sets a plurality of user preferences associated with the chemical process; a people management option that defines a user role in said chemical process; an organization option that defines an organizational structure of an organization that runs said chemical process; an equipment option that defines equipment used in said chemical process; a material option that controls a chemical used in said chemical process; and a process option that defines a chemical reaction in the chemical process;
  assigning the recorded information to a plurality of data dimensions, wherein each option corresponds to at least one data dimension;
  determining one or more permanent correlations between data dimensions in the plurality of data dimensions wherein each permanent correlation spans a particular time and corresponds to a particular event in the monitoring of the chemical process;
  storing the one or more permanent correlations;
  determining a context to the information;
  searching the one or more permanent correlations between data dimensions in the plurality of data dimensions in response to the context;
  retrieving information from the one or more permanent correlations and the plurality of data dimensions about the monitoring of the chemical process in view of the context;
  using the information to generate an electronic product history record or electronic development record for inclusion in a submission to a regulatory agency comprising the Food and Drug Administration, the Trade and Tax Bureau, or a state or federal agency involved in the regulation of the development or manufacture of drugs; and
  including the electronic product history record or the electronic development record in the submission to the regulatory agency for regulatory approval of the drug.

2. The method of claim 1, wherein the plurality of user preferences comprises language, currency, time zone, and time format.

3. The method of claim 1, wherein the user role is supplier, distributor, transporter, engineer, chemist, or supervisor.

4. The method of claim 3, wherein the people management option comprises instructions for storing a user profile of each person associated with said chemical process.

5. The method of claim 1, wherein the organization is a company comprising at least one department, at least one site, and at least one location.

6. The method of claim 1, wherein the equipment option facilitates defining new equipment, searching existing equipment, modifying existing equipment, comparing equipment, activating equipment, deactivating equipment, leasing equipment, loaning equipment, making an equipment reservation, checking availability of equipment for reservation, and duplicating equipment.

7. The method of claim 1, wherein the material option facilitates adding a material into inventory, managing a material inventory, tracking a movement and a storage of a material throughout a warehouse, checking availability of a material, allocating inventory by requirement, ordering a material from a vendor, ordering a material from a site, managing a supplier, managing a vendor, managing an order for a material, tracking receipt of a material, managing dispensement of a material, tracking consumption of a material, and managing a material specification plan.

8. The method of claim 1, wherein the process option facilitates locating a project, a campaign, a master batch record, a batch record, and a unit operation.

9. The method of claim 1, wherein the process option facilitates creating a new project, adding personnel to a project, viewing project details, and defining a target molecule for the chemical process.

10. The method of claim 1, wherein the process option facilitates creating one or more campaigns, searching for a campaign, and viewing a plurality of details for a campaign.

11. The method of claim 10, wherein a campaign in the one or more campaigns has a status selected from a status group consisting of draft, submitted, approved, in progress, completed, parked, and cancelled.

12. The method of claim 1, wherein the process option facilitates creating a new master batch record and finding an existing master batch record.

13. The method of claim 1, wherein the process option facilitates creating a new batch record and finding an existing batch record.

14. The method of claim 13, wherein the new batch record comprises a list of all materials used in the chemical process, a list of all equipment used in the chemical process, and each master batch record that defines a batch precursor material for the chemical process or target material of the chemical process.

15. The method of claim 14, wherein each master batch record has a status selected from a status group consisting of draft, submitted, approved, rejected, and obsolete.

16. The method of claim 1, wherein the chemical process comprises one or more unit operations, each unit operation being approved by an administrator.

17. The method of claim 16, wherein each unit operation has a status selected from a status group consisting of draft, submitted, approved, rejected, and obsolete.

18. The method of claim 1, further comprising a views option for customizing a view of a piece of equipment or a view of a chemical used in the chemical process.

19. The method of claim 1, wherein the chemical process is a biological or biochemical process.

20. A computer program product, tangibly embodied in a machine-readable storage device, including instructions operable to cause data processing apparatus to:
   record information about a chemical process, the information being received through a user interface comprising one or more options including an administration module that sets a plurality of user preferences associated with the chemical process; a people management module that defines a user role in said chemical process; an organization module that defines an organizational structure of an organization that runs said chemical process; an equipment module that defines equipment used in said chemical process; a material module that controls a chemical used in said chemical process; and a process module that defines a chemical reaction in the chemical process;
   assign the recorded information to a plurality of data dimensions, wherein each option corresponds to at least one data dimension;
   determine one or more permanent correlations between data dimensions in the plurality of data dimensions wherein each permanent correlation spans a particular time and corresponds to a particular event in the monitoring of the chemical process;
   store the one or more permanent correlations;
   determine a context to the information;
   search the one or more permanent correlations between data dimensions in the plurality of data dimensions in response to the context;
   retrieve information from the one or more permanent correlations and the plurality of data dimensions about the monitoring of the chemical process in view of the context;
   use the information to generate an electronic product history record or electronic development record for inclusion in a submission to a regulatory agency comprising the Food and Drug Administration, the Trade and Tax Bureau, or a state or federal agency involved in the regulation of the development or manufacture of drugs; and
   include the electronic product history record or the electronic development record in the submission to the regulatory agency for regulatory approval of the drug.

21. A computer system for monitoring a chemical process, the computer system comprising a memory coupled with a central processing unit, the memory comprising instructions operable to cause the central processing unit to:
   record information about a chemical process, the information being received through a user interface comprising one or more options including an administration module that sets a plurality of user preferences associated with the chemical process; a people management module that defines a user role in said chemical process; an organization module that defines an organizational structure of an organization that runs said chemical process; an equipment module that defines equipment used in said chemical process; a material module that controls a chemical used in said chemical process; and a process module that defines a chemical reaction in the chemical process;
   assign the recorded information to a plurality of data dimensions, wherein each option corresponds to at least one data dimension;
   determine one or more permanent correlations between data dimensions in the plurality of data dimensions wherein each permanent correlation spans a particular time and corresponds to a particular event in the monitoring of the chemical process;
   store the one or more permanent correlations;
   determine a context to the information;
   search the one or more permanent correlations between data dimensions in the plurality of data dimensions in response to the context;
   retrieve information from the one or more permanent correlations and the plurality of data dimensions about the monitoring of the chemical process in view of the context;
   use the information to generate an electronic product history record or electronic development record for inclusion in a submission to a regulatory agency comprising the Food and Drug Administration, the Trade and Tax Bureau, or a state or federal agency involved in the regulation of the development or manufacture of drugs; and
   include the electronic product history record or the electronic development record in the submission to the regulatory agency for regulatory approval of the drug.

* * * * *